United States Patent [19]

Bovy et al.

[11] Patent Number: 5,220,050

[45] Date of Patent: Jun. 15, 1993

[54] PEPTIDE MIMETIC COMPOUNDS USEFUL AS PLATELET AGGREGATION INHIBITORS

[75] Inventors: Philippe R. Bovy, St. Louis; Dudley E. McMackins, St. Charles; Joseph G. Rico; Foe S. Tjoeng, both of Manchester; Mihaly V. Toth, St. Louis, all of Mo.; Robert B. Garland; Masateru Miyano, both of Northbrook, Ill.; Jeffery A. Zablocki, Skokie, Ill.

[73] Assignee: G. D. Searle & Co., Chicago, Ill.

[21] Appl. No.: 792,542

[22] Filed: Nov. 12, 1991

Related U.S. Application Data

[63] Continuation-in-part of Ser. No. 702,667, May 17, 1991, abandoned.

[51] Int. Cl.$^5$ .................................... C07C 229/00
[52] U.S. Cl. ............................ 514/357; 560/13; 560/35; 562/440; 562/623; 558/414; 546/332; 564/147; 564/163; 549/58; 549/77; 549/441; 514/539; 514/533; 514/542; 514/563; 514/438; 514/443; 514/468
[58] Field of Search .................... 560/35, 13; 562/440, 562/612, 623; 558/414; 546/409; 564/147, 163; 549/58, 77, 441; 514/539, 533, 542, 563, 438, 443, 468, 357

[56] References Cited

U.S. PATENT DOCUMENTS

| | | | |
|---|---|---|---|
| 4,517,686 | 5/1985 | Ruoslahti et al. | 514/12 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,791,102 | 12/1988 | Bernat et al. | 514/19 |
| 4,857,508 | 8/1989 | Adams et al. | 514/18 |
| 4,879,313 | 11/1989 | Tjoeng et al. | 514/616 |
| 4,977,168 | 12/1990 | Bernat et al. | 514/330 |

FOREIGN PATENT DOCUMENTS

| | | |
|---|---|---|
| 0275748 | 7/1988 | European Pat. Off. |
| 0298820 | 1/1989 | European Pat. Off. |
| 0372486 | 6/1990 | European Pat. Off. |
| 0381033 | 8/1990 | European Pat. Off. |
| 0410540 | 1/1991 | European Pat. Off. |
| 0445796 | 9/1991 | European Pat. Off. |

OTHER PUBLICATIONS

Kloczewiak, et al., *Biochem.*, 23, 1767–1774 (1984).
Ruggeri, et al., *Proc. Natl. Acad. Sci.*, 83, 5708–5712 (1986).

(List continued on next page.)

*Primary Examiner*—Paul J. Killos
*Attorney, Agent, or Firm*—Joy Ann Serauskas; Paul D. Matukaitis

[57] ABSTRACT

This invention relates to having the following formula $$
\underset{NH}{\overset{H_2N}{\diagdown}}\!\!\!\diagup\!\!\!\!\diagdown\!\!\!\!\!-\!\!\!\!\overset{R_6}{\underset{R_5}{\diagup}}\!\!\!-Y-\overset{O}{\overset{\|}{C}}-\overset{H}{\underset{|}{N}}-\overset{R_3}{\underset{R_2}{C}}\!\!\!-\overset{O}{\overset{\|}{C}}-W \qquad I
$$

or a pharmaceutically acceptable salt which are useful in the inhibition of platelet aggregation. This invention also relates to pharmaceutical compositions of such phenyl amidines derivatives.

157 Claims, No Drawings

OTHER PUBLICATIONS

Plow, et al., *Proc. Natl. Acad. Sci.*, 82, 8057–8061 (1985).
Ginsberg, et al., *J. Biol. Chem.*, 260, (7), 3931–3936 (1985).
Haverstick, et al., *Blood*, 66, (4), 946–952 (1985).
Ruoslahti and Pierschbacher, *Science*, 238, 491–497 (1987).
R. Ferroni, et al. "Ethyl Esters of N-Amidinobenzoyl Amino Acids: Inhibitory Effects on Thrombin, Blood Coagulation, and Platelet Aggregation," *Farmaco, Ed. Sci.*, vol. 42, No. 10, pp. 709–715, 1987.
T. Yokoyama, et al. "New Synthetic Inhibitors of Chymotrypsin, Thrypsin, Thrombin, Plasmin, Urokinase, Tissue Plasminogen Activator, Factor Xa, Tissue Kallikrein, and Plasma Kallikrein," *Jap. J. Clin. Chem.*, vol. 15, No. 6, pp. 338–344, 1986.
J. Stuerzebecher, et al. "Synthetic Inhibitors of Serine Proteinases, Part 32—Inhibition of Trypsin, Plasmin and Thrombin by Amides of Amino Acids and Blocking Groups of the N-Alpha-Residue On the Inhibitor Activity," *Pharmazie*, vol. 42, No. 2, pp. 114–116, 1987.
B. Voight, et al. "Synthesis of N-Alpha-Benzyloxycarbonyl-amidino-phenylalanine Amide as Thrombin Inhibitors," *Pharmazie*, vol. 40, No. 5, pp. 305–306, 1985.
J. Stuerzebecher, et al. "Synthetic Inhibitors of Serine Proteases, 13.Quantitative Structure-Activity Relations for Inhibition of Trypsin, Plasmin, and Thrombin by 4-amidino-phenyl Compounds with a Keto Group," *Acta. Biol. Med. Ger.*, vol. 35, No. 12, pp. 1665–1676, 1976.

PEPTIDE MIMETIC COMPOUNDS USEFUL AS PLATELET AGGREGATION INHIBITORS

This application is a continuation-in-part of U.S. Ser. No. 07/702,667, filed May 17, 1991, now abandoned.

FIELD OF THE INVENTION

This invention is in the field of mammalian therapeutics and relates to compounds for the treatment of mammalian disorders such as cardiovascular disorders. Of particular interest is a class of phenyl amidine derivatives useful as inhibitors of platelet aggregation.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb-/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., Ibid. 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 292,820.

U.S. Pat. No. 4,879,313 discloses compounds useful as inhibitors of platelet aggregation having the formula:

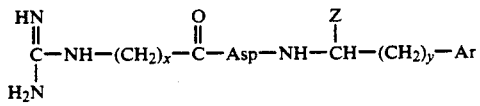

wherein x = 6 to 10,
y = 0 to 4,
Z = H, COOH, CONH$_2$ OR C$_{1-6}$ alkyl,
Ar = phenyl, biphenyl or naphthyl, each substituted with 1 to 3 methoxy groups, or an unsubstituted phenyl, biphenyl, naphthyl, pyridyl or thienyl group, and
Asp = aspartic acid residue.

U.S. Pat. No. 4,977,168 discloses compounds having the following structural formula

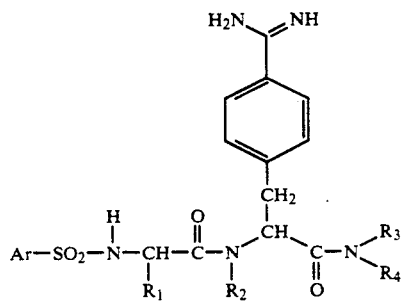

wherein

R$_1$ represents hydrogen, a lower alkyl group, a lower hydroxyalkyl group, a benzyl group, a phenyl group or a 4-hydroxyphenyl group;

R$_2$ represents a lower alkyl, lower alkenyl, lower alkynyl or benzyl group, or a lower alkoxycarbonylalkyl, lower carboxyalkyl, or lower hydroxyalkyl group;

R$_3$ and R$_4$ identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino not substituted o substituted by an alkoxycarbonyl or carboxy group, piperazino, 4-(lower alkyl)piperazino, 4-(lower hydroxyalkyl)piperazino, or piperidino not substituted or substituted by one of the following groups: lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group possibly substituted, or a heteroaryl group chosen from the radicals pyridyl, quinolinyl, or isoquinolinyl, possibly substituted, as well as their isomers and their mixtures and their salts with pharmaceutically acceptable mineral or organic acids which are useful as antithrombotic agents. These compounds are structural distinct from the present invention because they are arylsulphonylaminoacyl aminophenylalaninamide derivatives in contrast to the compounds of the present invention which are propanoic acid/esters-1-amidinophenylalkyl carbonylamino derivatives.

U.S. Pat. 4,791,102 discloses compounds having the following structural formula

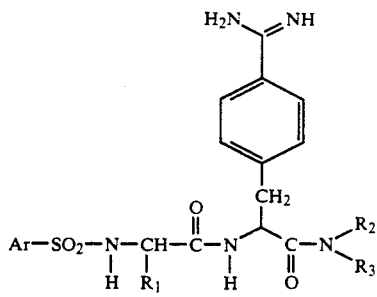

wherein
- R₁ represents a lower alkyl, lower hydroxyalkyl, or benzyl group, a phenyl or a 4-hydroxyphenyl group.
- R₂ and R₃ identical or different, each represents a lower alkyl or hydroxyalkyl, lower alkenyl or lower alkynyl radical, or they form together with the nitrogen to which they are attached, a saturated heterocycle such as morpholino, thiomorpholino, pyrrolidino unsubstituted or substituted by an alkoxycarbonyl or carboxyl group, piperazino, 4-(lower alkyl)-piperazino or piperidino unsubstituted or substituted by a lower alkyl, benzyl, hydroxy, lower hydroxyalkyl, amino, lower aminoalkyl, alkoxycarbonyl or carboxyl group.
- Ar represents a phenyl, a possibly substituted alpha-naphthyl or beta-naphthyl group, or else a heteroaryl group chosen from pyridyl, quinolinyl, isoquinolinyl, possibly substituted which are useful as selective inhibiting agents of thrombin and antithrombotics. These compounds are structural distinct from the present invention because they are arylsulphonylaminoacylaminophenyl alaninamides in contrast to the compounds of the present invention which are propanoic acid/esters-1-amidinophenylalkylcarbonyl amino derivatives.

European Patent Application 372,486 discloses N-acyl beta amino acid derivatives of the formula:

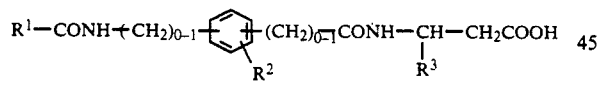

and their salts. Said compounds are useful for inhibiting platelet aggregation in the treatment of thrombosis, stroke, myocardial infarction, inflammation and arteriosclerosis, and for inhibiting metastasis.

European Patent Application 381 033 A1 discloses amidino or guanidino-aryl substituted alkanoic acid derivatives having the following structural formula

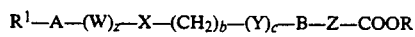

which are useful for the treatment of thrombosis, apoplexy, cardiac infarction, inflammation, arteriosclerosis and tumors. These compounds are structural distinct from the present invention because they are aryl acetic acid/esters 2-amidino/guanidino phenylalkylcarbonyl amino derivatives in contrast to the compounds of the present invention which are propanoic acid/esters-1-amidinophenylalkylcarbonyl amino derivatives.

European Patent Application 445,796 A2 discloses acetic acid derivatives having the formula

H₂N(NH)C—X—Y—CO—Z—CH(Q¹)COOQ² (FORMULA A)

where
- Q¹ stands for hydrogen, methyl or phenyl,
- Q² stands for hydrogen, phenyl-low-alkyl or low alkyl that can be cleaved under physiological conditions,
- X stands for 1,4-phenylene, 2,5- or 3,6-pyridylene or, 1,4-piperidinylene, which is bonded to group Y through the C atom in the 4-position,
- Y is a group having the formula

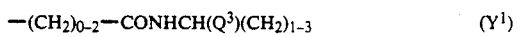 (Y¹)

 (Y²)

 (Y³)

 (Y⁴)

 (Y⁵)

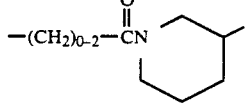 (Y⁶)

OR

 (Y⁷)

where
- Q³ stands for hydrogen, methyl, phenyl, —COOH, —COO—low-alkyl, —CONH(CH₂)₂—COOH or —CONH(CH₂)₂—COO-low-alkyl,
- Q⁴ hydrogen, methyl or phenyl,
- Z a 1,4-piperazinylene group, a 1,4-piperazinylene group which is bonded to the CO group through the N atom in the 1-position or a group having the formula

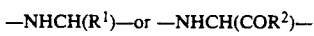

where
- R¹ stands for hydrogen, methyl, phenyl or a —COO-low-alkyl,
- R² stands for the residue of an α-aminocarboxylic acid bonded through the amino group or of an ester or amide thereof, or a group having the formula —NHCH₂CH₂—Ar—, or —CO—R², or, if applicable, a mono- or di-low-alkylated carbamoyl group or a pyrrolidinoyl or piperidinoyl group,
- Ar stands for a phenyl or a phenyl substituted by low alkyl, low alkoxy, —COOH, —COO-low-alkyl, —O(CH₂)₁₋₄—COOH, —O(CH₂)₁₋₄—COO-low-alkyl, —CONH₂, —CONH-low-alkyl, —CON(-low alkyl)₂, pyrrolidinoyl or piperidinoyl which are said to have inhibitory action on the bonding of adhesive proteins to blood platelets as well as blood platelet aggregation and cell-cell adhesion. These compounds are structurally distinct from the present invention because they have an additional —NHCH($R^1$) or —NHCH($COR^2$)—or a piperazinylene group at the "Z" position of Formula A.

An additional —NHCH($R^1$) or an additional —NHCH($COR^2$) or a piperazinylene group is not present in the instant invention.

SUMMARY OF THE INVENTION

The present invention relates to a class of compounds represented by the formula:

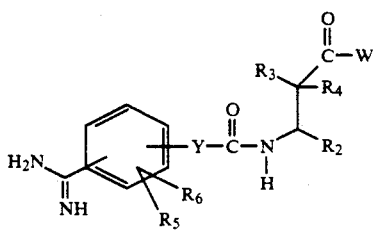

or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is hydrido, alkyl having 1 to 6 carbon atoms, alkenyl having 2 to 6 carbon atoms, cycloalkyl having 3 to 8 ring carbon atoms, cycloalkenyl having 5 or 6 ring carbon atoms and wherein any of said alkyl, said alkenyl, said cycloalkyl and said cycloalkenyl may be substituted with one or more groups selected from alkyl having 1 to 6 carbon atoms, alkoxy having 1 to 6 carbon atoms, halo and hydroxy; or $R_2$ is phenyl, phenylalkyl wherein the alkyl is $C_1$ to $C_6$, naphthyl, naphthylalkyl wherein the alkyl is $C_1$ to $C_6$, the group phenyl-Q-phenyl wherein Q is a direct single bond, or the group $O(R_7)_n$ wherein O represents oxygen and $R_7$ is an alkyl having 1 to 6 carbon atoms and n is the integer zero or one and wherein any of said phenyl, said phenylalkyl, said naphthyl and said naphthylalkyl may be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carboxyl, alkyloxycarbonyl wherein the alkyl is $C_1$ to $C_6$ and aminoiminomethyl and wherein any one of the phenyl rings of the said phenyl-Q-phenyl group may be substituted with one or more groups selected from alkyl having 1 to 6 carbon atoms, alkoxy having 1 to 6 carbon atoms, trifluoromethyl and halo; or $R_2$ is a heteromonocyclic ring structure having 5 or 6 ring carbon atoms wherein 1 or 2 of the ring carbon atoms are replaced by nitrogen, oxygen or sulfur and Wherein the ring is selected from saturated, partially unsaturated, and fully unsaturated rings or a fused bicyclic ring structure having 10 to 12 ring carbon atoms wherein 1 to 3 of the ring carbon atoms may be replaced by nitrogen, oxygen or sulfur and each ring may independently be saturated, partially unsaturated or fully unsaturated and wherein said heteromonocyclic ring structure and each ring of said fused bicyclic ring structure may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo;

The invention further relates to pharmaceutical compositions comprising a compound of Formula I. Such compounds and compositions have usefulness as inhibitors of platelet aggregation. The invention also relates to a method of inhibiting platelet aggregation in a mammal in need of such treatment.

A preferred embodiment of the present invention is a compound of the formula:

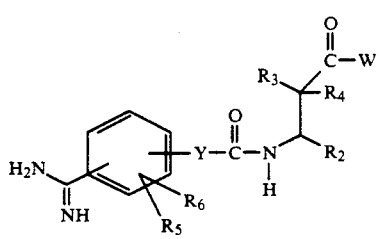

or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is hydrido, alkyl having 1 to 6 carbon atoms, alkenyl having 2 to 6 carbon atoms, cycloalkyl having 3 to 8 ring carbon atoms or cycloalkenyl having 5 or 6 ring carbon atoms and Wherein any of said alkyl, said alkenyl, said cycloalkyl and said cycloalkenyl may be substituted with one or more groups selected from alkyl having 1 to 6 carbon atoms, alkoxy having 1 to 6 carbon atoms, halo and hydroxy;

R₃ and R₄ are each independently selected hydrido, alkyl having 1 to 6 carbon atoms, hydroxy and halo;

R₅ and R₆ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo.

Exemplifying this embodiment are the following compounds:

N-[5-[4-(aminoiminomethyl)phenyl]-1-oxopentyl]-2-fluoro-β-alanine;

3-[[5-[4-(aminoiminomethyl)phenyl]-1-oxopentyl]amino]butanoic acid;

ethyl 3-[[5-[4-(aminoiminomethyl)phenyl]-1-oxopentyl]amino]butanoate;

N-[5-[4-(aminoiminomethyl)phenyl]-1-oxopentyl]-2-hydroxy-β-alanine;

N-[5-[4-(aminoiminomethyl)phenyl]-1-oxopentyl]-β-alanine;

N-[5-[4-(aminoiminomethyl)phenyl]-1-oxopentyl]-β-alanine, phenylmethyl ester;

ethyl 3-[[5-[4-(aminoiminomethyl)phenyl]-1-oxopentyl]amino]-4-pentenoate;

ethyl 3-[[5-[4-(aminoiminomethyl)phenyl]-1-oxopentyl]amino]-5-methylhexanoate;

3-[[5-[4-(aminoiminomethyl)phenyl]-1-oxopentyl]amino]-4-pentenoic acid;

3-[[5-[4-(aminoiminomethyl)phenyl]-1-oxopentyl]amino]-5-methylhexanoic acid;

β-[[5-[4-(aminoiminomethyl)phenyl]-1-oxopentyl]amino]-3-cyclohexene-1-propanoic acid;

3R-[[5-[4-(aminoiminomethyl)phenyl]-1-oxopentyl]amino]butanoic acid;

β-[[5-[4-(aminoiminomethyl)phenyl]-1-oxopentyl]amino]cyclohexanepropanoic acid;

3-[[5-[4-(aminoiminomethyl)phenyl]-4-methylene-1-oxopentyl]amino]butanoic acid;

3-[[5-[4-(aminoiminomethyl)phenyl]-4-methyl-1-oxopentyl]amino]butanoic acid; and 3-[[5-[4-(aminoiminomethyl)phenyl]-1-oxopentyl]amino]pentanoic acid.

A further preferred embodiment of the present invention is a compound of the formula:

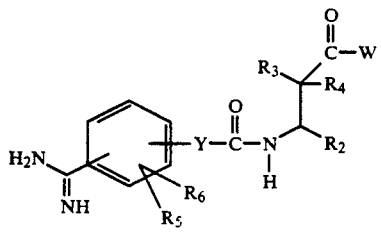

or a pharmaceutically acceptable salt thereof, wherein W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is phenyl, phenylalkyl wherein the alkyl is $C_1$ to $C_6$, naphthyl, naphthylalkyl wherein the alkyl is $C_1$ to $C_6$ or the group phenyl-Q-phenyl wherein Q is a direct single bond or the group $O(R_7)n$ wherein O represents oxygen and $R_7$ is an alkyl having 1 to 6 carbon atoms and n is the integer zero or one and wherein any of said phenyl, said phenylalkyl, said naphthyl and said naphthylalkyl may be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carboxyl, alkyloxycarbonyl wherein the alkyl is $C_1$ to C6 and aminoiminomethyl and wherein any one of the phenyl rings of the said phenyl-Q-phenyl group may be substituted with one or more groups selected from alkyl having 1 to 6 carbon atoms, alkoxy having 1 to 6 carbon atoms, trifluoromethyl and halo;

R₃ and R₄ are each independently selected from hydrido, alkyl having 1 to 6 carbon, hydroxy and halo;

R₅ and R₆ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo Exemplifying this embodiment are the following compounds:

β-[[5-[4-(aminomethyl)phenyl]-1-oxopentyl]amino]benzenepropanoic acid, acetate salt;

β-[[5-[4-(aminoiminomethyl)phenyl]-1-oxopentyl]amino]benzenebutanoic acid;

ethyl β-[[5-[4-(aminoiminomethyl)phenyl]-1-oxopentyl]amino]benzenepropanoate;

ethyl β-[[5-[4-(aminoiminomethyl)phenyl]-1-oxopentyl]amino]-4-bromobenzenepropanoate;

β-[[5-[4-(aminoiminomethyl)phenyl]-1-oxopentyl]amino]-2,4-dichlorobenzenepropanoic acid;

β-[[5-[4-(aminoiminomethyl)phenyl]-1-oxopentyl]amino]-4-bromobenzenepropanoic acid;

ethyl β-[[5-[4-(aminoiminomethyl)phenyl]-1-oxopentyl]amino]-4-chlorobenzenepropanoate;

β-[[5-[4-(aminoiminomethyl)phenyl]-1-oxopentyl]amino]-4-chlorobenzenepropanoic acid;

ethyl β-[[5-[4-(aminoiminomethyl)phenyl]-1-oxopentyl]amino]benzenepentanoate;

β-[[5-[4-(aminoiminomethyl)phenyl]-1-oxopentyl-]amino]benzenepentanoic acid;
ethyl β-[[5-[4-(aminoiminomethyl)phenyl]-1-oxopentyl-]amino]-4-(ethoxycarbonyl) benzenepropanoate;
β-[[5-[4-(aminoiminomethyl)phenyl]-1-oxopentyl-]amino]-4-carboxybenzenepropanoic acid;
ethyl β-[[5-[4-(aminoiminomethyl)phenyl]-1-oxopentyl-]amino]-3,5-dichlorobenzenepropanoate;
β-[[5-[4-(aminoiminomethyl)phenyl]-1-oxopentyl-]amino]-3,5-dichlorobenzenepropanoic acid;
β-[[5-[4-(aminoiminomethyl)phenyl]-1-oxopentyl-]amino]-2,6-dichlorobenzenepropanoic acid;
ethyl β-[[5-[4-(aminoiminomethyl)phenyl]-1-oxopentyl-]amino]-3,4-dichlorobenzenepropanoate;
β-[[5-[4-(aminoiminomethyl)phenyl]-1-oxopentyl-]amino]-3,4-dichlorobenzenepropanoic acid;
-[[5-[4-(aminoiminomethyl)phenyl]-1-oxopentyl-]amino]-2-chloro-6-fluorobenzenepropanoic acid;
β-[[5-[4-(aminoiminomethyl)phenyl]-1-oxopentyl-]amino]-3,4-dimethoxybenzenepropanoic acid;
β-[[5-[4-(aminoiminomethyl)phenyl]-1-oxopentyl-]amino]-3-fluorobenzenepropanoic acid;
β-[[5-[4-(aminoiminomethyl)phenyl]-1-oxopentyl-]amino]-3-methoxybenzenepropanoic acid;
β-[[5-[4-(aminoiminomethyl)phenyl]-1-oxopentyl-]amino]-3,5-dimethoxybenzenepropanoic acid;
β-[[5-[4-(aminoiminomethyl)phenyl]-1-oxopentyl-]amino]-4-cyanobenzenepropanoic acid;
β-[[5-[4-(aminoiminomethyl)phenyl]-1-oxopentyl-]amino]-2,4-dimethoxybenzenepropanoic acid;
ethyl β-[[5-[4-(aminoiminomethyl)phenyl]-1-oxopentyl-]amino]-3,4-dimethoxybenzenepropanoate;
ethyl β-[[5-[4-(aminoiminomethyl)phenyl]-1-oxopentyl-]amino]-3,5-dimethoxybenzenepropanoate;
ethyl β-[[5-[4-(aminoiminomethyl)phenyl]-1-oxopentyl-]amino]-2,4-dimethoxybenzenepropanoate;
ethyl β-[[5-[4-(aminoiminomethyl)phenyl]-1-oxopentyl-]amino]-4-ethoxybenzenepropanoate;
ethyl β-[[5-[4-(aminoiminomethyl)phenyl]-1-oxopentyl-]amino]-4-cyanobenzenepropanoate;
ethyl β-[[5-[4-(aminoiminomethyl)phenyl]-1-oxopentyl-]amino]-3-fluorobenzenepropanoate;
β-[[5-[4-(aminoiminomethyl)phenyl]-1-oxopentyl-]amino]-4-ethoxybenzenepropanoic acid;
β-[[5-[4-(aminoiminomethyl)phenyl]-1-oxopentyl-]amino]-4-fluorobenzenepropanoic acid;
β-[[5-[4-(aminoiminomethyl)phenyl]-1-oxopentyl-]amino]-2,5-dimethoxybenzenepropanoic acid;
β-[[5-[4-(aminoiminomethyl)phenyl]-1-oxopentyl-]amino]-2-fluorobenzenepropanoic acid;
β-[[5-[4-(aminoiminomethyl)phenyl]-1-oxo-4pentynyl-]amino]benzenepropanoic acid;
(+)-ethyl β-[[5-[4-(aminoiminomethyl)phenyl]-1-oxopentyl]amino]benzeneheptanoate;
β[[5-[4-(aminoiminomethyl)phenyl]-1-oxopentyl-]amino]-4-methoxybenzenebutanoic acid;
β-[[5-[4-(aminoiminomethyl)phenyl]-1-oxopentyl-]amino]benzeneheptanoic acid;
ethyl β-[[5-[4-(aminoiminomethyl)phenyl]-1-oxopentyl-]amino]benzenebutanoate;
(±)-β-[[5-[4-(aminoiminomethyl)phenyl]-1-oxopentyl-]amino-2-hydroxybenzenepropanoic acid;
β-[[5-[4-(aminoiminomethyl)phenyl]-1-oxopentyl-]amino]-4-(trifluoromethyl)benzenepropanoic acid;
β-[[5-[4-(aminoiminomethyl)phenyl]-1-oxopentyl-]amino]-3-(trifluoromethyl)benzenepropanoic acid;
β-[[5-[4-(aminoiminomethyl)phenyl]-1-oxopentyl-]amino]-3-cyanobenzenepropanoic acid;
(±)-β-[[5-[4-(aminoiminomethyl)phenyl]-1-oxopentyl-]amino]-2-hydroxy-4-methoxybenzenepropanoic acid;
β-[[5-[4-(aminoiminomethyl)phenyl]-1-oxopentyl-]amino]-N-hydroxybenzenepropanamide;
β-[[5-[4-(aminoiminomethyl)phenyl]-1-oxopentyl-]amino]-4-hydroxybenzenepropanoic acid;
3-(aminoiminomethyl)-β-[[5-[4-(aminoiminomethyl)-phenyl]-1-oxopentyl]amino]benzenepropanoic acid
4-(aminoiminomethyl)-β-[[5-[4-(aminoiminomethyl)-phenyl]-1-oxopentyl]amino]benzenepropanoic acid
βR-[[5-[4-(aminoiminomethyl)phenyl]-1-oxopentyl-]amino]-1-naphthalenebutanoic acid;
ethyl β-[[5-[4-(aminoiminomethyl)phenyl]-1-oxopentyl-]amino][1,1'-biphenyl]-4-propanoate;
ethyl β-[[5-[4-(aminoiminomethyl)phenyl]-1-oxopentyl-]amino]-4-(phenylmethoxy) benzenepropanoate;
β-[[5-[4-(aminoiminomethyl)phenyl]-1-oxopentyl-]amino]-4-(phenylmethoxy)benzenepropanoic acid;
β-[[5-[4-(aminoiminomethyl)phenyl]-1-oxopentyl-]amino]-4-phenoxybenzenepropanoic acid;
β-[[5-[4-(aminoiminomethyl)phenyl]-1-oxopentyl-]amino]-3-phenoxybenzenepropanoic acid;
ethyl β-[[5-[4-(aminoiminomethyl)phenyl]-1-oxopentyl-]amino]-4-phenoxybenzenepropanoate;
ethyl β-[[5-[4-(aminoiminomethyl)phenyl]-1-oxopentyl-]amino]-3-phenoxybenzenepropanoate; and
β-[[5-[4-(aminoiminomethyl)phenyl]-1-oxopentyl-]amino][1,1'-biphenyl]-4-propanoic acid, acetate salt.

Another preferred embodiment of the present invention is a compound of the formula:

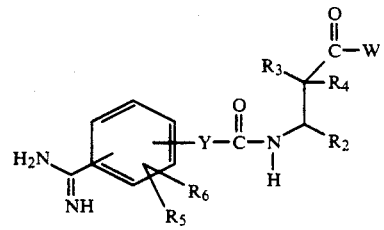

or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is a heteromonocyclic ring structure having 5 or 6 ring carbon atoms wherein 1 or 2 of the ring carbon atoms are replaced by nitrogen, oxygen or sulfur and wherein the ring is selected from saturated, partially unsaturated, and fully unsaturated rings or a fused bicyclic ring structure having 10 to 12 ring carbon atoms wherein 1 to 3 of the ring carbon atoms may be replaced by nitrogen, oxygen or sulfur and each ring may independently be saturated, partially unsaturated or fully unsaturated and wherein said heteromonocyclic ring structure and each ring of said fused bicyclic ring structure may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo.

Exemplifying this embodiment are the following compounds:

β-[[5-[4-(aminoiminomethyl)phenyl]-1-oxopentyl]amino]-3-pyridinepropanoic acid;

ethyl β-[[5-[4-(aminoiminomethyl)phenyl]-1-oxopentyl]amino]-3-pyridinepropanoate;

cyclohexyl β-[[5-[4-(aminoiminomethyl)phenyl]-1-oxopentyl]amino]-3-pyridinepropanoate;

3-[1-[[5-[4-(aminoiminomethyl)phenyl]-1-oxopentyl]amino]-2-carboxyethyl]-1-methylpyridinium chloride;

ethyl β-[[5-[4-(aminoiminomethyl)phenyl]-1oxopentyl]amino]-2-pyridinepropanoate;

β-[[5-[4-(aminoiminomethyl)phenyl]-1-oxopentyl]amino]-2-pyridinepropanoic acid;

β-[[5-[4-(aminoiminomethyl)phenyl]-1-oxopentyl]amino]-2-thiophenepropanoic acid;

β-(R)-R-[[5-[4-(aminoiminomethyl)phenyl]-1-oxopentyl]amino]-3-benzo[b]thiophenebutanoic acid;

ethyl β-(R)-R-[[5-[4-(aminoiminomethyl)phenyl]-1-oxopentyl]amino]-3-benzo[b]thiophenebutanoate;

β-[[5-[4-(aminoiminomethyl)phenyl]-1-oxopentyl]amino]-1,3-benzodioxole-5-propanoic acid; and ethyl β-[[5-[4-(aminoiminomethyl)phenyl]-1-oxopentyl]amino]-1,3-benzodioxole-5-propanoate As used herein, the term "hydrido" denotes a single hydrogen atom (H). This hydrido group may be attached, for example, to a oxygen atom to form a hydroxyl group; or, as another example, two hydrido groups may be attached to a carbon atom to form a —$CH_2$—group.

As used herein, the term "alkyl", either alone or within other terms such as "phenylalkyl", "naphthylalkyl" and "alkyloxycarbonyl" embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenoxy, 3-methylbutoxy, 1-methylbutoxy, 1-ethylpropoxy, 2-2-dimethylpropoxy, 11,-dimethylpropoxy, hexoxy, and 4-methylpentoxy.

As used herein the term "alkenyl" embraces linear or branched unsaturated hydrocarbon radicals having 2 to 6 carbon atoms and containing at least one carbon to carbon double bond, which carbon to carbon double bond may have either cis or trans geometry within the alkenyl moiety. Illustrative of such groups are ethenyl, propenyl, butenyl, isobutenyl, pentenyl, 3-methyl-1-butenyl, 2-methyl-2-butenyl, 2,3-dimethyl-2-butenyl and hexenyl.

As used herein the term "alkynyl" embraces linear or branched unsaturated hydrocarbon radicals having 2 to 6 carbon atoms and containing one carbon to carbon triple bond. Illustrative of such radicals are ethynyl, propynyl, butynyl, pentynyl, and hexynyl.

As used herein the term "halo" embraces halogen atoms. Illustrative of such atoms are chloro (Cl), fluoro (F), bromo (Br) and iodo (I).

As used herein the term "alkoxycarbonyl" represents the radical of the formula

ROCO— wherein the R represents an alkyl group. Illustrative of such radicals are methoxycarbonyl, ethoxycarbonyl, propanoxycarbonyl, pentanoxycarbonyl and hexoxycarbonyl.

As used herein the term "sulfonyl," whether used alone or within other terms such as sulfonylalkyl represents the divalent radical —$SO_2$—.

As used herein the term "carbonylalkyl" represents the radical of the formula

COR wherein the R represents an alkyl group. Illustrative of such radicals are carbonylmethyl, carbonylethyl, carbonylpropyl, carbonylbutyl, carbonylpentyl and carbonylhexyl.

As used herein the term "cycloalkyl" embraces cyclic saturated hydrocarbon radicals having 3 to 8 ring carbon atoms. Illustrative of such radicals are cyclopropyl, cyclobutyl, cyclopentyl, cyclohexyl, cycloheptyl and cyclooctanyl.

As used herein the term "cycloalkenyl" embraces cyclic unsaturated hydrocarbon radicals having 5 or 6 ring carbon atoms including one double bond involving adjacent ring carbon atom which may be at any position in the ring. Illustrative of such radicals are cyclopentenyl and cyclohexenyl.

As used herein the term "phenyl-Q-phenyl" represents the radical of the formula

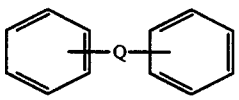

wherein Q represents a direct single bond or the group $O(R_7)_n$ wherein 0 represents oxygen and $R_7$ is an alkyl radical having 1 to 6 carbon atoms and n is the integer zero or one. When Q represents a direct single bond in the above formula a biphenyl group is intended.

As used herein the term "naphthyl" represents a radical of formula

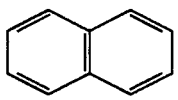

Attachment of the naphthyl radical to the remaining portion of the molecule represented by formula I may be through a ring carbon atom of the naphthyl radical or the naphthyl radical may be attached through a substituent of the naphthyl radical for example through the methylene substituent of the naphthylmethyl moiety.

As used herein the term "naphthylalkyl" represents a radical of formula

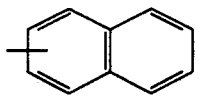

wherein the straight line represents an alkyl group and wherein the point of attachment of the naphthylalkyl radical to the remaining portion of the molecule represented by formula I is through the alkyl portion of the naphthylalkyl radical.

As used herein the term "heteromonocyclic" embraces monocyclic saturated, partially unsaturated and fully unsaturated hydrocarbon radicals having 5 or 6 ring carbon atoms wherein 1 or 2 of the ring carbon atoms are replaced by nitrogen, oxygen or sulfur. Illustrative of such radicals are pyridinyl, pyrimidinyl, thienyl, furanyl, thiazolyl, pyrazolidinyl, piperidinyl, pyrrolyl, imidazolyl, pyrazolyl, pyrazinyl, pyranyl, and thiophenyl. Attachment of the heteromonocyclic radical to the remaining portion of the molecule represented by formula I may be through a ring carbon atom of the heteromonocyclic radical or the heteromonocyclic radical may be attached through a substituent of the heteromonocyclic ring.

As used herein the term "fused bicyclic" embraces fused bicyclic ring structures having 10 to 12 ring carbon atoms wherein 1 to 3 of the ring carbon atoms may be replaced by nitrogen, oxygen or sulfur and wherein each ring of the fused bicyclic ring structure is selected from saturated, partially unsaturated, and fully unsaturated rings. Illustrative of such radicals are benzodioxolyl, benzothiophenyl, indolyl, isoindolyl, benzofuranyl, quinolinyl, isoquinolinyl, indolinyl, chromanyl and isochromanyl.

Attachment of the fused bicyclic radical to the remaining portion of the molecule represented by Formula I may be through a ring carbon atom of the fused bicyclic radical or the fused bicyclic radical may be attached through a substituent of the fused bicyclic radical for example, through the methylene substituent of the benzothiophenemethyl moiety.

As used herein the term "fused bicyclic alkyl" embraces a fused bicyclic radical which is substituted by an alkyl group having 1 to 6 carbon atoms. Attachment of the "fused bicyclic alkyl" radical to the remaining portion of the molecule represented by Formula I is through the alkyl portion of the fused bicyclic alkyl radical.

As used herein the term "phenylalkyl" embraces a phenyl radical which is substituted by an alkyl group. Attachment of the phenylalkyl radical to the remaining portion of the molecule represented by Formula I is through the alkyl portion of the phenylalkyl radical.

The compounds as shown in Formula I can exist in various isomeric forms and all such isomeric forms are meant to be included. Tautomeric forms are also included as well as pharmaceutically acceptable salts of such isomers and tautomers.

In the structures and formulas herein, the bond drawn across a bond of an aromatic ring can be to any available atom on the aromatic ring.

The term "pharmaceutically acceptable salt" refers to a salt prepared by contacting a compound of Formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

DETAILED DESCRIPTION OF THE INVENTION

The compounds of the present invention can be prepared by methods analogous to solution phase peptide synthesis [see: The Peptides: Analysis, Synthesis, Biology (E. Gross and J. Meierhofer, eds.), Vol. 1-5, Academic Press, New York)] combined with standard synthetic methods. Two general synthetic sequences to the compounds of the present invention are outlined in Schemes A and B. In the first sequence (Scheme A), an appropriately substituted benzonitrile acid is coupled to the appropriately substituted beta amino acid using standard coupling reagents, e.g. disuccinimidyl carbonate (DSC). The cyano group is converted to the amidine via the thioimidate in nearly quantitative yield. The thioimidate is formed by first treating the cyano compound with hydrogen sulfide ($H_2S$) followed by alkylation with methyl iodide. Next, treatment of the thioimidate with ammonium acetate affords the amidine as the salt (HI). The final compounds are obtained by purification by reverse phase high pressure liquid chromatography [High Performance Liquid Chromatography Protein and Peptide Chemistry (F. Lottspeich, A. Henscher, K. P. Hupe, eds.) Walter DeGruyter, New York, 1981]. In an alternative sequence (Scheme B), an appropriately substituted benzonitrile is converted to the benzamidine using lithium bis(trimethylsilyl)amide in ether-hexane solvent mixture [R. T. Boere, R. T. Oakley, R. W. Reed J. Organomet. Chem. 331(2), 161–167 (1987)]. The resultant benzamidine acid is coupled using standard coupling reagents, e.g. disuccinimidyl carbonate (DSC) or benzotriazol-1-yl-oxytris(dimethylamino)phosphonium hexafluorophosphate (BOP) to the appropriately substituted beta amino acid which affords the compounds of the present invention in a direct manner. Both sequences afford the compounds of the present invention in good overall yield.

The preparation of the appropriately substituted benzonitrile acid for use in Schemes A or B is shown in Schemes C-I. The preparation of the benzonitrile acid where Y=alkyl is shown in Scheme C. The halobenzonitrile is coupled to an omega alkenoic acid using a palladium (0) based coupling reaction ["Heck Reaction"—Palladium Reagents in Organic Syntheses (Richard F. Heck), Academic Press, New York, 1985]. The conditions for the alkenoic acid coupling component utilized the phase transfer conditions of Jeffery and Larock [T. Jeffery J. Chem. Soc. Chem. Commun. 1287-89 (1984); R. C. Larock Tetrahedron Lett. 2603-2606 (1989)]. These conditions [phase transfer agent-tetrabutylammonium salt, catalyst-palladium (II) acetate, base-potassium acetate, solvent-dimethyl formamide] are extremely mild conditions which afford a good yield of coupled olefin. The double bond is selectively reduced in the presence of the nitrile by catalytic reduction over palladium on calcium carbonate. The required omega alkenoic acids are either commercially available or can be synthesized by oxidation of the omega alkenols [E. J. Corey and G. Schmidt Tetrahedron Lett. 399 (1979)].

The preparation of the benzonitrile acid where Y=alkynyl having 2-6 carbon atoms is shown in Scheme D. The preferred conditions for the alkynoic acid coupling component utilized tetrakis(triphenylphosphine)-palladium (0) as catalyst and piperidine as the solvent [for related conditions see: H. A. Dieck and F. R. Heck J. Organometallic Chem. 259-263 (1975)].

The preparation of the benzonitrile acid where Y=-carbonylalkyl having 2 to 6 carbon atoms is shown in Schemes E-G. An example of a carbonylalkyl wherein the carbonyl is in the homobenzylic position is shown in Scheme E. The halobenzonitrile is coupled to an omega alkynoic acid using a palladium (0) based coupling reaction under the above stated phase transfer conditions of Jeffery and Larock [T. Jeffery J. Chem. Soc. Chem. Commun. 1287-89(1984); R. C. Larock Tetrahedron Lett. 2603-2606 (1989)] which spontaneously lactonizes as shown. The enol lactone is hydrolyzed with base (sodium hydroxide). Alternatively, the enol lactone can be formed starting from p-(cyanophenyl) pentynoic acid as shown in Scheme E.

An example of a carbonylalkyl wherein the carbonyl is in the benzylic position is shown in Scheme F. The commercially available ethyl 2-(4-cyanobenzoyl)acetate undergoes a Michael reaction catalyzed by nickel acetylacetonate [Ni(acac)$_2$] as shown [J. H. Nelson, P. N. Howells, G. D. DeLullo, and G. L. Landen J. Org. Chem. 1246 (1980)]. Deprotection and decarboxylation is accomplished in one step using lithium chloride in dimethyl sulfoxide [A. B. Holmes, C. Swithenbank, S. F. Williams J. Chem. Soc., Chem. Commun. 265 (1986)].

An example of a carbonylalkyl wherein the carbonyl is displaced from the benzonitrile by two methylenes is shown in Scheme G. A Horner-Wadsworth-Emmons reaction [For Reviews see: Wadsworth Org Reactions 25, 73-253 (1977); Boutagy and Thomas Chem Rev. 87-99 (1974)] affords the alpha, beta unsaturated Weinreb amide [J. M. Nuzillard, A. Boumendjel, G. Massiot Tetrahedron Lett. 3779 (1989)] using commercially available reagents. After reduction the Weinreb amide is converted to the ketone by reaction with the appropriate alkyl lithium or Grignard reagent [S. Nahm, S. M. Weinreb Tetrahedron Lett. 3815 (1981)]. Hydrogenolysis is followed by Jones oxidation [Bowers, Halsall, Jones, and Lemin J. Chem. Soc. 2548 (1953)] to afford the appropriate substituted benzonitrile acid.

All of the benzonitrile acids where Y=carbonylalkyl having 2 to 6 carbon atoms as described in Schemes E-G can be converted to alkenyl substituted or alkyl substituted Y=alkyl derivatives as shown in Scheme H. The alkenyl substituted derivatives are prepared via a Wittig reaction [For a recent review see: B. E. Maryanoff, A. B. Reitz Chem. Rev. 863 (1989)] or its equivalent. Occasionally in dealing with highly enolizable ketones it is necessary to use less basic reagents such as the Lombard Reagent [L. Lombard Tetrahedron Lett. 4293 (1982); J. Hibino, T. Okazoe, K. Takai, H. Nozaki Tetrahedron Lett. 5579 (1985)]. The alkenyl substituted derivatives can be converted to the alkyl substituted derivatives by hydrogenation over palladium on calcium carbonate as shown. Alternatively, when dealing with highly enolizable ketones, the organocerium reagent [T. Imamoto, N. Takiyama, and K. Nakamura Tetrahedron Lett. 4763 (1985); T. Imamoto, Y. Sugiura, and N. Takiyama Tetrahedron Lett. 4233 (1984); T. Imamoto, T. Kusumoto, Y. Tawarayama, Y. Sugiura, T. Mita, Y. Hatanaka, and M. Yokoyama J. Org. Chem. 3904 (1984)] can be added to the ketone followed by hydroxyl removal [xanthate formation followed by radical reduction tributyltin hydride (Bu$_3$SnH) and (AIBN)] [S. Inokawa, T. Mitsuyoshi, H. Kawamoto, H. Yamamoto, M. Yamashita Carbohyd. Res. 142 (2), 321 (1985)].

The substituents, R$_5$ and R$_6$=halogen, alkyl, hydroxy, or alkoxy, can be introduced where Y=alkyl at the benzonitrile stage (e.g. compound 4, Scheme L) using bromine, iodine, or chlorine to halogenate the ring (Scheme I). The alkyl group can be introduced by low temperature lithium halogen exchange followed by quenching with the appropriate aldehyde [see: W. E. Parham, C. K. Bradsher Acct. Chem. Res. 300 (1982)]. The resultant alcohol can be converted to R$_5$ or R$_6$=alkyl by hydrogenolysis [Reductions in Organic Chemistry (M. Hudlicky, ed.), John Wiley & Sons, New York, 1984] as shown in Scheme I. The substituents, R$_5$ or R$_6$=hydroxy or alkoxy, can be introduced by low temperature lithium halogen exchange followed by quenching with the electrophilic bis(trimethylsilyl) peroxide [(TMSO)$_2$—Scheme E) M. Taddei and A. Ricci Synthesis 633-635 (1986)] which affords the silyl ether. The silyl ether can be converted to the R$_5$ or R$_6$=OH by treatment with hydrochloric acid [M. Taddei and A. Ricci ibid]. The R$_5$ or R$_6$=OR can be formed by treating the derivative where R$_5$ or R$_6$=OH with weak base (K$_2$CO$_3$) and an appropriate alkyl halide [R$_8$—Hal, 2 equivalents, see: C. F. H. Allen and J. W. Gates, Jr. Organic Syntheses Coll. Vol. 3 140 (1955)] which will form the ester as well. The ester can be selectively cleaved in the presence of the ether with one equivalent of sodium hydroxide (Scheme I). Potentially, the disubstituted derivatives are available from the corresponding dihalo compounds obtained from the initial reaction of Scheme I by carrying out the above described steps.

The appropriately substituted beta amino acids can be either purchased or prepared from commercially available starting materials using known methods as illustrated in Scheme J. The racemic beta aryl beta amino acids can be prepared from the appropriate aryl aldehyde, malonic acid, and ammonium acetate as shown in Scheme J—method 1 (Johnson and Livak J. Am. Chem. Soc. 299(1936)]. The racemic beta alkyl beta amino acids can be prepared from the corresponding alkene and chlorosulfonyl isocyanate which goes through the beta lactam intermediate as shown in Scheme J—method 2 [W. A. Szabo Aldrichimica Acta 23 (1977); R. Graf Angew, Chem. Internat. Edit. 172 (1968)]. The beta lactam can be opened to the ethyl ester by treatment with anhydrous hydrochloric acid in ethanol as shown Scheme J. The racemic beta amino acids can be resolved using classical methods as described in the literature [E. Fischer, H. Scheibler, R. Groh Ber. 2020 (1910); E. Fischer, H. Scheibler Annalen 337 (1911)]. Enamtionmerically pure beta amino acids can be prepared using many different approaches including the following methods: homologation of the alpha amino acids using an Arndt-Eistert reaction as shown in Scheme J method 3 [Meier and Zeller *Angew. Chem. Int. Ed. Eng.* 32-43 (1975); M. Rodriguez et al *Tetrahedron Lett.* 5153 (1990); W. J. Greenlee *J. Med. Chem.* 434 (1985) and references therein]; from enamtionmerically pure precursors obtained from enamtionmerically pure aspartic acid [i.e. Scheme J method 4, see: Asymmetric Synthesis: Construction of Chiral Molecules Using Amino Acids (G. M. Coppola and H. F. Schuster, eds.), pg 209-212, John Wiley, New York]; through the addition of amines to alpha, beta unsaturated esters bearing an enamtionmerically pure auxiliary as shown in Scheme J method 5 [J. d'Angelo and J. Maddaluno *J. Am. Chem. Soc.* 8112-14 (1986)]; through an enantioselective hydrogenation of a dehydroamino acid as shown in Scheme J method 6 [see: Asymmetric Synthesis, Vol. 5, (J. D. Morrison, ed.) Academic Press, New York, 1985]; and through the Michael addition of a chiral N-benzylalpha-phenethylamine to an appropriately substituted alpha, beta unsaturated ester as shown in Scheme J method 7 [S. G. Davies and O. Ichihara *Tetrahedron Asymmetry* 183 (1991)].

A specific synthesis of compound 9 using Method A as described in a general sense in Scheme A is shown in Scheme K. The compound numbers correspond to the compound numbers in example 1. Examples 2-11 were prepared using the method of example 1 with the specific changes as stated in each example, and in the general manner described in Scheme A. A specific synthesis of compound 15 using Method B as described in a general sense in Scheme B with disuccinimidyl carbonate (DSC) as the coupling agent is shown in Scheme L. The compound numbers correspond to the compound numbers in examples 17 and 18. A specific synthesis of compound 19 using Method B as described in a general sense in Scheme B with benzotriazol-1-yl-oxytris(dimethylamino)phosphonium hexafluorophosphate (BOP) as the coupling agent is shown in Scheme M. The compound numbers correspond to the compound numbers in examples 19 and 20.

Scheme A - Method A

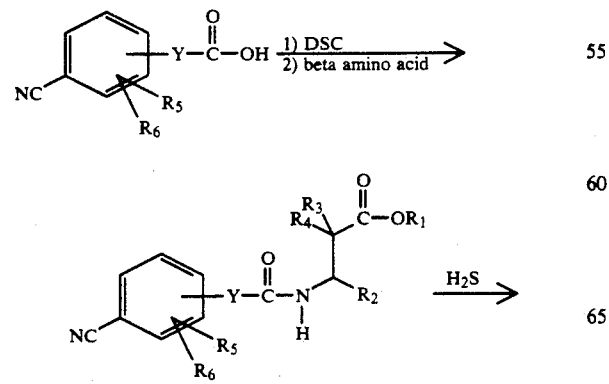

Scheme A - Method A

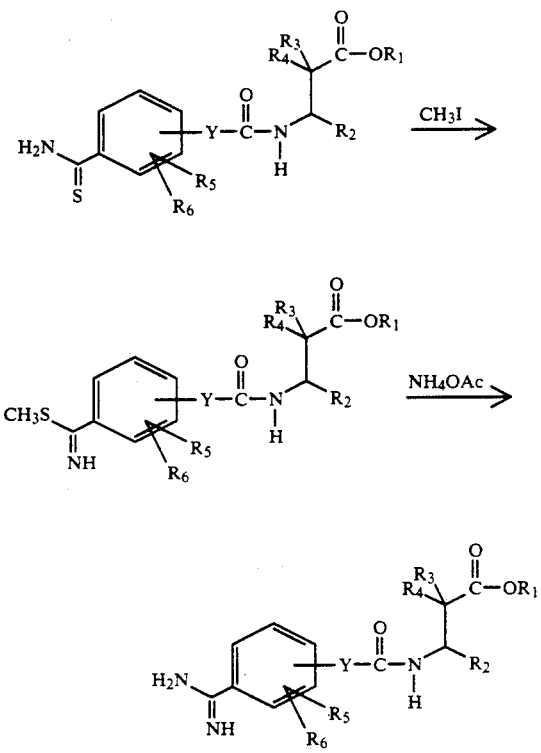

$R_1$, $R_2$, $R_3$, $R_4$, $R_5$ and $R_6$ are defined as before.

Scheme B - Method B

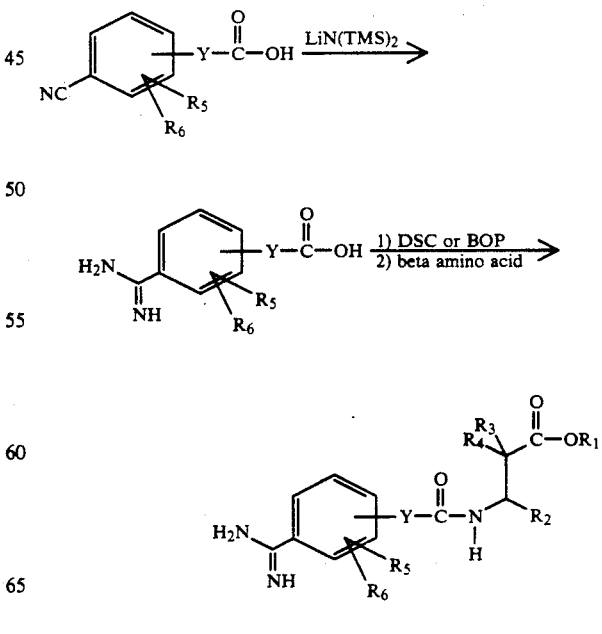

$R_1$, $R_2$, $R_3$, $R_4$, $R_5$ and $R_6$ are defined as before.

Scheme C
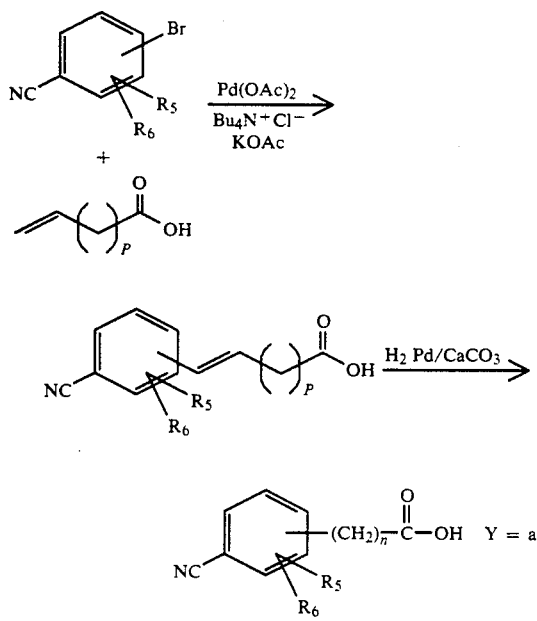
$R_5$ and $R_6$ are defined as before.
n=1 to 5
p=0 to 3
Scheme D
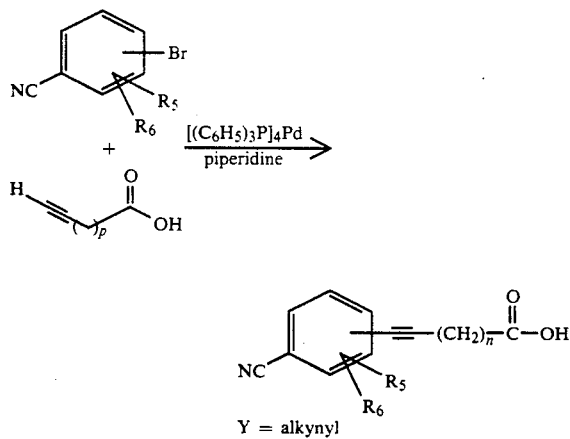
$R_5$ and $R_6$ are defined as before.
n=1 to 3
p=0 to 3
Scheme E
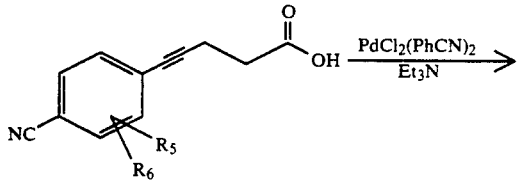
-continued
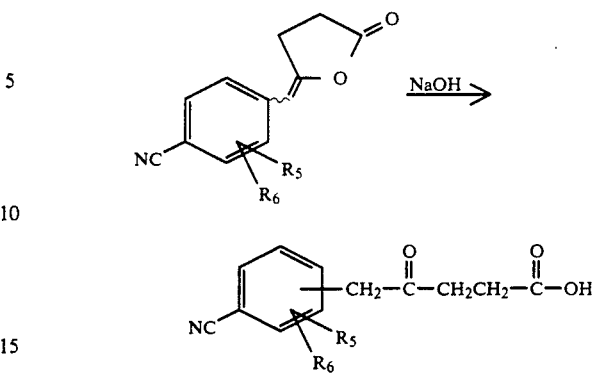
Scheme F
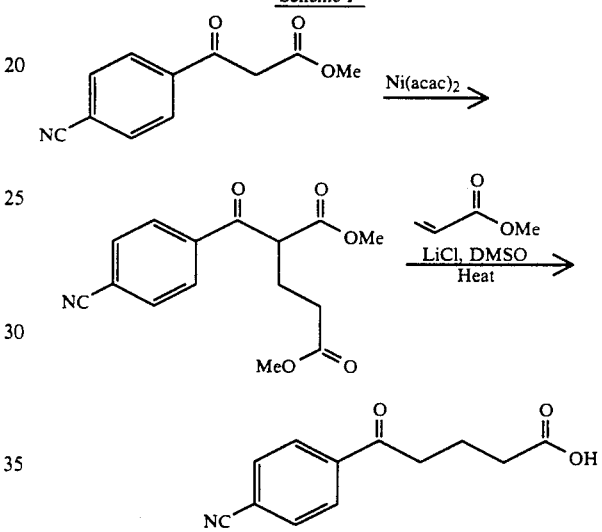
$R_5$ and $R_6$ are defined as before.
Scheme G
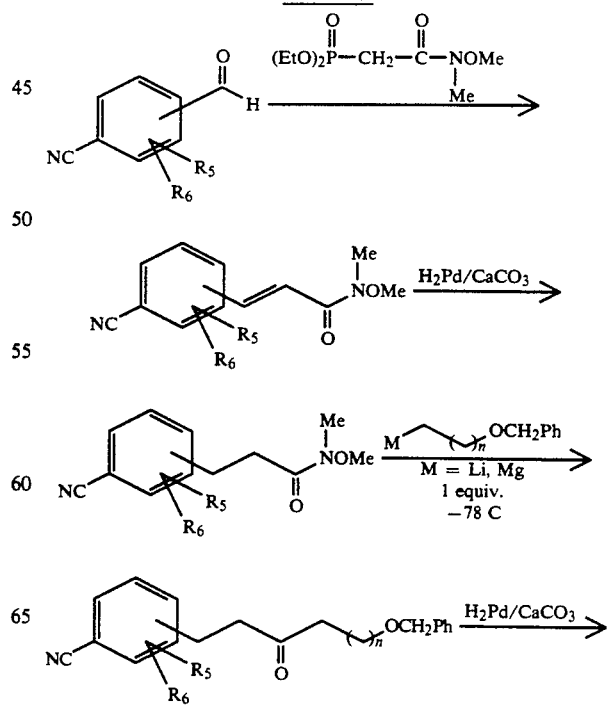

21
-continued
Scheme G
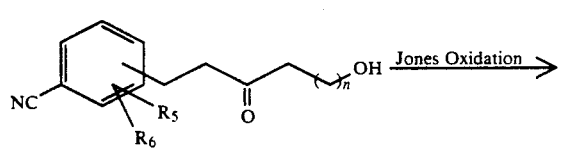
22
-continued
Scheme G
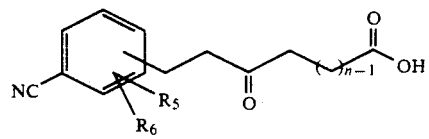
$R_5$ and $R_6$ are defined as before.
n=1 to 2
Scheme H
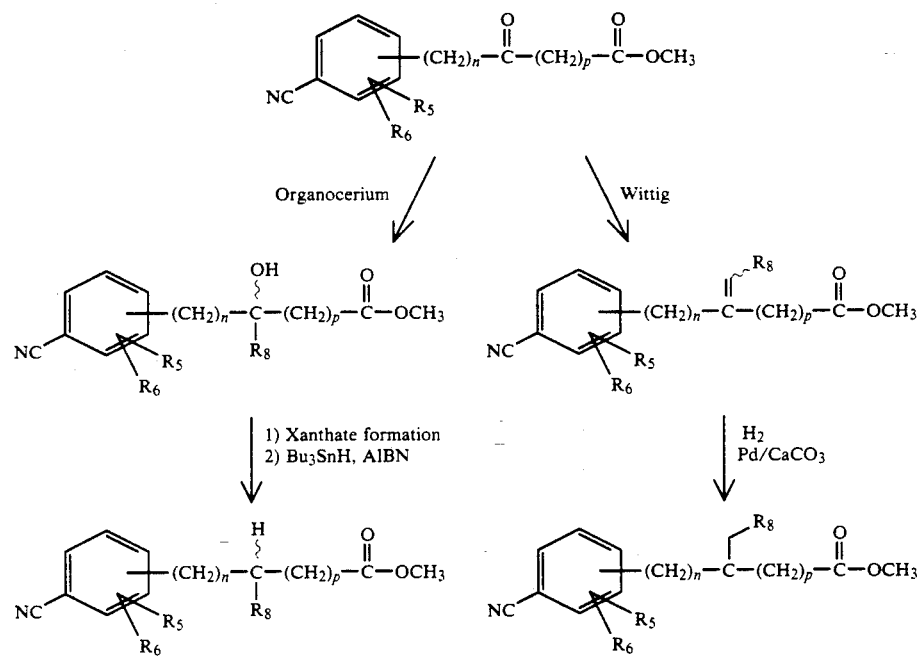
$R_5$ and $R_6$ are defined as before.
n=1 to 4
p=0 to 4
p=0 to 4
$R_8$=alkyl, alkenyl, alkoxy or phenyl
Scheme I
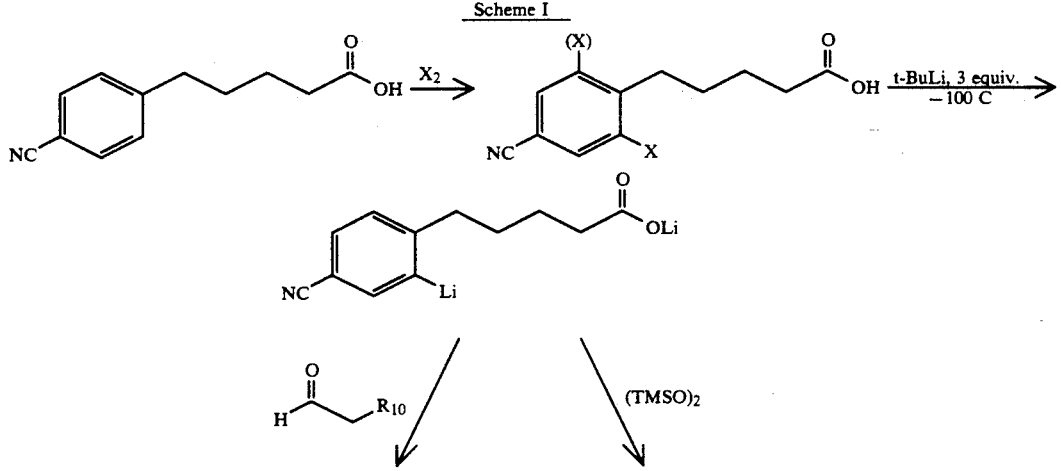

5,220,050

23

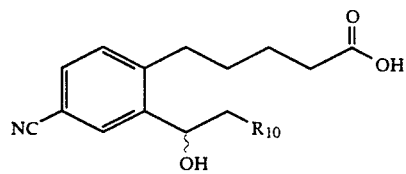

↓ H₂
Pd/CaCO₃

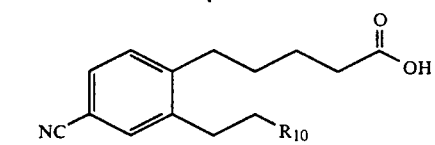

-continued
Scheme I

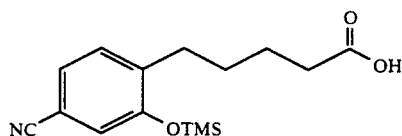

↓ 1) HCl
2) R₉—Hal, K₂CO₃
3) NaOH

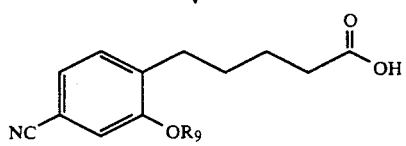

R₉ = alkyl
R₁₀ = hydrido or alkyl

Scheme J

Method 1

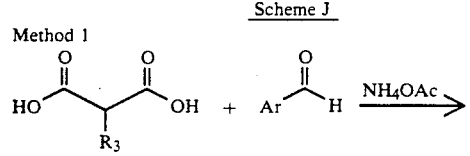 NH₄OAc⟶

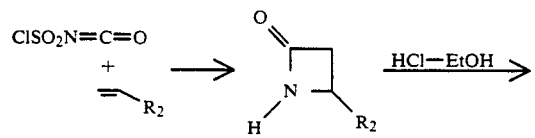

Method 2

ClSO₂N=C=O +
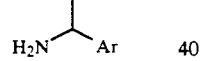 ⟶ 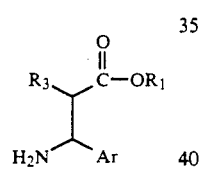 HCl—EtOH⟶

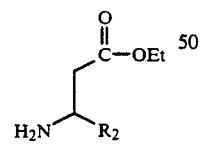

Method 3

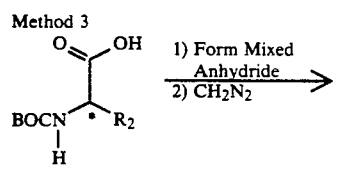 1) Form Mixed Anhydride
2) CH₂N₂ ⟶

*Indicates Chiral Center

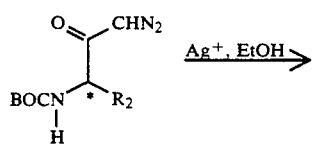 Ag⁺, EtOH⟶

24

-continued
Scheme J

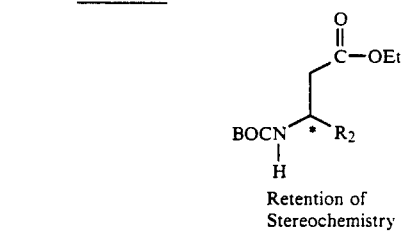

Retention of Stereochemistry

Method 4

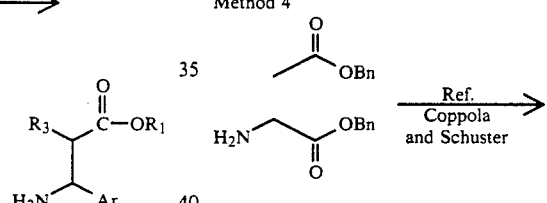
Ref. Coppola and Schuster ⟶

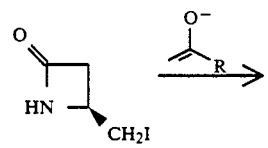

Method 5

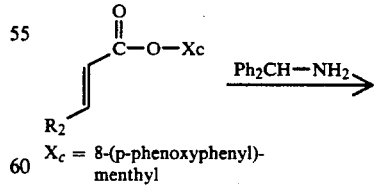 Ph₂CH—NH₂⟶

X_c = 8-(p-phenoxyphenyl)-menthyl

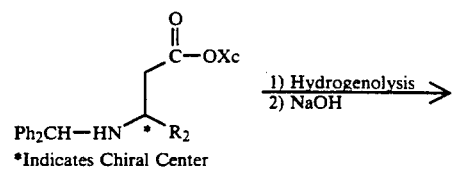 1) Hydrogenolysis
2) NaOH ⟶

*Indicates Chiral Center

-continued
Scheme J
Method 6
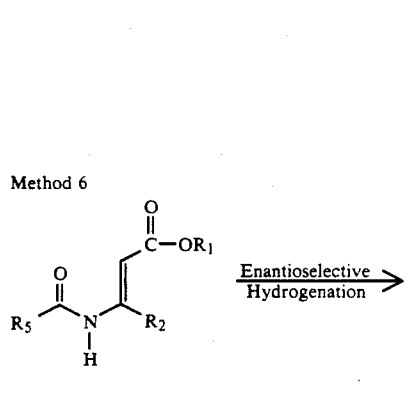
Method 7
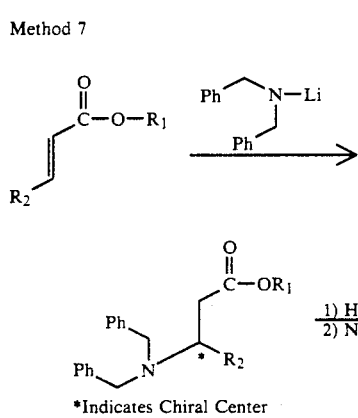
*Indicates Chiral Center
Scheme K
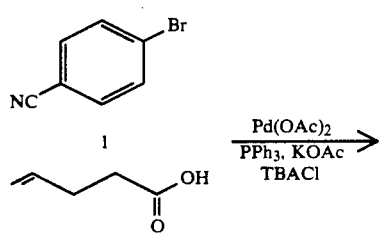
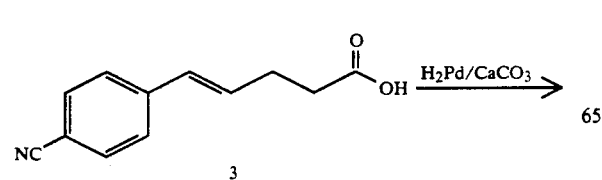
-continued
Scheme K
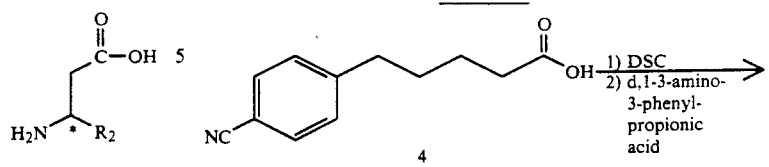
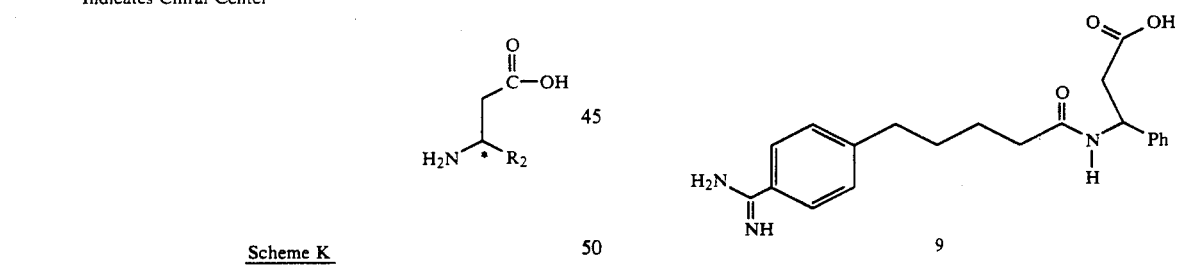
Scheme L
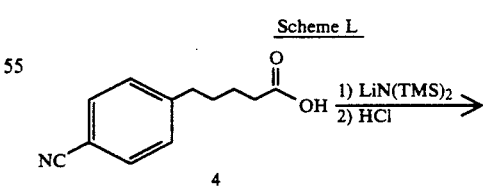
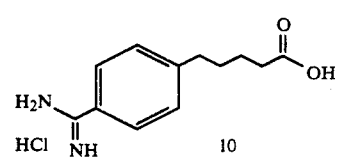

-continued
Scheme L

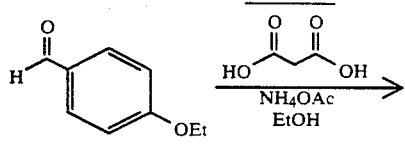

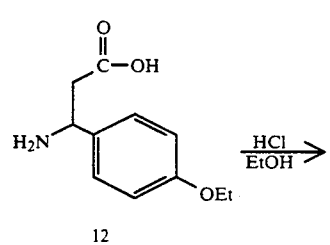

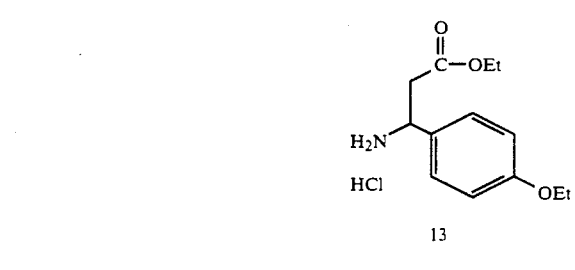

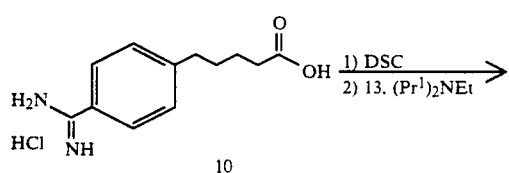

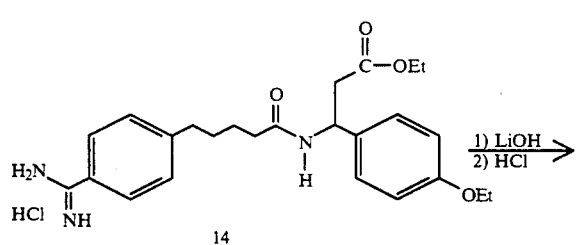

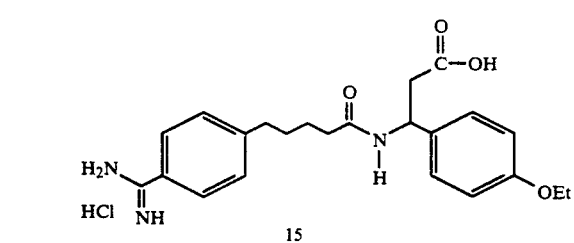

Scheme M

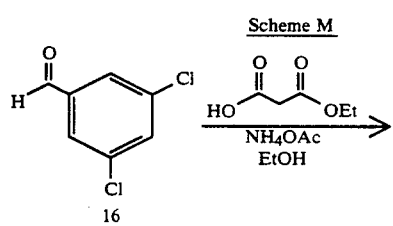

-continued
Scheme M

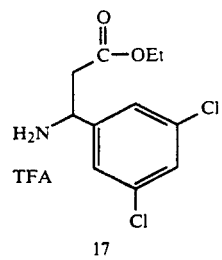

This invention also relates to a method of inhibiting platelet aggregation and more specifically, a method of treatment involving the administration of compounds of Formula I to achieve such inhibition.

For the inhibition of platelet aggregation, compounds of Formula I may be administered orally, parenterally, or by inhalation spray or rectally in dosage unit formulations containing conventional non-toxic pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight sex and medical condition of the patient; the severity of the condition; the route of administration; and the particular compound employed. Thus dosage regimen may vary widely. Dosage levels of the order from about 0.01 mg to about 150 mg per kilogram of body weight per day are useful in the treatment of the above-indicated conditions (from about 10 mg to about 10500 mg per patient per day). For oral administration a daily dose of from about 0.01 to 150 mg/Kg body weight, particularly from about 1 to 30 mg/Kg body weight may be appropriate. For administration by injection a preferred daily dose would be from about 0.01 to 50 mg/Kg body weight.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain, for example, an amount of active ingredient from about 1 to 250 mg, preferably from about 25 to 150 mg. A suitable daily dose for a mammal may vary widely depending o the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The following Examples are intended to further illustrate the present invention and not to limit the invention in spirit or scope. In the Examples, all parts are parts by weight and temperature is in degrees Celsius unless otherwise expressly set forth.

EXAMPLE 1

A. Preparation of 5-(p-Cyanophenyl)-4-pentenoic acid

Tetrabutylammonium chloride (hydrate, 17.8 g) was dried by azeotroping with benzene (250 mL round bottom flask equipped with a Dean-Stark apparatus). The benzene was removed in vacuo affording anhydrous tetrabutylammonium chloride (17.0 g, 61.2 mmol). To this flask under argon were added triphenylphosphine (820 mg, 3.13 mmol), palladium acetate (703 mg, 3.13 mmol), 4-bromobenzonitrile (16.9 g, 92.8 mmol), potassium acetate (36.8g, 375 mmol) and 100 mL of degassed anhydrous dimethylformamide (degassed by bubbling argon through for 10 min, dried over molecular sieves). A solution of 4-pentenoic acid (6.27 g, 62.6 mmol) and degassed anhydrous DMF (35 mL) was then added to the rapidly stirring reaction mixture at 23° C. After 21 hours at 23° C, the reaction mixture was poured slowly into a sodium carbonate solution (3%, 400 mL) and extracted with ethyl acetate (500 mL). The aqueous layer was treated with decolorizing carbon, and filtered. Then, the aqueous layer was acidified to a pH of 2 with 10% HCl which afforded the title compound as a white solid (6.82 g, 54%): m.p. 150°–167° C.

The above procedure afforded the title compound (compound of Scheme D) in sufficient purity to take on to the next step without complications. An analytical sample was obtained by submitting the sample to further purification by flash chromatography (ethyl, acetate:methylene chloride:acetic acid, 1:4:0.05) and recrystallization from ethyl acetate (2 times). The resulting product had the following properties: m.p. 154°–156° C.

Anal Calcd. for $C_{12}H_{11}NO_2$: C, 71.63; H, 5.51; N, 6.96. Found: C, 71.50; H, 5.54; N, 6.80.

B. Preparation of 5-(p-Cyanophenyl)pentanoic acid

A solution of 1.47 g (7.32 mmol) of the product of A in 90 mL of methanol was hydrogenated over 200 mg of 5% Pd/CaCO$_3$ at 5 psi hydrogen over a 1.2 h period. After removing the catalyst by filtration and evaporation of the solvent in vacuo, the residue was triturated with ether followed by hexane which afforded a white solid. The resulting product had the following properties: m.p. 101°–102° C.

Anal. Calcd. for $C_{12}H_{13}NO_2$: C, 70.92; H, 6.45; N, 6.89.

Found: C, 70.71; H, 6.56; N, 6.87.

Preparation of DL-N-[5-(p-Cyanophenyl)pentanoyl]-3-phenyl-beta-alanine

To a solution of 5-(p-cyanophenyl)pentanoic acid (1.00g, 4.93 mmol), dimethylformamide (10 mL), and pyridine (2 mL) was added N,N'-disuccinimidylcarbonate (1.24 g, 4.85 mmol) and 4-dimethylaminopyridine (60 mg, 0.493 mmol) under an argon atmosphere at 23° C. After 5 h, DL-3-amino-3-phenylpropionic acid (0.814 g, 4.93 mmol) was added as a solid, followed immediately by N,N'-diisopropylethyl amine (0.627 g, 4.85 mmol). After 20 h at 23° C., the reaction mixture was concentrated in vacuo. The residue was dissolved in ethyl acetate (300 mL), washed with KHSO$_4$ (2×50 mL), washed with brine (1×50 mL), dried (Na$_2$SO$_4$), and concentrated in vacuo. The residue was purified by flash chromatography (2 liters ethyl acetate: chloroform:acetic acid 50:50:0.5 followed by 2 liters of ethyl acetate:methanol:acetic acid 89:10:1) to afford 850 mg (50%) of the title compound (compound 6 of Scheme D). The product was verified by C NMR (CDCl$_3$) delta 24.9, 29.9, 35.3, 35.7, 40.5, 49.7, 109.1, 118.9, 126.1, 127.4, 128.5, 129.0, 131.9, 140.5, 147.8, 173.4, 176.4.

D. Preparation of
β-[[5-4-(aminoiminomethyl)phenyl]-1-oxopentyl-]amino]benzenepropanoic acid, acetate salt Hydrogen sulfide was bubbled through a solution of 350 mg (1.00 mmol) of the product of step C (compound 6 of Scheme D) in pyridine:triethylamine (12 mL:1.2 mL) for 3 min at 23° C. After 24 h at 23° C. in an enclosed flask, the reaction mixture was concentrated under a steady stream of nitrogen. The residue was diluted with ethyl acetate (200 mL), washed with KHSO$_4$ (2N, 2×50 mL), brine (1×50 mL), and dried (Na$_2$SO$_4$). Concentration in vacuo afforded a 94% yield of thioamide (compound 7 of Scheme D).

Thioamide (360 mg, 0.937 mmol) was dissolved in a solution of acetone:iodomethane (14 mL:1 mL). The reaction mixture was warmed to achieve reflux for 25 min. Concentration in vacuo afforded a quantitative yield of compound 8 of Scheme D as the HI salt.

A solution of (8) (373 mg, 0.937 mmol) and ammonium acetate (108 mg, 1.40 mmol) in methanol (10 mL) was warmed to achieve reflux for 3.5 h. After cooling to 23° C., the reaction mixture was concentrated under a steady stream of nitrogen in the hood which afforded a quantitative yield of compound 9 of Scheme D. The product was purified on a reverse-phase C-18 functionalized column (1.9 cm×15 cm) using a linear gradient of 10% methanol/water 0.5% acetic acid to 100% methanol (40 min) with a flow rate of 3 mL per min to afford the title compound (compound 9 of Scheme D). The product purity was verified by C NMR (CD$_3$OD) delta 25.0, 30.0, 34.9, 35.3, 40.2, 50.1, 125.4, 126.2, 127.1, 127.6, 128.2, 129.1, 141.5, 149.5, 166.9, 172.8, 173.8.

Anal Calcd. for C$_{21}$H$_{25}$N$_3$O$_3$ plus 0.6 H$_2$O and 0.7 acetic acid: C, 64.01; H, 6.95; N, 10.00. Found: C, 63.83; H, 6.58; N, 10.20.

EXAMPLE 2

Preparation of Ethyl β-[[5-[4-(aminoiminomethyl)phenyl]-1-oxopentyl-]amino]benzenepropanoate

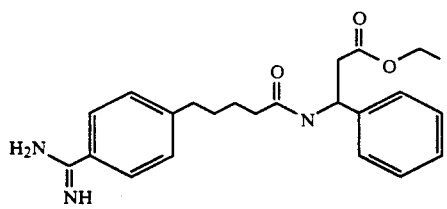

The product of Example ID (compound 9 of Scheme D) was esterified in neat ethanol saturated with HCl gas to afford the title compound in a quantitative yield. The product was purified on a reverse-phase C-18 functionalized column (5 cm×30 cm) using a linear gradient of 5% acetonitrile/water 0.05% trifluoroacetic acid to 40% acetonitrile/water 0.05% trifluoroacetic acid (30 min) with a flow rate of 80 mL/per min to afford the title compound. The product was verified by C NMR (CD$_3$OD) delta 12.6, 24.4, 29.4, 34.4, 34.7, 39.9, 49.4,59.8, 125.5, 125.6, 126.6, 126.9, 127.6, 128.5, 140.6, 148.8, 167.1, 170.2, 173.0; chemical ionization mass spectrometry (MH$^+$=396)

Anal. Calcd. for C$_{23}$H$_{29}$N$_3$O$_3$ plus 0.5 CF$_3$CO$_2$H and 1.0 H$_2$O: C, 61.26; H, 6.75; N, 8.93. Found: C, 61.03; H, 6.67; N, 9.15.

EXAMPLE 3

Preparation of 3-[[5-[4-(Aminoiminomethyl)phenyl]-1-oxopentyl-]amino]butanoic acid

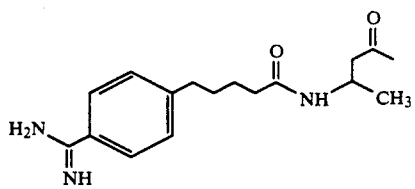

The title compound was prepared in the manner of example 1 with the following modifications: Substituting 3-methyl-beta-alanine for 3-phenyl-beta-alanine. The product was purified on a reverse-phase C-18 functionalized column (5 cm×30 cm) using a linear gradient of 5% acetonitrile/water 0.05% trifluoroacetic acid to 40% acetonitrile/water 0.05% trifluoroacetic acid (30 min) with a flow rate of 80 mL/per min to afford the title compound. The product was verified by C NMR (CD$_3$OD) delta 19.7, 25.7, 30.7, 35.6, 36.0, 40.8, 42.9, 126.6, 128.2, 129.7, 150.1, 167.3, 174.1, 174.4; fast atom bombardment mass spectrometry (MH$^+$=306).

Anal. Calcd. for C$_{16}$H$_{23}$N$_3$O$_3$ plus 0.3 H$_2$O and 1.0 CF$_3$CO$_2$H: C, 50.89; H, 5.84; N, 9.89. Found: C, 50.58; H, 5.60; N, 9.70.

EXAMPLE 4

Preparation of Ethyl 3-[[5-[4-(aminoiminomethyl)phenyl]-1-oxopentyl-]amino]butanoate

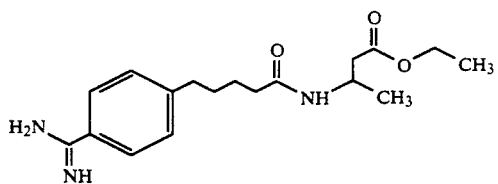

The compound of Example 3 was esterified in neat ethanol saturated with HCl gas to afford the title compound in a quantitative yield. The product was verified by C NMR (CD$_3$OD) delta 14.1, 19.7, 26.2, 30.8, 35.3, 35.7, 40.6, 44.4, 61.1, 126.1, 128.6, 130.0, 150.2, 167.3, 171.7, 176.0; chemical ionization mass spectrometry (MH$^+$=335).

EXAMPLE 5

Preparation of β-[[5-[4-(Aminoiminomethyl)phenyl)-1-oxopentyl-]amino][1,1'-biphenyl]-4-propanoic acid, acetate salt

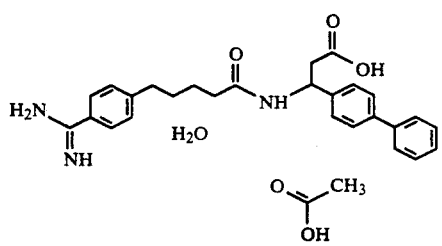

The title compound was prepared in the manner of example 1 with the following changes in procedure A: substitution of 3-(4-biphenyl)-beta-alanine for 3-phenyl-beta-alanine. The final product was verified by C NMR (CD3OD) delta 25.1, 30.0, 35.0, 35.3, 40.1, 49.8, 125.4, 126.5, 126.7, 127.0, 127.5, 127.6, 128.5, 129.0, 140.2, 140.5, 140.7, 149.5, 166.9, 172.7, 173.7.

Anal. Calcd. for C27H29N3O3 plus 1.0 H2O and 1.0 CH3CO2H: C, 66.78; H, 6.76; N, 8.06. Found: C, 67.15; H, 6.45; N, 8.17.

EXAMPLE 6

Preparation of
N-[5-[4-(Aminoiminomethyl)phenyl]-1-oxopentyl]-2-hydroxy-β-alanine

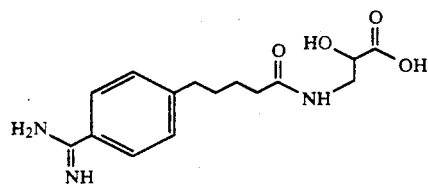

The title compound was prepared in the manner of example 1 substituting 2-hydroxy-beta-alanine for 3-phenyl-beta-alanine. The product was purified on a reverse-phase C-18 functionalized column (5 cm×30 cm) using a linear gradient of 5% acetonitrile/water 0.05% trifluoroacetic acid to 40% acetonitrile/water 0.05% trifluoroacetic acid (30 min) with a flow rate of 80 mL/per min to afford the title compound. The product was verified by C NMR (CD3OD) delta 24.5, 25.6, 30.5, 30.7, 33.6, 35.6, 35.7, 40.1, 71.6, 126.1, 128.2, 129.7, 150.2, 167.2, 173.5, 176.0; chemical ionization mass spectrometry (MH+ =290).

EXAMPLE 7

Preparation of
N-[5-[4-(Aminoiminomethyl)phenyl]-1-oxopentyl]-β-alanine, phenylmethyl ester

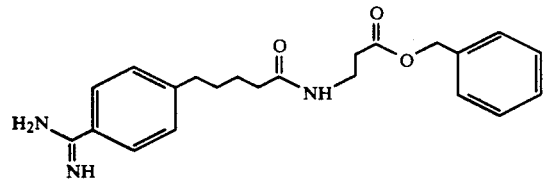

The title compound was prepared in the manner of example 1 substituting beta-alanine benzyl ester for 3-phenyl-beta-alanine. The product was purified on a reverse-phase C-18 functionalized column (5 cm×30 cm) using a linear gradient of 5% acetonitrile/water 0.05% trifluoroacetic acid to 40% acetonitrile/water 0.05% trifluoroacetic acid (30 min) with a flow rate of 80 mL/per min to afford the title compound. The product was verified by C NMR (CD3CO2D) delta 24.2, 29.2, 32.7, 34.2, 34.4, 65.6, 124.3, 127.0, 127.1, 127.3, 127.6, 128.4, 135.0, 148.9, 165.6, 171.8, 174.8; chemical ionization mass spectrometry (MH+ =382).

Anal. Calcd. for C22H27N3O3 plus 1.0 CF3CO2H: C, 58.18; H, 5.70; N, 8.48. Found: C, 57.80; H, 5.75; N, 8.39.

EXAMPLE 8

Preparation of
N-[5-[4-(Aminoiminomethyl)phenyl]-1-oxopentyl]-2-fluoro-β-alanine

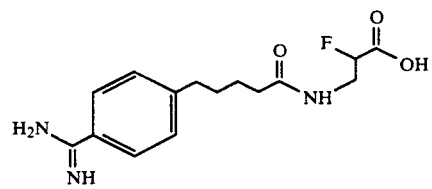

The title compound was prepared in the manner of example 1 substituting 2-fluoro-beta-alanine for 3-phenyl-beta-alanine. The product was purified on a reverse-phase C-18 functionalized column (5 cm×30 cm) using a linear gradient of 5% acetonitrile/water 0.05% trifluoroacetic acid to 40% acetonitrile/water 0.05% trifluoroacetic acid (30 min) with a flow rate of 80 mL/per min to afford the title compound. The product purity was verified by C NMR (CD3CO2D) delta 26.1, 31.1, 36.2, 36.3, 41.7, 41.9, 87.2, 89.0, 126.4, 128.9, 130.3, 150.7, 167.4, 177.0, 177.4; fast atom bombardment mass spectrometry (M-17=273).

EXAMPLE 9

Preparation of
β-[5-[4-(Aminoiminomethyl)phenyl]-1-oxopentyl]amino]benzenebutanoic acid

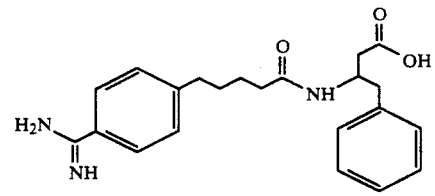

The title compound was prepared in the manner of example 1 substituting 3-benzyl-beta-alanine (3-amino-4-phenylbutyric acid) for 3-phenyl-beta-alanine. The product was purified on a reverse-phase C-18 functionalized column (5 cm×30 cm) using a linear gradient of 5% acetonitrile/water 0.05% trifluoroacetic acid to 40% acetonitrile water 0.05% trifluoroacetic acid (30 min) with a flow rate of 80 mL/per min to afford the title compound. The product was verified by C NMR (CD3OD) delta 25.5, 30.4, 35.5, 35.9, 38.8, 40.4, 48.4, 126.1, 126.7, 128.1, 128.6, 129.5, 129.7, 138.7, 150.1, 167.6, 174.0, 174.5; chemical ionization mass spectrometry (MH+ =382).

Anal Calcd. for C22H27N3O3 plus 1.1 H2O and 1.0 CF3CO2H: C, 55.94; H, 5.91; N, 8.15. Found: C, 55.69; H, 5.52; N, 7.89.

EXAMPLE 10

Preparation of N-[5-[4 (aminoiminomethyl)phenyl]-1-oxopentyl]-β-alanine

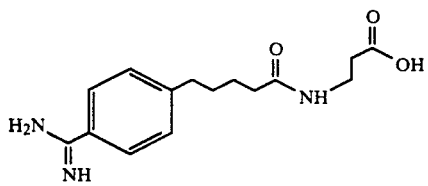

A solution of 280 mg (0.735 mmol) of the final product of Example 7 in 10 mL of ethanol was hydrogenated over 280 mg of 10% Pd/C under a balloon atmosphere of hydrogen over a 20 h period. Filtration and evaporation of the solvent in vacuo afforded 180 mg (85%) of the title compound in a pure form. The product was verified by C NMR (CD$_3$OD) delta 25.5, 30.6, 33.9, 35.4, 35.5, 35.7, 126.0, 128.1, 129.5, 149.9, 166.9, 174.3, 174.9; chemical ionization mass spectrometry (MH$^+$ = 292).

Anal. Calcd. for C$_{15}$H$_{21}$N$_3$O$_3$ plus 1.3 H$_2$O and 1.0 CF$_3$CO$_2$H: C, 47.62; H, 5.78; N, 9.80. Found: C, 47.90; H, 5.25; N, 9.42.

EXAMPLE 11

A. Preparation of 5-(p-cyanophenyl)-4-pentynoic acid

A solution of 4-pentynoic acid (2.15 g, 22 mmol), 4-bromobenzonitrile (3.64 g, 20 mmol) and piperidine (40 mL) was degassed by bubbling nitrogen through the solution for 5 min prior to the addition of tetrakis(triphenylphosphine) palladium (0) (240 mg, 0.2 mmol). The reaction vial was sealed and warmed to 80° C. for 1.5 h. After cooling to 23° C., the reaction mixture was diluted with ethyl acetate (200 mL), filtered, and concentrated in vacuo. The residue was diluted with ethyl acetate (300 mL), washed with 5% HCl (2×100 mL), washed with water (1×100 mL), and extracted with 3% sodium carbonate (2×200 mL). The basic aqueous layer was treated with decolorizing carbon, filtered, and acidified to pH=2. The resultant solid was filtered, washed with water, dried, and purified by flash chromatography (gradient ethyl acetate:methylene chloride:acetic acid 1:9:0.005) and fractional recrystallization (methylene chloride-ether) to afford the title compound as a white solid: m.p. 149°-152° C.

Anal. Calcd. for C$_{12}$H$_9$NO$_2$ C, 72.35; H, 4.55; N, 7.03.

Found: C, 72.05; H, 4.57; N, 6.94.

B. Preparation of β-[[5-[4-(aminoiminomethyl)phenyl]-1-oxo-4-pentynyl]amino]benzenepropanoic acid

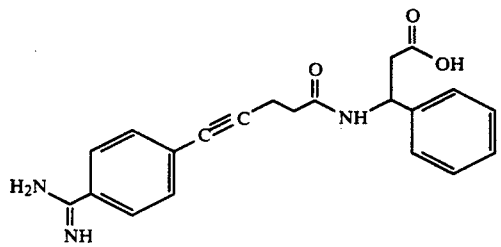

The title compound was prepared in the manner of example 1 with the following modifications: Substituting 5-(p-cyanophenyl)-4-pentynoic acid for 5-(p-cyanophenyl)pentanoic acid in procedure C of example 1. The product was verified by C NMR (CD$_3$OD) delta 16.6, 35.4, 42.2. 50.8. 80.9, 95.1, 127.7, 128.2. 128.5, 129.5, 129.5, 129.7, 132.8, 143.7, 166.5, 170.8, 172.9.

Anal. Calcd. for C$_{21}$H$_{21}$N$_3$O$_3$ plus 0.5 H$_2$O and 1.0 CF$_3$CO$_2$H: C, 56.79; H, 4.77; N, 8.64. Found: C, 56.91; H, 4.68; N, 8.55.

EXAMPLE 12

Preparation of β-[[5-[4-(aminoiminomethyl]phenyl]-1-oxopentyl]amino]benzenepentanoic acid

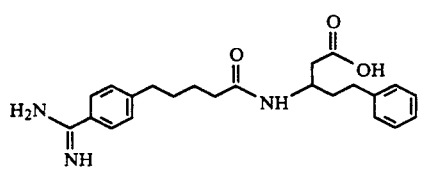

Chlorosulfonyl isocyanate (7.2 mL, 11.7 g, 82.7 mmol) was added to 4-phenyl-1-butene (11.1 g, 84.0 mmol) under a nitrogen atmosphere at 23° C. After 40 h, the reaction mixture was added dropwise to a rapidly stirring cold (0° C.) solution of NaHCO$_3$ (18 g), NaHSO$_3$ (5 g), and H$_2$O—CH$_2$CL$_2$ (75 mL-50 mL). After 1h, the methylene chloride was removed in vacuo, and the aqueous layer was extracted with ethyl acetate (2×100 mL), washed with H$_2$O (2×50 mL), washed with brine (2×50 mL), and dried (Na$_2$SO$_4$). After concentration in vacuo, the residue was purified by flash chromatography (ethyl acetate:hexane 1:4 to ethyl acetate:hexane 1:1) to afford 9.78 g of the beta lactam. The material was recrystallized from ether:hexane to afford 7.50 g of beta lactam: m.p. 46°-47° C.

Anal. Calcd. for C$_{11}$H$_{13}$NO: C, 75.40; H, 7.48; N, 7.99.

Found: C, 75.36; H, 7.69; N, 8.06.

The beta lactam was opened by treatment with neat ethanol saturated with HCl gas to afford the ethyl ester of the beta amino acid as the hydrochloride salt. The product was verified by C NMR (CDCl$_3$) delta 14.5, 31.9, 34.6, 37.2, 49.0, 61.8, 126.7, 128.9, 129.0, 140.5, 170.6.

The title compound was prepared in the manner of example 1 with the following changes in procedure 1A: substitution of 3-phenethyl-beta-alanine for 3-phenyl-beta-alanine.

Anal. Calcd. for C$_{25}$H$_{33}$N$_3$O$_3$ plus 0.35 H$_2$O and 1.0 CF$_3$CO$_2$H: C, 59.63; H, 6.43; N, 7.73. Found: C, 59.78; H, 6.35; N, 7.67.

EXAMPLE 13

Preparation of 3-[[5-[4-(aminoiminomethyl)phenyl]-4-methylene-1-oxopentyl]amino]butanoic acid

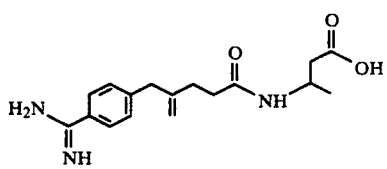

To a solution of bis(benzonitrile)palladium(II) chloride (100 mg, 0.26 mmol), triethylamine (726 mg, 7.18 mmol), in 50 mL of THF was added 5-(p-cyanophenyl)-4-pentynoic acid (5.0 g, 25.1 mmol) of example 11. The reaction mixture was warmed to 67° C. for 1 h followed by cooling to 23° C. After concentration in vacuo, the residue was purified by flash chromatography (gradient—1 liter hexane:ethyl acetate (7:3) followed by 100% ethyl acetate) which afforded the enol lactone (3.0 g, 60%).

Anal. Calcd. for $C_{12}H_9NO_2$: C, 72.35; H, 4.55; N, 7.03.

Found: C, 72.09; H, 4.74; H, 6.97.

The enol lactone (3.0 g, 15.1 mmol) was hydrolyzed by treatment with 1N NaOH:methanol (15 mL:15 mL) for 30 min. After removal of the methanol in vacuo, the reaction mixture was acidified with 2N potassium hydrogen sulfate, extracted with ethyl acetate (2×80 mL), and dried ($Na_2SO_4$). Concentration in vacuo afforded 2.7 g of the ketoacid.

The ketoacid (2.7 g, 13.5 mmol) was converted to the methyl ester by treating with acetyl bromide (1.83 g, 14.85 mmol) in methanol (30 mL) at 0° C. for 30 min followed by 20 h at 23° C. After concentration in vacuo, the residue was dissolved in ethyl acetate (100 mL), washed with saturated sodium bicarbonate (1×30 mL), washed with brine (1×30 mL), and dried ($Na_2SO_4$). Concentration in vacuo afforded the methyl ester (2.5 g, 87%). The product was verified by C NMR ($CDCl_3$) delta 27.6, 36.8, 49.2, 51.6, 118.5, 130.2, 132.1, 139.1, 173.3, 204.7.

The keto ester was methylenated as described in the literature [L. Lombard, *Tetrahedron Lett.*, 4293 (1982)].

The title compound was prepared in the manner of example 1 with the following changes in procedure: substitution of 5-(p-Cyanophenyl)-4-methylenylpentanoic acid for 5-(p-Cyanophenyl)pentanoic acid and 3-methyl-beta-alanine for 3-phenyl-beta-alanine in example 1C.

Anal. Calcd. for $C_{17}H_{23}N_3O_3$ plus 0.2 $H_2O$ and 0.8 HI: C, 48.23; H, 5.76; N, 9.93. Found: C, 48.80; H, 5.13; N, 8.72.

EXAMPLE 14

Preparation of 3-[[5-[4-(aminoiminomethyl)phenyl]-4-methyl-1-oxopentyl]amino]butanoic acid

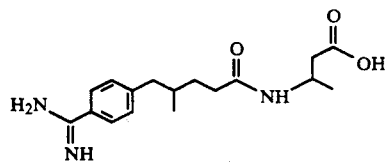

A solution of 35 mg (0.11 mmol) of the final product of Example 13 in 8 mL of methanol was hydrogenated over 60 mg of 10% Pd/C under a balloon atmosphere of hydrogen over a 20 h period. Filtration and evaporation of the solvent in vacuo afforded 34 mg of the title compound in pure form. The product was verified by C NMR ($CD_3OD$) delta 18.0, 19.0, 32.2, 33.4, 34.3, 34.3, 40.4, 42.3, 42.6, 126.6, 127.4, 129.8, 148.3, 167.0, 173.7, 173.8.

EXAMPLE 15

Preparation of β-[[5-[4-(aminoiminomethyl)-phenyl]-1-oxopentyl]amino]-N-hydroxybenzeneorooanamide

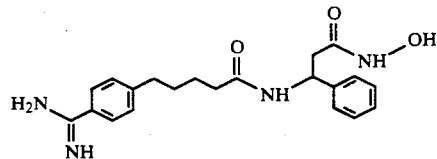

The title compound was prepared in the manner of example 1 with the following modifications: the product of Example 1C was coupled with O-benzylhydroxylamine in the manner of the DSC coupling protocol described in Example 1C. After converting the nitrile to the amidine as described in Example 1D, the deprotected hydroxamic acid was formed using the following procedure: A solution of 150 mg (0.318 mmol) of the O-benzylhydroxamic acid in $DMF:H_2O:1N$ HCl (19mL:0.5 mL:0.5 mL) was hydrogenated over 10% Pd/C under a hydrogen atmosphere (2 psi) over 30 min period. Filtration and evaporation of the solvent in vacuo afforded 115 mg of the title compound which was purified on a Waters reverse-phase C-18 microbondapak column (5 cm×30 cm) using a linear gradient of 5% acetonitrile/water 0.05% trifluoroacetic acid to 40% acetonitrile/water 0.05% trifluoroacetic acid (30 min) with a flow rate of 80 mL/min to afford the title compound in pure form. The product was verified by C NMR ($CD_3OD$) delta 24.5, 29.4, 34.5, 35.0, 38.5, 50.2, 125.0, 125.8, 126.7, 127.1, 127.8, 128.6, 140.5, 148.6, 166.8, 167.9, 173.6;

Anal. Calcd. for $C_{21}H_{26}N_4O_3$ plus 1.6 $H_2O$ and 1.0 $CF_3CO_2H$: C, 52.59; H, 5.79; N. 10.67. Found: C, 52.34; H, 5.25; N, 10.37.

EXAMPLE 16

Preparation of 3R-[[5-[4-(aminoiminomethyl)phenyl]-1-oxopentyl]amino]butanoic acid

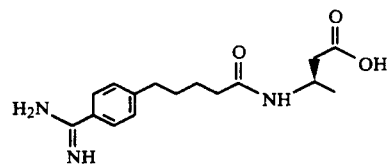

To a solution of N-t-BOC-D-alanine (5.05 g, 25.1 mmol) in anhydrous ether (100 mL) was added N-methylmorpholine (2.76 mL, 25.1 mmol) at 23° C. After cooling to −10° C., isobutyl choroformate (3.42 g, 25.1 mmol) was added dropwise. The reaction was allowed to warm to 23° C. for 1 h at which point the reaction mixture was filtered. The filtrate was treated with an excess of diazomethane in ether at 0° C. After 1 h, the reaction was concentrated with a stream of nitrogen in the hood. The residue was dissolved in anhydrous ethanol (125 mL), and a solution of silver benzoate (1.09 equiv.) in triethylamine (10 mL) was added slowly (reaction exotherms). After 1 h at 23° C., the reaction was filtered and concentrated in vacuo. The residue was purified by flash chromatography (gradient—1 liter ethyl acetate:hexane 1:9 to ethyl acetate:hexane 2:8) to afford N-t-BOC-R-3- aminobutyric acid (5.04 g, 87%): optical rotation (c 1.00, CHCl₃) [α]_D +18.7 deg.

Anal. Calcd for $C_{11}H_{21}NO_4$ C, 57.12; H, 9.15; N, 6.06. Found: C, 56.63; H, 9.24; N, 6.02.

The ester (535 mg, 2.31 mmol) was hydrolyzed with 1N NaOH:methanol (3 mL:2 mL) for 20 h. After removal of the methanol in vacuo, the reaction mixture was acidified with 2N potassium hydrogen sulfate, extracted with ethyl acetate (2×80 mL), and dried (Na₂SO₄). The BOC group was removed by treating with 90% TFA- H₂O for 30 min. After concentration in vacuo, the residue was lyophilized and subsequently recrystallized (acetone —H₂O) to afford 231 mg of 3-aminobutyric acid: optical rotation (c 0.97, H₂O) [α]_D −21.3 deg.

The title compound was prepared in the manner of the racemic Example 3 with the same C NMR.

EXAMPLE 17

A. Preparation of Ethyl 3-amino-3-(4-ethoxyphenyl)propanoate-HCl 4-ethoxybenzaldehyde (3 g; 20 mmoles), malonic acid (2.4 g; 23 mmoles) and ammonium acetate (2 g; 28 mmoles) were gently refluxed in ethanol (100 ml) overnight. The reaction mixture was allowed to cool down to room temperature and the solid precipitate was collected by filtration and washed with ethanol (2×30 ml). The air dried free acid (FAB-MS: (M+H)+ =210) was suspended in the absolute ethanol (100 ml). The solution was cooled in an ice bath and HCl gas was bubbled through the solution for 15 minutes. The reaction mixture was stirred at room temperature for 20 h, and then the solvent was removed in vacuo. The residue was dried in the vacuum dessicator and was used without any further purification. FAB-MS: (M+H)+ =238.

B. Preparation of 5-[4-(aminoiminomethyl)phenyl]pentanoic acid

To a slurry of 4.06 g (20.0 mmol) of 5-(p-cyanophenyl)pentanoic acid in 60 mL of anhydrous ether was added 100 mL of lithium bis(trimethylsilyl)amide (1.0M in hexanes) via cannula. After 20 h at 23° C., the reaction was quenched through the slow addition of water (25 mL) followed by adjustment of the pH to 7 using 20% HCl (approx. 45 mL required). After dilution with acetonitrile (25 mL), the product was collected by filtration, washed with water (50 mL), washed with ether-:acetonitrile (7:3, 100 mL), washed with ether (50 mL), and dried in vacuo to afford 4.0 g (90%) of the product a the zwitter-ion product. The zwitter-ion product was converted to the HCl salt by treatment with saturated anhydrous HCl in dioxane. After concentration in vacuo, the precipitate was washed with ether and stored in the dessicator.

Anal. Calcd. for $C_{12}H_{16}N_2O_2$: C, 65.43; H, 7.32; N, 12.72. Found: C, 65.37; H, 7.33; N, 12.20.

C. Preparation of ethyl β-[[5-[4-(aminoiminomethyl)phenyl]-1-oxopentyl]amino]-4-ethoxybenzenepropanoate

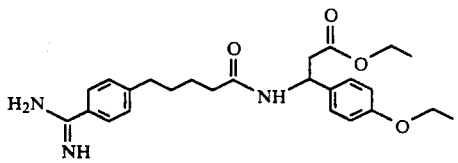

4-amidinophenylpentanoic acid-HCl (0.4 g; 1.66 mmoles); disuccinimidyl carbonate (0.5 g; 2 mmoles) and -dimethylaminopyridine (40 mg) were stirred in DMF (25 ml) overnight. To this mixture, a solution of ethyl 3-amino-3-(4-ethoxyphenyl)propanoate-HCl (0.41 g; 1.5 mmoles) and N,N-diisopropylethylamine (0.14 g; 1.1 mmoles) in DMF (10 ml) was added with stirring. After 20 h at 23° C., the reaction mixture was concentrated in vacuo. The residue was dissolved in acetonitrile/water and purified on a Waters Deltapak C-18 HPLC column (30 cm×5 cm) with a flow rate of 80 ml/min. A linear gradient (30 min.) of 10 to 40% acetonitrile/water/0.05% TFA and 40 to 60% in 10 min. was used. The ester eluted at 42–46% acetonitrile concentration and the desired peak was lyophilized to yield 170 mg of 14 as a white solid which was converted to its HCl salt. FAB-MS: (MH+)=440. H NMR (DMSO-d₆) δ1.10 (t, 3H, CO₂CH₂CH₃), 1.31 (t, 3H, Ar-OCH₃), 1.50 (br, 4H, CH₂CH₂CH₂CH₂), 2.1 (t, 2H, CH₂CH₃CO), 2.67 (m, 4H, Ar-CH₂ and CHCH₂CO), 3.98 (m, 4H, CO₂CH₂CH₃ and Ar-OCH₂CH₃), 5.16 (q, 1H, CH), 6.82 and 7.2 (d, 4H, Ar), 7.4 and 7.73 (d, 4H, Ar), 8.3 (d, 1H, CONH), 9.0 and 9.27 (s, 4H, H₂NCNH₂).

EXAMPLE 18

Preparation of β-[[5-[4-(aminoiminomethyl)phenyl]-1-oxopentyl]amino]-4-ethoxybenzenepropanoic acid

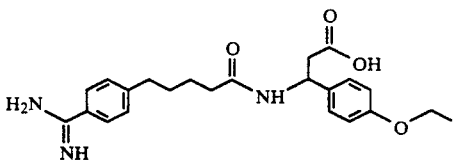

The final product of Example 17 (100 mg) was treated with 1N LiOH/methanol (10 ml; 1:1) for 30 min. The mixture was neutralized with 4N HCl and diluted with water (25 ml). The product was purified on a Deltapak column using a 30 min. linear gradient of 10 to 40% acetonitrile/water/0.05% TFA as described above. The desired product eluted at 32–35% acetonitrile concentration and was collected and lyophilized to yield 65 mg of solid 15 of Scheme L. FAB-MS: MH+ =412. HNMR (DMSO-d₆) δ1.31 (t, 3H, Ar-OCH₂CH₃), 1.50 (br, 4H, CH₂CH₂CH₂CH₂), 2.1 (t, 2H, CH₂CH₂CO), 2.67 (m, 4H, Ar-CH₂ and CHCH₂CO), 3.98 (m, 2H, Ar-OCH₂CH₃), 5.12 (q, 1H, CH), 6.82 and 7.2 (d, 4H, Ar), 7.4 and 7.73 (d, 4H, Ar), 8.23 (d, 1H, CONH), 8.89 and 9.20 (s, 4H, H₂NCNH₂).

Anal. Calcd. for $C_{23}H_{29}N_3O_4$ plus 1.0 CF₃CO₂H: C, 54.35; H, 5.47; N, 7.60. Found: C, 54.57; H, 5.51; N, 7.49.

EXAMPLE 19

Preparation of Ethyl 3-amino-3-(3,5-dichlorophenyl)propanoate, TFA 3,5-dichlorobenzaldehyde (1.75 g; 10 mmol) was dissolved in 50 mL ethanol. Ammonium acetate (1.9 g; 25 mmol) and ethyl-hydrogen-malonate (2 mL; 20 mmol) were added to the solution. It was stirred at reflux for 4h. Ethanol was evaporated and the residue was dissolved in 10% acetonitrile/H$_2$O and it was purified on HPLC. Ethyl 3-amino-3-(3,5-dichlorophenyl)-propanoate was isolated after lyophilization. FAB-MS: (MH$^+$)=282.1.

B. Preparation of ethyl β-[[5-[4-(aminoiminomethyl]phenyl]-1-oxopentyl-]amino]-3,5-dichlorobenzenepropanoate

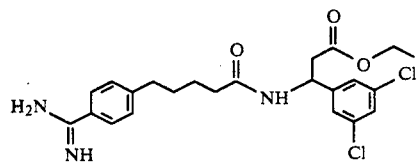

Ethyl 3-amino-3-(3,5-dichlorophenyl)-propanoate.TFA (370 mg; 1 mmol) was dissolved in 10 mL DMF. Then 4-amidino-phenyl-pentanoic acid·HCl (300 mg; 1.2 mmol), benzotriazol-1-yl-oxy-tris(dimethylamino)-phosphonium hexafluorophosphate (BOP) (660 mg; 1.5 mmoles) and diisopropylethylamine (0.52 mL; 3 mmol) were added to the solution and the mixture was stirred for 2h at room temp. DMF was evaporated and the remaining oil was dissolved in 30% acetonitrile/H$_2$O. It was purified on HPLC using a gradient of 10–50% acetonitrile/H$_2$O/0.05% TFA in 30 min. Yield: 420 mg (66%). FAB-MS: (MH$^+$)=484.0. H NMR (DMSO-d$_6$) δ1.11 (t, 3H, CO$_2$CH$_2$C$\underline{H}$$_3$), 1.51 (br, 4H, CH$_2$C$\underline{H}$$_2$C$\underline{H}$$_2$CH$_2$), 2.13 (t, 2H, CH$_2$C$\underline{H}$$_2$CO), 2.68 (t, H, ArC$\underline{H}$$_2$), 2.76 (q, 2H, CHC$\underline{H}$$_2$CO), 4.01 (m, 2H, CO$_2$C$\underline{H}$$_2$CH$_3$), 5.17 (q, 1H, CH), 7.36 and 7.48 (d, 3H, Ar), 7.42 and 7.73 (d, 4H, Ar), 8.43 (d, 1H, CONH), 8.97 and 9.22 (s, 4H, H$_2$NCNH$_2$).

Anal Calcd. for C$_{23}$H$_{27}$N$_3$O$_3$Cl$_2$ plus CF$_3$CO$_2$H: C, 66.34; H, 6.54; N, 10.09. Found: C, 66.28; H, 6.49; N, 10.18.

EXAMPLE 20

Preparation of β-[[5-[4-(aminoiminomethyl)phenyl]-1-oxopentyl-]amino]-3,5-dichlorobenzenepropanoic acid

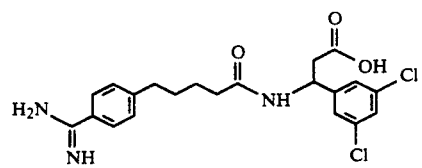

The final product of example 19 (90 mg; 0.2 mmol) was dissolved in 10 mL methanol and 10 mL 1N LiOH was added to the solution. After 30 min reaction methanol was removed in vacuo and the remaining aqueous solution was acidified to pH 3 with 50% acetic acid. It was purified on HPLC using acetonitrile gradient 10–50% in 30 min. Yield: 80 mg (95%). FAB-MS: (MH$^+$)=436.1. H NMR (DMSO-d$_6$) δ1.52 (br, 4H, CH$_2$C$\underline{H}$$_2$C$\underline{H}$$_2$CH$_2$), 2.14 (t, 2H, CH$_2$C$\underline{H}$$_2$CO), 2.66 (t, 2H, ArC$\underline{H}$$_2$), 2.70 (q, 2H CHC$\underline{H}$$_2$CO), 5.12 (q, 1H, CH), 7.34 and 7.48 (d, 3H, Ar), 7.41 and 7.72 (d, 4H, Ar), 8.40 (d, 1H, CONH), 8.89 and 9.21 (s, 4H, H$_2$NCNH$_2$).

Anal. Calcd. for C$_{21}$H$_{23}$N$_3$O$_3$Cl$_2$ plus 1.0 CF$_3$CO$_2$H: C, 57.81; H, 5.31; N, 9.63. Found: C, 57.07; H, 5.17; N, 9.34.

In the manner described in Scheme A, Method A or in the manner described in Scheme B, Method B the compounds of Examples 21 to 85 of Table A were prepared. I Table A the method of preparation (designated A or B) is set forth under the example number. Both the example number and the method of preparation appear in the first column of Table A.

TABLE A

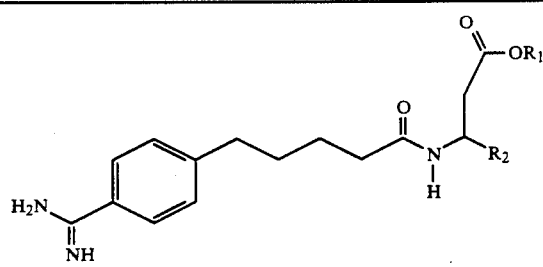

| Example Method | R$_1$ | R$_2$ | Theory | Found | Mass Spectrum | |
|---|---|---|---|---|---|---|
| 21 B (DSC) | H | ![4-F phenyl] | C: 55.29 H: 5.04 N: 8.45 | C: 55.99 H: 5.09 N: 7.91 | 386 | C$_{21}$H$_{24}$FN$_3$O$_3$.CF$_3$CO$_2$H β-[[5-[4-(aminoiminomethyl)phenyl]-1-oxopentyl]amino]-4-fluorobenzenepropanoic acid |
| 22 B (DSC) | H | ![3-F phenyl] | C: 53.38 H: 5.25 N: 8.12 | C: 53.38 H: 4.86 N: 8.03 | 386 | C$_{21}$H$_{24}$FN$_3$O$_3$.CF$_3$CO$_2$H.H$_2$O β-[[5-[4-(aminoiminomethyl)phenyl]-1-oxopentyl]amino]-3-fluorobenzenepropanoic acid |

TABLE A-continued

| Example Method | R₁ | R₂ | Theory | Found | Mass Spectrum | |
|---|---|---|---|---|---|---|
| 23 B (DSC) | H | 2,5-dimethoxyphenyl (OCH₃ at 2 and 5) | C: 51.97 H: 5.93 N: 7.30 | C: 51.78 H: 5.06 N: 7.02 | 428 | C₂₃H₂₉N₃O₅.CF₃CO₂H.2H₂O β-[[6-[4-(aminoiminomethyl)phenyl]-1-oxopentyl]amino]2,5-dimethoxybenzenepropanoic acid |
| 24 B (DSC) | H | 2-fluorophenyl | C: 52.44 H: 5.37 N: 8.01 | C: 52.33 H: 4.71 N: 7.86 | 386 | C₂₁H₂₄FN₃O₃.CF₃CO₂H.1 1/2H₂O β-[[5-[4-(aminoiminomethyl)phenyl]-1-oxopentyl]amino]-2-fluorobenzenepropanoic acid |
| 25 B (BOP) | H | 4-chlorophenyl | C: 51.68 H: 5.05 N: 7.86 | C: 51.00 H: 4.71 N: 7.51 | 403 | C₂₁H₂₄ClN₃O₃.CF₃CO₂H.H₂O β-[[5-[4-(aminoiminomethyl)phenyl]-1-oxopentyl]amino]-4-chlorobenzene propanoic acid |
| 26 B (BOP) | H | 4-(phenylmethoxy)phenyl (OBn) | C: 59.45 H: 5.61 N: 6.93 | C: 58.65 H: 5.01 N: 6.78 | 474 | C₂₈H₃₁N₃O₄.CF₃CO₂H.H₂O β-[[5-[4-(aminoiminomethyl)phenyl]-1-oxopentyl]amino]-4-(phenylmethoxy)benzenepropanoic acid |
| 27 B (BOP) | H | 4-carboxyphenyl (CO₂H) | C: 53.0 H: 5.1 N: 7.73 | C: 53.71 H: 4.78 N: 7.85 | 412 | C₂₂H₂₅N₃O₅.CF₃COOH.H₂O β-[[5-[4-(aminoiminomethyl)phenyl]-1-oxopentyl amino]-4-carboxy benzenepropanoic acid |
| 28 B (DSC) | H | 4-cyanophenyl (CN) | C: 54.96 H: 5.19 N: 10.68 | C: 54.76 H: 4.90 N: 10.55 | 393 | C₂₂H₂₄N₄O₃.CF₃CO₂H.H₂O β-[[5-[4-(aminoiminomethyl)phenyl]-1-oxopentyl]amino]-4-cyanobenzenepropanoic acid |
| 29 B (DSC) | H | 4-(aminoiminomethyl)phenyl | C: 47.63 H: 4.76 N: 10.68 | C: 46.97 H: 4.37 N: 10.43 | 410 | C₂₂H₂₇N₅O₃.2CF₃CO₂H.H₂O 4-(aminoiminomethyl)-β-[[5-[4-(aminoiminomethyl)phenyl]-1-oxopentyl]aminobenzenepropanoic acid |
| 30 B (BOP) | H | 3,5-dichlorophenyl | C: 48.59 H: 4.57 N: 7.39 | C: 49.07 H: 4.17 N: 7.34 | 437 | C₂₁H₂₃Cl₂N₃O₃.TFA.H₂O β-[[5-[4-(aminoiminomethyl)phenyl]-1-oxopentyl]amino]-3,5-dichlorobenzenepropanoic acid |
| 31 B (DSC) | H | 2-hydroxy-4-methoxyphenyl (HO, OCH₃) | C: H: N: | C: H: N: | 414 | C₂₂H₂₇N₂O₅ (±)-β-[[5-[4-aminoiminomethyl)phenyl]-1-oxopentyl]amino]-2-hydroxy-4-methoxybenzenepropanoic acid |
| 32 B (DSC) | H | 2,4-dimethoxyphenyl (CH₃O, OCH₃) | C: 55.45 H: 6.10 N: 7.76 | C: 55.63 H: 6.34 N: 8.45 | 428 | C₂₃H₂₉N₃O₅.CF₃COOH β-[[5-[4-(aminoiminomethyl)phenyl]-1-oxopentyl]amino]-2,4-dimethoxybenzenepropanoic acid |

TABLE A-continued

[Structure: H₂N-C(=NH)-C₆H₄-(CH₂)₄-C(=O)-NH-CH(R₂)-CH₂-C(=O)-OR₁]

| Example Method | R₁ | R₂ | Theory | Found | Mass Spectrum | |
|---|---|---|---|---|---|---|
| 33 B (DSC) | H | 2,4-dichlorophenyl | C: 48.59 H: 4.57 N: 7.39 | C: 48.85 H: 4.18 N: 7.33 | 437 | $C_{21}H_{22}N_3O_3Cl_2 \cdot CF_3CO_2H \cdot H_2O$ β-[[5-[4-(aminoiminomethyl)phenyl]-1-oxopentyl]amino]-2,4-dichlorobenzenepropanoic acid |
| 34 B (DSC) | H | 4-CF₃-phenyl | C: 50.80 H: 4.79 N: 7.40 | C: 50.65 H: 4.36 N: 7.18 | 436 | $C_{22}H_{24}F_3N_3O_3 \cdot CF_3COOH \cdot H_2O$ β-[[5-[4-(aminoiminomethyl)phenyl]-1-oxopentyl]amino]-4-(trifluoromethyl)benzenepropanoic acid |
| 35 B (DSC) | H | 3-CF₃-phenyl | C: 50.80 H: 4.79 N: 7.40 | C: 51.20 H: 4.43 N: 7.40 | 436 | $C_{22}H_{24}F_3N_3O_3 \cdot CF_3COOH \cdot H_2O$ β-[[5-[4-(aminoiminomethyl)phenyl]-1-oxopentyl]amino]-3-(trifluoromethyl)benzenepropanoic acid |
| 36 B (DSC) | H | 3,4-dimethoxyphenyl | C: 53.66 H: 5.76 N: 7.50 | C: 53.94 H: 5.72 N: 7.62 | 428 | $C_{23}H_{29}N_3O_5 \cdot CF_3CO_2H \cdot H_2O$ β-[[5-[4-(aminoiminomethyl)phenyl]-1-oxopentyl]amino]-3,4-dimethoxybenzenepropanoic acid |
| 37 B (BOP) | H | 3-benzo[b]thiophenyl | C: H: N: | C: H: N: | 438 | $C_{24}H_{27}N_3O_3S$ βR-[[5-[4-(aminoiminomethyl)phenyl]-1-oxopentyl]amino]-3-benzo[b]thiophenebutanoic acid |
| 38 B (DSC) | H | 3-methoxyphenyl | C: 54.44 H: 5.71 N: 7.93 | C: 54.24 H: 5.20 N: 7.79 | 398 | $C_{22}H_{27}N_3O_4 \cdot CF_3COOH \cdot H_2O$ β-[[5-[4-(aminoiminomethyl)phenyl]-1-oxopentyl]amino]-3-methoxybenzenepropanoic acid |
| 39 B (DSC) | H | 4-phenoxyphenyl | C: 58.87 H: 5.45 N: 7.10 | C: 59.33 H: 5.25 N: 7.15 | 460 | $C_{27}H_{29}N_3O_4 \cdot CF_3COOH \cdot H_2O$ β-[[5-[4-(aminoiminomethyl)phenyl]-1-oxopentyl]amino]-4-phenoxybenzenepropanoic acid |
| 40 B (DSC) | H | 3-cyclohexenyl | C: 54.86 H: 6.40 N: 8.34 | C: 55.71 H: 6.05 N: 8.33 | 372 | $C_{21}H_{29}N_3O_3 \cdot CF_3CO_2H \cdot H_2O$ β-[[5-[4-(aminoiminomethyl)phenyl]-1-oxopentyl]amino]-3-cyclohexene-1-propanoic acid |
| 41 B (DSC) | H | 3-phenoxyphenyl | C: 58.87 H: 5.45 N: 7.10 | C: 58.69 H: 4.95 N: 6.92 | 460 | $C_{27}H_{29}N_3O_4 \cdot CF_3COOH \cdot H_2O$ β-[[5-[4-(aminoiminomethyl)phenyl]-1-oxopentyl]amino]-3-phenoxybenzenepropanoic acid |
| 42 B (DSC) | H | 4-bromophenyl | C: 47.79 H: 4.71 N: 7.29 | C: 48.39 H: 4.47 N: 7.42 | 447 | $C_{21}H_{24}BrN_3O_3 \cdot CF_3COOH \cdot H_2O$ β-[[5-[4-(aminoiminomethyl)phenyl]-1-oxopentyl]amino]-4-bromobenzenepropanoic acid |

TABLE A-continued

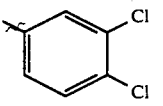

| Example Method | R₁ | R₂ | Theory | Found | Mass Spectrum | | |
|---|---|---|---|---|---|---|---|
| 43 B (BOP) | H | 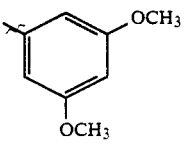 | C: 48.59 H: 4.57 N: 7.39 | C: 47.79 H: 4.01 N: 7.04 | 437 | $C_{21}H_{23}N_3O_3Cl_2 \cdot CF_3CO_2H \cdot H_2O$ | β-[[-5-[4-(aminoiminomethyl)phenyl]-1-oxopetnyl]amino]-3,4-dichlorobenzenepropanoic acid |
| 44 B (DSC) | H | 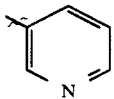 | C: 53.66 H: 5.76 N: 7.50 | C: 53.73 H: 5.42 N: 7.38 | 428 | $C_{22}H_{29}N_3O_3 \cdot CF_3CO_2H \cdot H_2O$ | β-[[5-[4-(aminoiminomethyl)phenyl]-1-oxopentyl]amino]-3,5-dimethoxybenzenepropanoic acid |
| 45 B (DSC) | Et | 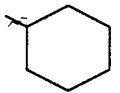 | C: 48.72 H: 5.95 N: 10.33 | C: 49.84 H: 5.28 N: 9.66 | 397 | $C_{22}H_{29}N_4O_3 \cdot 4HCl$ | ethyl β-[[5-[4-aminoiminomethyl)phenyl]-1-oxopentyl]amino]-2-pyridinepropanoate |
| 46 B (DSC) | 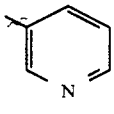 | 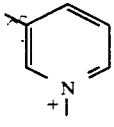 | C: 55.14 H: 6.69 N: 10.05 | C: 55.60 H: 6.93 N: 10.07 | 451 | $C_{29}H_{24}N_4O_3 \cdot 2HCl$ | cyclohexyl β-[[5-[4-(aminoiminomethyl)phenyl]-1-oxopentyl]amino]-3-pyridinepropanoate |
| 47 B (DSC) | H | 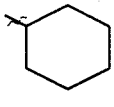 | C: 49.49 H: 6.79 N: 11.04 | C: 48.84 H: 6.34 N: 10.97 | 420 | $C_{21}H_{27}N_4O_3Cl \cdot HCl \cdot 3H_2O$ | 3[1-[[5-[4-(aminoiminomethyl)phenyl]-1-oxopentyl]amino]-2-carboxyethyl]-1-methylpyridinium chloride |
| 48 B (DSC) | H | 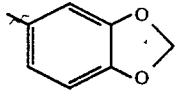 | C: 54.65 H: 6.78 N: 8.31 | C: 55.09 H: 6.40 N: 8.33 | 374 | $C_{21}H_{31}N_3O_3 \cdot CF_3CO_2H \cdot H_2O$ | β-[[5-[4-(aminoiminomethyl)phenyl]-1-oxopentyl]amino]cyclohexanepropanoic acid |
| 49 B (DSC) | H | 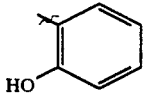 | C: 53.03 H: 5.19 N: 7.73 | C: 52.58 H: 4.74 N: 7.55 | 412 | $C_{22}H_{29}N_3O_3 \cdot CF_3CO_2H \cdot H_2O$ | β-[[5-[4-(aminoiminomethyl)phenyl]-1-oxopentyl]amino]-1,3-benzodioxole-5-propanoic acid |
| 50 B (DSC) | H | 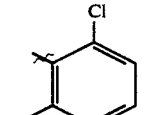 | C: H: N: | C: H: N: | 384 | $C_{21}H_{25}N_3O_4$ | (±)-β-[[5-[4-(aminoiminomethyl)phenyl]-1-oxopentyl]amino-2-hydroxybenzenepropanoic acid |
| 51 B (BOP) | H | 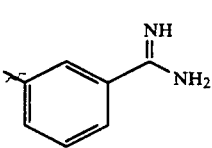 | C: 48.59 H: 4.57 N: 7.39 | C: 49.12 H: 4.19 N: 7.30 | 437 | $C_{21}H_{23}N_3O_3Cl_2 \cdot CF_3CO_2H \cdot H_2O$ | β-[[5-[4-(aminoiminomethyl)phenyl]-1-oxopentyl]amino]-2,6-dichlorobenzenepropanoic acid |
| 52 B (DSC) | H | | C: 47.63 H: 4.76 N: 10.68 | C: 47.01 H: 4.49 N: 10.45 | 410 | $C_{22}H_{27}N_5O_3 \cdot 2CF_3CO_2H \cdot H_2O$ | 3-(aminoiminomethyl)-β-[[5-[4-(aminoiminomethyl)phenyl]-1-oxopentyl]amino]benzenepropanoic acid |

TABLE A-continued

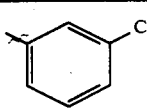

| Example Method | R₁ | R₂ | Theory | Found | Mass Spectrum | |
|---|---|---|---|---|---|---|
| 53 B (DSC) | H | 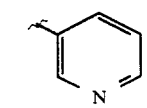 | C: 54.96<br>H: 5.19<br>N: 10.68 | C: 54.98<br>H: 4.81<br>N: 10.45 | 393 | $C_{22}H_{24}N_4O_3 \cdot CF_3CO_2H \cdot H_2O$<br>β-[[5-[4-(aminoiminomethyl)phenyl]-1-oxopentyl]amino]-3-cyanobenzenepropanoic acid |
| 54 B (DSC) | H | 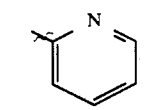 | C: 45.55<br>H: 4.78<br>N: 8.89 | C: 45.50<br>H: 4.10<br>N: 8.67 | 369 | $C_{20}H_{24}N_4O_3 \cdot 2CF_3CO_2H \cdot 2H_2O$<br>β-[[5-[4-(aminoiminomethyl)phenyl]-1-oxopentyl]amino]-3-pyridinepropanoic acid |
| 55 B (BOP) | H | 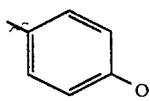 | C: 46.94<br>H: 4.56<br>N: 9.12 | C: 48.90<br>H: 4.50<br>N: 9.85 | 369 | $C_{20}H_{24}N_4O_3 \cdot 2CF_3CO_2H \cdot H_2O$<br>β-[[5-[4-(aminoiminomethyl)phenyl]-1-oxopentyl]amino]-2-pyridinepropanoic acid |
| 56 B (BOP) | H | 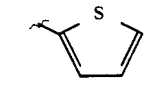 | C: 53.50<br>H: 5.43<br>N: 8.15 | C: 53.03<br>H: 4.91<br>N: 8.02 | 384 | $C_{21}H_{25}N_3O_4 \cdot CF_3CO_2H \cdot H_2O$<br>β-[[5-[4-(aminoiminomethyl)phenyl]-1-oxopentyl]amino]-4-hydroxybenzenepropanoic acid |
| 57 B (DSC) | H | 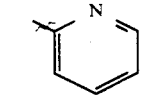 | C:<br>H:<br>N: | C:<br>H:<br>N: | 374 | $C_{19}H_{22}N_3O_3S$<br>(±)-β-[[5-[4-(aminoiminomethyl)phenyl]-1-oxopentyl]amino]-2-thiophenepropanoic acid |
| 58 B (BOP) | Et | 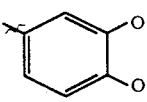 | C:<br>H:<br>N: | C:<br>H:<br>N: | 397 | $C_{22}H_{28}N_4O_3$<br>ethyl β-[[5-[4-(aminoiminomethyl)phenyl]-1-oxopentyl]amino]-2-pyridinepropanoate |
| 59 B (DSC) | Et | 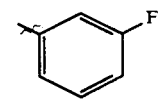 | C: 58.35<br>H: 6.52<br>N: 8.50 | C: 58.12<br>H: 6.22<br>N: 8.48 | 440 | $C_{24}H_{29}N_3O_5 \cdot HCl \cdot H_2O$<br>ethyl β-[[5-[4-(aminoiminomethyl)phenyl]-1-oxopentyl]amino]-13,-benzodioxole-5-propanoate |
| 60 B (DSC) | Et | 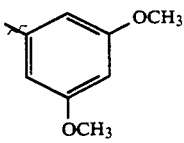 | C:<br>H:<br>N: | C:<br>H:<br>N: | 414 | $C_{23}H_{28}N_3O_3F$<br>ethyl β-[[5-[4-(aminoiminomethyl)phenyl]-1-oxopentyl]amino]-3-fluorobenzenepropanoate |
| 61 B (DSC) | Et | 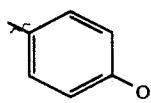 | C: 55.19<br>H: 6.17<br>N: 7.15 | C: 55.14<br>H: 5.21<br>N: 7.31 | 456 | $C_{25}H_{33}N_3O_5 \cdot CF_3CO_2H \cdot H_2O$<br>ethyl β-[[5-[4-(aminoiminomethyl)phenyl]-1-oxopentyl]amino]-3,5-dimethoxybenzenepropanoate |
| 62 B (DSC) | Et | 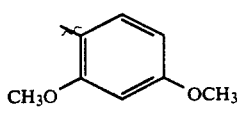 | C:<br>H:<br>N: | C:<br>H:<br>N: | 488 | $C_{29}H_{33}N_3O_4$<br>ethyl β-[[5-[4-(aminoiminomethyl)phenyl]-1-oxopentyl]amino]-4-phenoxybenzenepropanoate |
| 63 B (DSC) | Et |  | C:<br>H:<br>N: | C:<br>H:<br>N: | 456 | $C_{25}H_{33}N_3O_5$<br>ethyl β-[[5-[4-(aminoiminomethyl)phenyl]-1-oxopentyl]amino]-2,4-dimethoxybenzenepropanoate |

TABLE A-continued

[Structure: H₂N-C(=NH)-C₆H₄-(CH₂)₄-C(=O)-NH-CH(R₂)-CH₂-C(=O)-OR₁]

| Example Method | R₁ | R₂ | Theory | Found | Mass Spectrum | |
|---|---|---|---|---|---|---|
| 64 B (DSC) | Et | 4-CN-C₆H₄- | C: H: N: | C: H: N: | 421 | $C_{24}H_{28}N_4O_3$ ethyl β-[[5-[4-(aminoiminomethyl)phenyl]-1-oxopentyl]amino]-4-cyanobenzenepropanoate |
| 65 B (DSC) | Et | 3,4-(OCH₃)₂-C₆H₃- | C: H: N: | C: H: N: | 456 | $C_{25}H_{33}N_3O_5$ ethyl β-[[5-[4-(aminoiminomethyl)phenyl]-1-oxopentyl]amino]-3,4-dimethoxybenzenepropanoate |
| 66 B (BOP) | Et | 3,4-Cl₂-C₆H₃- | C: H: N: | C: H: N: | 465 | $C_{23}H_{27}N_3O_3Cl_2$ ethyl β-[[5-[4-(aminoiminomethyl)phenyl]-1-oxopentyl]amino]-3,4-dichlorobenzenepropanoate |
| 67 B (BOP) | Et | 4-OBn-C₆H₄- | C: H: N: | C: H: N: | 502 | $C_{30}H_{35}N_3O_4$ ethyl β-[[5-[4-(aminoiminomethyl)phenyl]-1-oxopentyl]amino]-4-(phenylmethoxy)benzenepropanoate |
| 68 B (BOP) | Et | 4-CO₂Et-C₆H₄- | C: H: N: | C: H: N: | 468 | $C_{26}H_3N_3O_5$ ethyl β-[[5-[4-(aminoiminomethyl)phenyl]-1-oxopentyl]amino]-4-(ethoxycarbonyl)benzenepropanoate |
| 69 B (BOP) | Et | 4-Br-C₆H₄- | C: H: N: | C: H: N: | 475 | $C_{22}H_{26}N_3O_3Br$ ethyl β-[[5-[4-(aminoiminomethyl)phenyl]-1-oxopentyl]amino]-4-bromobenzenepropanoate |
| 70 B (BOP) | Et | 4-Cl-C₆H₄- | C: 53.38 H: 5.51 N: 7.47 | C: 53.62 H: 5.69 N: 7.64 | 431 | $C_{23}H_{26}N_2O_3Cl$ ethyl β-[[5-[4-(aminoiminomethyl)phenyl]-1-oxopentyl]amino]-4-chlorobenzenepropanoate |
| 71 A | Et | -CH(CH₃)₂ (isopropyl) | C: 56.22 H: 7.02 N: 8.55 | C: 56.17 H: 7.02 N: 8.55 | | $C_{21}H_{23}N_3O_3 \cdot 1.0 CF_3CO_2H \cdot 0.1 H_2O$ ethyl 3-[[5-[4-(aminoiminomethyl)phenyl]-1-oxopentyl]amino]-4-methylhexanoate |
| 72 A | Et | -(CH₂)₄-C₆H₅ | C: 61.58 H: 6.77 N: 7.43 | C: 61.55 H: 6.82 N: 7.35 | | $C_{27}H_{37}N_3O_3 \cdot 1.0 CF_3CO_2H$ (±)-ethyl β-[[5-[4-(aminoiminomethyl)phenyl]-1-oxopentyl]amino]benzeneheptanoate |
| 73 A | Et | -CH=CH₂ (vinyl) | C: 53.84 H: 6.24 N: 8.97 | C: 54.00 H: 6.07 N: 8.91 | | $C_{19}H_{27}N_3O_3 \cdot 1.0 CF_3CO_2H \cdot 0.5 H_2O$ ethyl 3-[[5-[4-(aminoiminomethyl)phenyl]-1-oxopentyl]amino]-4-pentenoate |
| 74 A | Et | -CH₂-C₆H₅ | C: 55.86 H: 5.64 N: 7.24 | C: 56.09 H: 5.76 N: 7.27 | | $C_{24}H_{31}N_3O_3 \cdot 1.5 CF_3CO_2H$ ethyl β-[[5-[4-(aminoiminomethyl)phenyl]-1-oxopentyl]amino]benzenebutanoate |

TABLE A-continued

Structure: 4-amidinophenyl-(CH$_2$)$_4$-C(=O)-NH-CH(R$_2$)-CH$_2$-C(=O)-OR$_1$

| Example Method | R$_1$ | R$_2$ | Theory | Found | Mass Spectrum | |
|---|---|---|---|---|---|---|
| 75 A | Et | -CH$_2$-C$_6$H$_4$-Ph (4-biphenyl) | C: 64.66<br>H: 7.00<br>N: 7.80 | C: 64.28<br>H: 6.54<br>N: 8.20 | | C$_{29}$H$_{33}$N$_3$O$_3$.1HCl.1.7H$_2$O<br>ethyl β-[[5-[4-(aminoiminomethyl)phenyl]-1-oxopentyl]amino][1,1'-biphenyl]-4-propanoate |
| 76 A | H | -CH$_2$-C$_6$H$_5$ | C: 61.26<br>H: 6.75<br>N: 8.93 | C: 61.60<br>H: 7.03<br>N: 8.99 | | C$_{23}$H$_{29}$N$_3$O$_3$.0.5CF$_3$CO$_2$H.1H$_2$O<br>β-[[5-[4-(aminoiminomethyl)phenyl]-1-oxopentyl]amino]benzenepentanoic acid |
| 77 A | H | -CH(CH$_3$)$_2$·  isobutyl | C: 55.21<br>H: 7.62<br>N: 9.66 | C: 55.35<br>H: 7.89<br>N: 9.65 | | C$_{19}$H$_{29}$N$_3$O$_3$.0.5CF$_3$CO$_2$H.1.7H$_2$O<br>3-[[5-[4-(aminoiminomethyl)phenyl]-1-oxopentyl]amino]-5-methylhexanoic acid |
| 78 A | H | -(CH$_2$)$_3$-Ph | C: 62.81<br>H: 7.59<br>N: 8.79 | C: 62.98<br>H: 7.64<br>N: 8.51 | | C$_{28}$H$_{33}$N$_3$O$_3$.1HCl.1H$_2$O<br>β-[[5-[4-(aminoiminomethyl)phenyl]-1-oxopentyl]amino]benzeneheptanoic acid |
| 79 A | H | -CH$_2$-CH=CH$_2$ | C: 51.82<br>H: 5.72<br>N: 9.54 | C: 51.90<br>H: 5.49<br>N: 9.57 | | C$_{17}$H$_{23}$N$_3$O$_3$.1.0CF$_3$CO$_2$H.0.5H$_2$O<br>3-[[5-[4-(aminoiminomethyl)phenyl]-1-oxopentyl]amino]-4-pentenoic acid |
| 80 B (DSC) | H | -CH$_2$-(2-naphthyl) | C:<br>H:<br>N: | C:<br>H:<br>N: | 432 | C$_{26}$H$_{29}$N$_3$O$_3$<br>βR-[[5-[4-(aminoiminomethyl)phenyl]-1-oxopentyl]amino]-1-naphthalenebutanoic acid |
| 81 A | H | -CH$_3$ | C:<br>H:<br>N: | C:<br>H:<br>N: | 320 | C$_{17}$H$_{25}$N$_3$O$_3$<br>3-[[5-[4-(aminoiminomethyl)phenyl]-1-oxopentyl]amino]pentanoic acid |
| 82 A | Et | -CH$_3$ | C: 53.61<br>H: 6.64<br>N: 8.93 | C: 53.66<br>H: 6.48<br>N: 8.80 | | C$_{19}$H$_{29}$N$_3$O$_3$.1.0CF$_3$CO$_2$H.0.5H$_2$O<br>ethyl 3-[[5-[4-(aminoiminomethyl)phenyl]-1-oxopentyl]amino]pentanoate |
| 83 B (DSC) | Et | 2-chloro-6-fluorophenyl | C:<br>H:<br>N: | C:<br>H:<br>N: | 420 | C$_{21}$H$_{23}$N$_3$O$_3$ClF<br>ethyl β-[[5-[4-(aminoiminomethyl)phenyl]-1-oxopentyl]amino]-2-chloro-6-fluorobenzenepropanoate |
| 84 A | H | -CH$_2$-C$_6$H$_4$-OCH$_3$ (4-methoxy) | C: 59.06<br>H: 6.94<br>N: 8.98 | C: 59.33<br>H: 6.96<br>N: 8.63 | | C$_{23}$H$_{29}$N$_3$O$_4$<br>β-[[5-[4-(aminoiminomethyl)phenyl]-1-oxopentyl]amino]-4-methoxybenzenebutanoic acid |

EXAMPLE 85

Preparation of 3-[[5-[4-(aminoiminomethyl)phenyl]-1-oxo-4-pentynyl]amino]butanoic acid

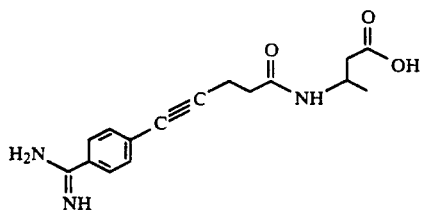

The title compound was prepared in the manner of Example 1 with the following modifications: Substituting 5-(p-cyanophenyl)-4-pentynoic acid for 5-(p-cyanophenyl)pentanoic acid and 3-methyl-beta-alanine for 3-phenyl-beta-alanine in procedure C of Example 1. The product was verified by C NMR (CD$_3$OD) delta 15.5, 20.3, 34.5, 40.8, 42.0, 80.3, 92.2, 126.1, 127.8 131.2, 133.5, 166.7, 169.7, 172.5.

The platelet-binding inhibitor activity of the representative of the present invention can be demonstrated by the assays presented below.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129 M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets per ml. 400 μl of the PRP preparation and 50 μl of the compound to be tested or saline were preincubated for 1 minute at 37° C. in a BioData aggregometer (BioData, Horsham, Pa.). 50 μl of adenosine 5'diphosphate (ADP) (50 μm final concentration) was added to the cuvettes and the aggregation was monitored for 1 minute. All compounds are tested in duplicate. Results are calculated as follows:

Percent of control=[(maximal OD minus initial OD of compound) divided by (maximal OD minus initial OD of control saline)]×100. The % inhibition=100−(percent of control).

The compounds tested and their median inhibitory concentrations (IC$_{50}$) are recorded in Table B. IC$_{50}$'s (if a compound showed 50% inhibition) were calculated by linear regression of the dose response curve. The assay results for the representative compounds of the present invention are set forth in Table B.

INHIBITION OF EX VIVO COLLAGEN INDUCED AGGREGATION BY COMPOUNDS OF THE INVENTION

PURPOSE

The purpose of this assay is to determine the effects of antiplatelet compounds on ex vivo collagen induced platelet aggregation when administered either intravenously or orally to dogs.

Pretreatment (control) blood samples are drawn from either conscious or anesthetized dogs (Beagles) and centrifuged to prepare platelet rich plasma (PRP). Aggregatory response to collagen is measured in an aggregometer and used as Control. Compounds are administered, either intragasterically (either by capsule or stomach tube or intravenously. Blood samples are drawn at predetermined intervals after compound administration, PRP prepared and aggregation to collagen determined. Compound inhibition of aggregation is determined by comparing the aggregation response after compound administration to the pretreatment response. The study is continued for a maximum of 24 hours or until the platelet aggregation returns to control levels. (If aggregation is still inhibited after 7 hours, a blood sample is drawn the following morning and tested.) Duration of activity is determined by the length of time platelet aggregation is inhibited after compound administration. The assay results for representative compounds of the present invention in the aforementioned Assay are set forth in Table B.

In Table B the designation "NT" means "Not Tested". Also in Table B, two readings given in a single box indicate that two trials, rather than a single trial, were run for that particular compound in that particular assay.

TABLE B

| Compound | IN-VITRO PLATELET AGGREGATION IN PRP | | | EX-VIVO COLLAGEN INDUCED AGGREGATION | | |
|---|---|---|---|---|---|---|
| | Dog PRP IC$_{50}$ Micro M | % Inhibition | Test Concentration | Dose Tested mg/Kg | Max % Inhibition | Duration Hours |
| β-[[5-[4-(aminoiminomethyl)phenyl]-1-oxopentyl]amino]benzenepropanoic acid, acetate salt | 5.3 | 100 | 1 × 10$^{-5}$ | 30 | 34 | <2 |
| ethyl β-[[5-[4-(aminoiminomethyl)phenyl]-1-oxopentyl]amino]benzenepropanoate | 5.3 | 90 | 1 × 10$^{-5}$ | 10<br>30 | 83<br>100 | >5 < 24<br>>24 |
| 3-[[5-[4-(aminoiminomethyl)phenyl]-1-oxopentyl]amino]butanoic acid | 1.2 | 100 | 1 × 10$^{-5}$ | 10 | 80 | 5 |
| ethyl 3-[[5-[4-(aminoiminomethyl)phenyl]-1-oxopentyl]amino]butanoate | 5.0 | 78 | 1 × 10$^{-5}$ | 10<br>30 | 90<br>100 | >5 < 24<br>>24 |
| β-[[5-[4-(aminoiminomethyl)phenyl]-1-oxopentyl]amino][1,1'-biphenyl]-4-propanoic acid, acetate salt | 2.3 | 100 | 1 × 10$^{-5}$ | NT | NT | NT |
| N-[5-[4-(aminoiminomethyl)phenyl]-1-oxopentyl]-2-hydroxy-β-alanine | 10.0 | 89 | 1 × 10$^{-5}$ | NT | NT | NT |
| N-[5-[4-(aminoiminomethyl)phenyl]-1- | 5.0 | 3 | 1 × 10$^{-6}$ | NT | NT | NT |

TABLE B-continued

| | IN-VITRO PLATELET AGGREGATION IN PRP | | | EX-VIVO COLLAGEN INDUCED AGGREGATION | | |
|---|---|---|---|---|---|---|
| Compound | Dog PRP $IC_{50}$ Micro M | % Inhibition | Test Concentration | Dose Tested mg/Kg | Max % Inhibition | Duration Hours |
| oxopentyl]-β-alanine, phenylmethyl ester | | | | | | |
| N-[5-[4-(aminoiminomethyl)phenyl]-1-oxopentyl]-2-fluoro-β-alanine | 30.0 | 10 | $1 \times 10^{-5}$ | NT | NT | NT |
| β-[[5-[4-(aminoiminomethyl)phenyl]-1-oxopentyl]amino]benzenebutanoic acid | 3.0 | 34 | $1 \times 10^{-6}$ | NT | NT | NT |
| N-[5-[4-(aminoiminomethyl)phenyl]-1-oxopentyl]-β-alanine | 6.0 | 19 | $1 \times 10^{-6}$ | NT | NT | NT |
| ethyl 3-[[5-[4-(aminoiminomethyl)phenyl]-1-oxopentyl]amino]-4-pentenoate | | 9 | $1 \times 10^{-5}$ | 30 | 100 | >6 <24 |
| βR-[[5-[4-(aminoiminomethyl)phenyl]-1-oxopentyl]amino]-3-benzo[b]thiophenebutanoic acid | | 8 | $1 \times 10^{-5}$ | NT | NT | NT |
| βR-[[5-[4-(aminoiminomethyl)phenyl]-1-oxopentyl]amino]-1-naphthalenebutanoic acid | | 5 | $1 \times 10^{-5}$ | NT | NT | NT |
| ethyl 3-[[5-[4-(aminoiminomethyl)phenyl]-1-oxopentyl]amino]pentanoate | | 0 | $1 \times 10^{-5}$ | NT | NT | NT |
| ethyl β-[[5-[4-(aminoiminomethyl)phenyl]-1-oxopentyl]amino][1,1'-biphenyl]-4-propanoate | | 45 | $1 \times 10^{-5}$ | 30 | 0 | |
| ethyl 3-[[5-[4-(aminoiminomethyl)phenyl]-1-oxopentyl]amino]-5-methylhexanoate | | 5 | $1 \times 10^{-5}$ | 30 | 100 | >6 |
| β-[[5-[4-(aminoiminomethyl)phenyl]-1-oxopentyl]amino]-2,4-dichlorobenzenepropanoic acid | | 16 | $1 \times 10^{-5}$ | NT | NT | NT |
| ethyl β-[[5-[4-(aminoiminomethyl)phenyl]-1-oxopentyl]amino]-4-bromobenzenepropanoate | NT | NT | NT | NT | NT | NT |
| β-[[5-[4-(aminoiminomethyl)phenyl]-1-oxopentyl]amino]-4-bromobenzenepropanoic acid | 3.1 | 100 | $1 \times 10^{-5}$ | NT | NT | NT |
| ethyl β-[[5-[4-(aminoiminomethyl)phenyl]-1-oxopentyl]amino]-4-chlorobenzenepropanoate | NT | NT | NT | NT | NT | NT |
| β-[[5-[4-(aminoiminomethyl)phenyl]-1-oxopentyl]amino]-4-chlorobenzenepropanoic acid | 2.8 | 100 | $1 \times 10^{-5}$ | NT | NT | NT |
| ethyl β-[[5-[4-(aminoiminomethyl)phenyl]-1-oxopentyl]amino]benzenepentanoate | | 16 | $1 \times 10^{-5}$ | 30 | 0 | |
| (±)-β-[[5-[4-(aminoiminomethyl)phenyl]-1-oxopentyl]amino]-2-thiophenepropanoic acid | 1.7 | 100 | $1 \times 10^{-5}$ | NT | NT | NT |
| 3-[[5-[4-(aminoiminomethyl)phenyl]-1-oxopentyl]amino]-4-pentenoic acid | 9.2 | 100 | $1 \times 10^{-5}$ | NT | NT | NT |
| 3-[[5-[4-(aminoiminomethyl)phenyl]-1-oxopentyl]amino]-5-methylhexanoic acid | | 25 | $1 \times 10^{-5}$ | NT | NT | NT |
| β-[[5-[4-(aminoiminomethyl)phenyl]-1-oxopentyl]amino]benzenepentanoic acid | 3.0 | 100 | $1 \times 10^{-5}$ | NT | NT | NT |
| ethyl β-[[5-[4-(aminoiminomethyl)phenyl]-1-oxopentyl]amino]-4-(ethoxycarbonyl)benzenepropanoate | NT | NT | NT | NT | NT | NT |
| β-[[5-[4-(aminoiminomethyl)phenyl]-1-oxopentyl]amino]-4-carboxybenzenepropanoic acid | 1.3 | 100 | $1 \times 10^{-5}$ | NT | NT | NT |
| ethyl β-[[5-[4-(aminoiminomethyl)phenyl]-1-oxopentyl]amino]-4-(phenylmethoxy)benzenepropanoate | NT | NT | NT | NT | NT | NT |
| β-[[5-[4-(aminoiminomethyl)phenyl]-1-oxopentyl]amino]-4-(phenylmethoxy)benzenepropanoic acid | 1.2 | 100 | $1 \times 10^{-5}$ | NT | NT | NT |
| ethyl β-[[5-[4-aminoiminomethyl)phenyl]-1-oxopentyl]amino]-3,5-dichlorobenzenepropanoate | NT | NT | NT | NT | NT | NT |
| β-[[5-[4-(aminoiminomethyl)phenyl]-1-oxopentyl]amino]-3,5-dichlorobenzenepropanoic acid | 6.0 | 100 | $1 \times 10^{-5}$ | NT | NT | NT |
| β-[[5-[4-(aminoiminomethyl)phenyl]-1-oxopentyl]amino]-2,6-dichlorobenzenepropanoic acid | | 9 | $1 \times 10^{-5}$ | NT | NT | NT |
| ethyl β-[[5-[4-(aminoiminomethyl)phenyl]-1-oxopentyl]amino]-3,4-dichlorobenzenepropanoate | NT | NT | NT | NT | NT | NT |
| β-[[5-[4-(aminoiminomethyl)phenyl]-1-oxopentyl]amino]-3,4-dichlorobenzenepropanoic acid | 6.8 | 100 | $1 \times 10^{-5}$ | NT | NT | NT |
| β-[[5-[4-(aminoiminomethyl)phenyl]-1-oxopentyl]amino]-2-chloro-6- | | 4 | $1 \times 10^{-5}$ | NT | NT | NT |

TABLE B-continued

| Compound | IN-VITRO PLATELET AGGREGATION IN PRP | | | EX-VIVO COLLAGEN INDUCED AGGREGATION | | |
|---|---|---|---|---|---|---|
| | Dog PRP $IC_{50}$ Micro M | % Inhibition | Test Concentration | Dose Tested mg/Kg | Max % Inhibition | Duration Hours |
| fluorobenzenepropanoic acid | | | | | | |
| 3-[[5-[4-(aminoiminomethyl)phenyl]-1-oxo-4-pentynyl]amino]butanoic acid | | 0 | $1 \times 10^{-5}$ | NT | NT | NT |
| β-[[5-[4-(aminoiminomethyl)phenyl]-1-oxopentyl]amino]-3,4-dimethoxybenzenepropanoic acid | 0.53 | 100 | $1 \times 10^{-5}$ | NT | NT | NT |
| β-[[5-[4-(aminoiminomethyl)phenyl]-1-oxopentyl]amino]-4-phenoxybenzenepropanoic acid | 2.0 | 100 | $1 \times 10^{-5}$ | NT | NT | NT |
| β-[[5-[4-(aminoiminomethyl)phenyl]-1-oxopentyl]amino]-3-fluorobenzenepropanoic acid | 1.3 | 97 | $1 \times 10^{-5}$ | NT | NT | NT |
| β-[[5-[4-(aminoiminomethyl)phenyl]-1-oxopentyl]amino]-3-methoxybenzenepropanoic acid | 1.3 | 100 | $1 \times 10^{-5}$ | NT | NT | NT |
| β-[[5-[4-(aminoiminomethyl)phenyl]-1-oxopentyl]amino]-3,5-dimethoxybenzenepropanoic acid | 0.33 | 94 | $1 \times 10^{-5}$ | NT | NT | NT |
| β-[[5-[4-(aminoiminomethyl)phenyl]-1-oxopentyl]amino]-3-cyclohexene-1-propanoic acid | 4.0 | 87 | $1 \times 10^{-5}$ | NT | NT | NT |
| β-[[5-[4-(aminoiminomethyl)phenyl]-1-oxopentyl]amino]-4-cyanobenzenepropanoic acid | 1.3 | 97 | $1 \times 10^{-5}$ | NT | NT | NT |
| β-[[5-[4-(aminoiminomethyl)phenyl]-1-oxopentyl]amino]-2,4-dimethoxybenzenepropanoic acid | 2.5 | 97 | $1 \times 10^{-5}$ | NT | NT | NT |
| β-[[5-[4-(aminoiminomethyl)phenyl]-1-oxopentyl]amino]-3-phenoxybenzenepropanoic acid | 5.1 | 89 | $1 \times 10^{-5}$ | NT | NT | NT |
| ethyl β-[[5-[4-(aminoiminomethyl)phenyl]-1-oxopentyl]amino]-3,4-dimethoxybenzenepropanoate | NT | NT | NT | NT | NT | NT |
| ethyl β-[[5-[4-(aminoiminomethyl)phenyl]-1-oxopentyl]amino]-3,5-dimethoxybenzenepropanoate | | 4 | $1 \times 10^{-5}$ | 20 | 70 | 4 |
| ethyl β-[[5-[4-(aminoiminomethyl)phenyl]-1-oxopentyl]amino]-4-phenoxybenzenepropanoate | NT | NT | NT | NT | NT | NT |
| ethyl β-[[5-[4-(aminoiminomethyl)phenyl]-1-oxopentyl]amino]-2,4-dimethoxybenzenepropanoate | NT | NT | NT | NT | NT | NT |
| β-[[5-[4-(aminoiminomethyl)phenyl]-1-oxopentyl]amino]-3-phenoxybenzenepropanoate | NT | NT | NT | NT | NT | NT |
| ethyl β-[[5-[4-(aminoiminomethyl)phenyl]-1-oxopentyl]amino]-4-ethoxybenzenepropanoate | | 9 | $1 \times 10^{-5}$ | 20 | 0 | 0 |
| ethyl β-[[5-[4-(aminoiminomethyl)phenyl]-1-oxopentyl]amino]-4-cyanobenzenepropanoate | NT | NT | NT | NT | NT | NT |
| ethyl β-[[5-[4-(aminoiminomethyl)phenyl]-1-oxopentyl]amino]-3-fluorobenzenepropanoate | NT | NT | NT | NT | NT | NT |
| β-[[5-[4-(aminoiminomethyl)phenyl]-1-oxopentyl]amino]-4-ethoxybenzenepropanoic acid | 0.40 | 100 | $1 \times 10^{-5}$ | NT | NT | NT |
| β-[[5-[4-(aminoiminomethyl)phenyl]-1-oxopentyl]amino]-4-fluorobenzenepropanoic acid | 3.0 | 100 | $1 \times 10^{-5}$ | NT | NT | NT |
| β-[[5-[4-(aminoiminomethyl)phenyl]-1-oxopentyl]amino]-2,5-dimethoxybenzenepropanoic acid | 9.0 | 95 | $1 \times 10^{-5}$ | NT | NT | NT |
| β-[[5-[4-(aminoiminomethyl)phenyl]-1-oxopentyl]amino]-2-fluorobenzenepropanoic acid | 5.2 | 82 | $1 \times 10^{-5}$ | NT | NT | NT |
| β-[[5-[4-(aminoiminomethyl)phenyl]-1-oxopentyl]amino]-3-pyridinepropanoic acid | 0.12 | 100 | $1 \times 10^{-5}$ | NT | NT | NT |
| β-[[5-[4-(aminoiminomethyl)phenyl]-1-oxo-4-pentynyl]amino]benzenepropanoic acid | 1.8 | 100 | $1 \times 10^{-5}$ | NT | NT | NT |
| (±)-ethyl β-[[5-[4-(aminoiminomethyl)phenyl]-1-oxopentyl]amino]benzeneheptanoate | | 6 | $1 \times 10^{-5}$ | NT | NT | NT |
| β-[[-[4-(aminoiminomethyl)phenyl-1-oxopentyl]amino]-4-methoxybenzenebutanoic acid | | 5 | $1 \times 10^{-5}$ | NT | NT | NT |
| ethyl β-[[5-[4-(aminoiminomethyl)phenyl]- | | 25 | $1 \times 10^{-5}$ | 10 | 100 | >5 < 24 |

TABLE B-continued

| | IN-VITRO PLATELET AGGREGATION IN PRP | | | EX-VIVO COLLAGEN INDUCED AGGREGATION | | |
|---|---|---|---|---|---|---|
| Compound | Dog PRP IC$_{50}$ Micro M | % Inhibition | Test Concentration | Dose Tested mg/Kg | Max % Inhibition | Duration Hours |
| 1-oxopentyl]amino]-3-pyridinepropanoate | | | | 20 | 100 | >24 |
| β-[[5-[4-(aminoiminomethyl)phenyl]-1-oxopentyl]amino]benzeneheptanoic acid | 7.1 | 71 | $1 \times 10^{-5}$ | NT | NT | NT |
| ethyl β-[[5-[4-(aminoiminomethyl)phenyl]-1-oxopentyl]amino]benzenebutanoate | | 0 | $1 \times 10^{-5}$ | 20 | 30 | 1.5 |
| 3R-[[5-[4-(aminoiminomethyl)phenyl]-2-oxopentyl]amino]butanoic acid | 1.3 | 100 | $1 \times 10^{-5}$ | NT | NT | NT |
| β-[[5-[4-(aminoiminomethyl)phenyl]-1-oxopentyl]amino-2-hydroxybenzenepropanoic acid | 2.0 | 100 | $1 \times 10^{-5}$ | NT | NT | NT |
| β-[[5-[4-(aminoiminomethyl)phenyl]-1-oxopentyl]amino]cyclohexanepropanoic acid | | 43 | $1 \times 10^{-5}$ | NT | NT | NT |
| β-[[5-[4-(aminoiminomethyl)phenyl]-1-oxopentyl]amino]-1,3-benzodioxole-5-propanoic acid | 0.28 | 100 | $1 \times 10^{-5}$ | NT | NT | NT |
| β-[[5-[4-(aminoiminomethyl)phenyl]-1-oxopentyl]amino]-4-(trifluoromethyl)benzenepropanoic acid | 4.3 | 91 | $1 \times 10^{-5}$ | NT | NT | NT |
| β-[[5-[4-(aminoiminomethyl)phenyl]-1-oxopentyl]amino]-3-(trifluoromethyl)benzenepropanoic acid | 7.0 | 74 | $1 \times 10^{-5}$ | NT | NT | NT |
| 3-[[5-[4-(aminoiminomethyl)phenyl]-4-methylene-1-oxopentyl]amino]butanoic acid | | 39 | $1 \times 10^{-5}$ | NT | NT | NT |
| 3-[[5-[4-(aminoiminomethyl)phenyl]-4-methyl-1-oxopentyl]amino]butanoic acid | 1.25 | 100 | $1 \times 10^{-5}$ | NT | NT | NT |
| 3-[[5-[4-(aminoiminomethyl)phenyl]-1-oxopentyl]amino]pentanoic acid | | 4 | $1 \times 10^{-5}$ | NT | NT | NT |
| β-[[5-[4-(aminoiminomethyl)phenyl]-1-oxopentyl]amino]-3-cyanobenzenepropanoic acid | 1.4 | 100 | $1 \times 10^{-5}$ | NT | NT | NT |
| (±)-β-[[5-[4-(aminoiminomethyl)phenyl]-1-oxopentyl]amino]-2-hydroxy-4-methoxybenzenepropanoic acid | 0.69 | 100 | $1 \times 10^{-5}$ | NT | NT | NT |
| cyclohexyl β-[[5-[4-(aminoiminomethyl)phenyl]-1-oxopentyl]amino]-3-pyridinepropanoate | 2.3 | 100 | $1 \times 10^{-5}$ | 10 | 87 | 3 |
| 3-[1-[[5-[4-(aminoiminomethyl)phenyl]-1-oxopentyl]amino]-2-carboxyethyl]-1-methylpyridinium chloride | 5.8 | 91 | $1 \times 10^{-5}$ | NT | NT | NT |
| β-[[5-[4-(aminoiminomethyl)phenyl]-1-oxopentyl]amino]-N-hydroxybenzenepropanamide | | 25 | $1 \times 10^{-5}$ | NT | NT | NT |
| ethyl β-[[5-[4-(aminoiminomethyl)phenyl]-1-oxopentyl]amino]-2-pyridinepropanoate | NT | NT | NT | NT | NT | NT |
| β-[[5-[4-(aminoiminomethyl)phenyl]-1-oxopentyl]amino]-2-pyridinepropanoic acid | 2.3 | 100 | $1 \times 10^{-5}$ | NT | NT | NT |
| β-[[5-[4-(aminoiminomethyl)phenyl]-1-oxopentyl]amino]-4-hydroxybenzenepropanoic acid | 0.80 | 100 | $1 \times 10^{-5}$ | NT | NT | NT |
| 3-(aminoiminomethyl-β-[[5-[4-(aminoiminomethyl)phenyl]-1-oxopentyl]amino]benzenepropanoic acid | | 43 | $1 \times 10^{-5}$ | NT | NT | NT |
| 4-(aminoiminomethyl)-β-[[5-[4-(aminoiminomethyl)phenyl]-1-oxopentyl]amino]benzenepropanoic acid | 1.8 | 100 | $1 \times 10^{-5}$ | NT | NT | NT |
| ethyl β-[[5-[4-(aminoiminomethyl)phenyl]-1-oxopentyl]amino]-1,3-benzodioxole-5-propanoate | | 43 | $1 \times 10^{-5}$ | 10 | 100 | 5 |

What is claimed is:

1. A compound of the formula

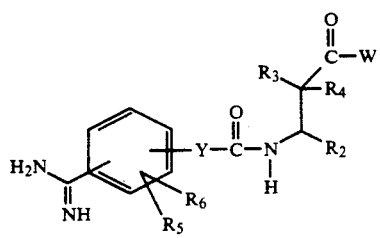

I or a pharmaceutically acceptable salt thereof, wherein W is the radical OR$_1$ wherein R$_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is hydrido, alkyl having 1 to 6 carbon atoms, alkenyl having 2 to 6 carbon atoms, cycloalkyl having 3 to 8 ring carbon atoms, cycloalkenyl having 5 or 6 ring carbon atoms and wherein any of said alkyl, said alkenyl, said cycloalkyl and said cycloalkenyl may be substituted with one or more groups selected from alkyl having 1 to 6 carbon atoms, alkoxy having 1 to 6 carbon atoms, halo and hydroxy; or $R_2$ is phenyl, phenylalkyl wherein the alkyl is $C_1$ to $C_6$, naphthyl, naphthylalkyl wherein the alkyl is $C_1$ to $C_6$, the group phenyl-Q-phenyl wherein Q is a direct single bond, or the group $O(R_7)_n$ wherein O represents oxygen and $R_7$ is an alkyl having 1 to 6 carbon atoms and n is the integer zero or one and wherein any of said phenyl, said phenylalkyl, said naphthyl and said naphthylalkyl ma be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carboxyl, alkyloxycarbonyl wherein the alkyl is $C_1$ to $C_6$ and aminoiminomethyl and wherein any one of the phenyl rings of the said phenyl-Q-phenyl group may be substituted with one or more groups selected from alkyl having 1 to 6 carbon atoms, alkoxy having 1 to 6 carbon atoms, trifluoromethyl and halo; or $R_2$ is a heteromonocyclic ring structure having 5 or 6 ring carbon atoms wherein 1 or 2 of the ring carbon atoms are replaced by nitrogen, oxygen or sulfur and wherein the ring is selected from saturated, partially unsaturated, and fully unsaturated rings or a fused bicyclic ring structure having 10 to 12 ring carbon atoms wherein 1 to 3 of the ring carbon atoms may be replaced by nitrogen, oxygen or sulfur and each ring may independently be saturated, partially unsaturated or fully unsaturated and wherein said heteromonocyclic ring structure and each ring of said fused bicyclic ring structure may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo;

2. A compound according to claim 1 of the formula

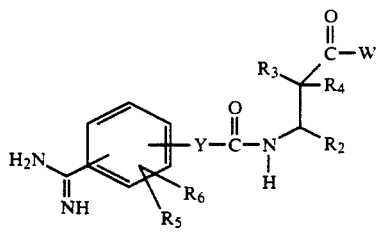

or a pharmaceutically acceptable salt thereof, wherein W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

is hydrido, alkyl having 1 to 6 carbon atoms, alkenyl having 2 to 6 carbon atoms, cycloalkyl having 3 to 8 ring carbon atoms or cycloalkenyl having 5 or 6 ring carbon atoms and wherein any of said alkyl, said alkenyl, said cycloalkyl and said cycloalkenyl may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms o carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be further substituted by one or more groups selected from alkyl having 1 to 6 carbon atoms, alkoxy having 1 to 6 carbon atoms, hydroxy and halo;

3. A compound according to claim 1 of the formula

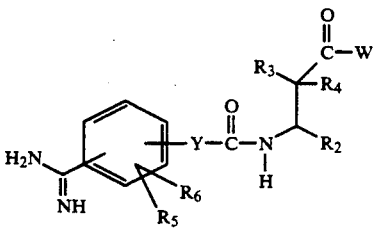

or a pharmaceutically acceptable salt thereof, wherein W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is phenyl, phenylalkyl wherein the alkyl is $C_1$ to $C_6$, naphthyl, naphthylalkyl wherein the alkyl is $C_1$ to $C_6$ or the group phenyl-Q-phenyl wherein Q is a direct single bond or the group $O(R_7)n$ wherein O represents oxygen and $R_7$ is an alkyl having 1 to 6 carbon atoms and n is the integer zero or one and wherein any of said phenyl, said phenylalkyl, said naphthyl and said naphthylalkyl may be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carboxyl, alkyloxycarbonyl wherein the alkyl is $C_1$ to $C_6$ and aminoiminomethyl and wherein any one of the phenyl rings of the said phenyl-Q-phenyl group may be substituted with one or more groups selected from alkyl having 1 to 6 carbon atoms, alkoxy having 1 to 6 carbon atoms, trifluoromethyl and halo;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl ma be further substituted by one or more groups selected from alkyl having 1 to 6 carbon atoms, alkoxy having 1 to 6 carbon atoms, hydroxy and halo;

4. A compound according to claim 1 of the formula

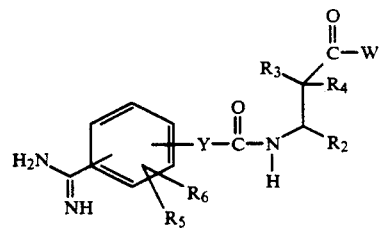

or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is a heteromonocyclic ring structure having 5 or 6 ring carbon atoms wherein 1 or 2 of the ring carbon atoms are replaced by nitrogen, oxygen or sulfur and wherein the ring is selected from saturated, partially unsaturated, and fully unsaturated rings or a fused bicyclic ring structure having 10 to 12 ring carbon atoms wherein 1 to 3 of the ring carbon atoms may be replaced by nitrogen, oxygen or sulfur and each ring may independently be saturated, partially unsaturated or fully unsaturated and wherein said heteromonocyclic ring structure and each ring of said fused bicyclic ring structure may be substituted with one or more groups selected from alkyl having 1 to 6 carbon atoms, alkoxy having 1 to 6 carbon atoms, halo and hydroxy;

$R_3$ and $R_4$ each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo.

5. A compound according to claim 2 of the formula

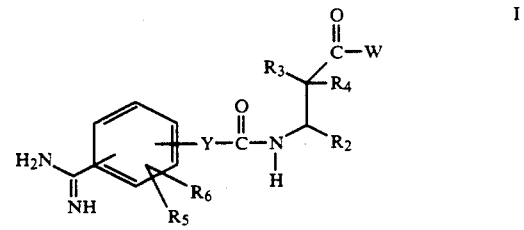

or a pharmaceutically acceptable salt thereof, wherein
W is the radical $OR_1$ wherein $R_1$ is hydrido, alkyl having 1 to 6 carbon atoms, or phenylalkyl wherein the alkyl is 1 to 6 carbon atoms and wherein any of said alkyl and said phenylalkyl may be substituted with one or more groups selected from alkyl having i to 6 carbon atoms, alkoxy having 1 to 6 carbon atoms, halo and hydroxy;

$R_2$ is hydrido, alkyl having 1 to 6 carbon atoms, alkenyl having 2 to 6 carbon atoms, cycloalkyl having 3 to 8 ring carbon atoms or cycloalkenyl having 5 or 6 ring carbon atoms and wherein any of said alkyl, said alkenyl, said cycloalkyl and said cycloalkenyl may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, or alkynyl having 2 to 6 carbon atoms wherein said alkyl, said alkenyl and said alkynyl may be substituted with one or more groups selected from alkyl having 1 to 6 carbon atoms, alkenyl having 2 to 6 carbon atoms, alkoxy having 1 to 6 carbon atoms, hydroxy and halo.

6. A compound according to claim 5 wherein "W" is the radical $OR_1$ wherein $R_1$ is hydrido or alkyl having 1 to 6 carbon atoms.

7. A compound according to claim 5 wherein $R_3$ and $R_4$ are each independently hydrido.

8. A compound according to claim 5 wherein "$R_5$ and $R_6$" are each independently hydrido.

9. A compound according to claim 5 wherein "Y" is alkyl having 1 to 6 carbon atoms.

10. A compound according to claim 5 which is N-[5-[4-(aminoiminomethyl)phenyl]-1-oxopentyl]-2-fluoro-β-alanine.

11. A compound according to claim 5 which is 3-[[5-[4-(aminoiminomethyl)phenyl]-1-oxopentyl]amino]-butanoic acid.

12. A compound according to claim 5 which is ethyl 3-[[5-[4-(aminoiminomethyl)phenyl]-1-oxopentyl-]amino]butanoate.

13. A compound according to claim 5 which is N-[5-[4-(aminoiminomethyl)phenyl]-1-oxopentyl]-2-hydroxy-β-alanine.

14. A compound according to claim 5 which is N-[5-[4-(aminoiminomethyl)phenyl]-1-oxopentyl]-β-alanine.

15. A compound according to claim 5 which is N-[5-[4-(aminoiminomethyl)phenyl]-1-oxopentyl]-β-alanine, phenylmethyl ester.

16. A compound according to claim 5 which is ethyl 3-[[5-[4-(aminoiminomethyl)phenyl]-1-oxopentyl-]amino]-4-pentenoate.

17. A compound according to claim 5 which is ethyl 3-[[5-[4-(a minoiminomethyl)phenyl]-1-oxopentyl-]amino]-5-methylhexanoate.

18. A compound according to claim 5 which is 3-[[5-[4-(aminoiminomethyl)phenyl]-1-oxopentyl]amino]-4-pentenoic acid.

19. A compound according to claim 5 which is 3-[[5-[4-(aminoiminomethyl)phenyl]-1-oxopentyl]amino]-5-methylhexanoic acid.

20. A compound according to claim 5 which is β-[[5-[4-(aminoiminomethyl)phenyl]-1-oxopentyl]amino]-3-cyclohexene-1-propanoic acid.

21. A compound according to claim 5 which is 3R-[[5-[4-(aminoiminomethyl)phenyl]-1-oxopentyl]amino]-butanoic acid.

22. A compound according to claim 5 which is β-[[5-[4-(aminoiminomethyl)phenyl]-1-oxopentyl]amino]cyclohexanepropanoic acid.

23. A compound according to claim 5 which is 3-[[5-[4-(aminoiminomethyl)phenyl]-4-methylene-1-oxopentyl]amino]butanoic acid.

24. A compound according to claim 5 which is 3-[[5-[4-(aminoiminomethyl)phenyl]-4-methyl-1-oxopentyl-]amino]butanoic acid.

25. A compound according to claim 5 which is 3-[[5-[4-(aminoiminomethyl)phenyl]-1-oxopentyl]amino]pentanoic acid.

26. A compound according to claim 3 of the formula

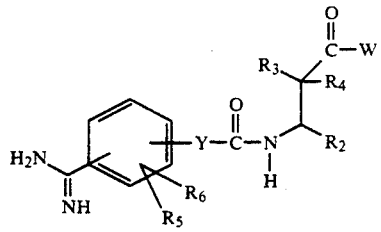

or a pharmaceutically acceptable salt thereof, wherein
W is the radical $OR_1$ wherein $R_1$ is hydrido, alkyl having 1 to 6 carbon atoms or the amino radical of the formula

NHOH;

wherein said alkyl may be substituted with one or more groups selected from alkyl having 1 to 6 carbon atoms, alkoxy having 1 to 6 carbon atoms, halo and hydroxy;

$R_2$ is phenyl, phenylalkyl wherein the alkyl is $C_1$ to $C_6$, naphthyl, naphthylalkyl wherein the alkyl is $C_1$ to $C_6$ or the group phenyl-Q-phenyl where Q is a direct single bond or the group $O(R_7)_n$ wherein O represents oxygen and $R_7$ is an alkyl having 1 to 6 carbon atoms and n is the integer zero or one and wherein any of said phenyl, said phenylalkyl, said naphthyl and said naphthylalkyl may be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carboxyl, alkyloxycarbonyl wherein the alkyl is $C_1$ to $C_6$ and aminoiminomethyl and wherein any one of the phenyl rings of the said phenyl-Q-phenyl group may be substituted with one or more groups selected from alkyl having 1 to 6 carbon atoms, alkoxy having 1 to 6 carbon atoms, trifluoromethyl and halo;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, or alkynyl having 2 to 6 carbon atoms wherein said alkyl, said alkenyl and said alkynyl may be substituted with one or more groups selected from alkyl having 1 to 6 carbon atoms, alkenyl having 2 to 6 carbon atoms, alkoxy having 1 to 6 carbon atoms, hydroxy and halo.

27. A compound according to claim 26 of the formula

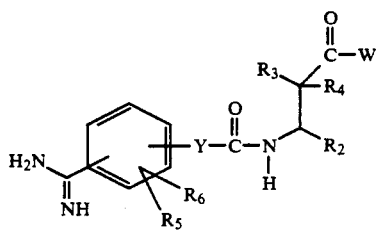

or a pharmaceutically acceptable salt thereof,

W is the radical $OR_1$ wherein $R_1$ is hydrido or alkyl having 1 to 6 carbon atoms;

$R_2$ is phenyl or phenylalkyl wherein said phenyl and said phenylalkyl may be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carbonyl, alkyloxycarbonyl wherein the alkyl is $C_1$ to $C_6$, and aminoiminomethyl;

$R_3$ and $R_4$ are each independently hydrido;

$R_5$ and $R_6$ are each independently hydrido; and

Y is alkyl having 1 to 6 carbon atoms.

28. A compound according to claim 26 wherein "W" is the radical $OR_1$ wherein $R_1$ is hydrido or alkyl having 1 to 6 carbon atoms.

29. A compound according to claim 26 wherein "$R_2$" is phenyl and phenylalkyl wherein said phenyl and said phenylalkyl may be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carboxyl, alkyloxycarbonyl wherein the alkyl is $C_1$ to $C_6$ and aminoiminomethyl.

30. A compound according to claim 26 wherein "$R_2$" is naphthyl or naphthylalkyl wherein the alkyl is $C_1$ to $C_6$.

31. A compound according to claim 26 wherein "$R_2$" is the group phenyl-Q-phenyl Wherein Q is a direct single bond or the group $O(R_7)_n$ wherein O represents oxygen, $R_7$ is an alkyl having 1 to 6 carbon atoms, and n is the integer zero or one.

32. A compound according to claim 26 wherein "$R_3$ and $R_4$" are each independently hydrido.

33. A compound according to claim 26 wherein "$R_5$ and $R_6$" are each independently hydrido.

34. A compound according to claim 26 wherein "Y" is alkyl having 1 to 6 carbon atoms.

35. A compound according to claim 27 which is β-[[5-[4-(aminoiminomethyl)phenyl]-1-oxopentyl]amino]-benzenepropanoic acid, acetate salt.

36. A compound according to claim 27 which is β-[[5-[4-(aminoiminomethyl)phenyl]-1-oxopentyl]amino]-benzenebutanoic acid.

37. A compound according to claim 27 which is ethyl β-[[5-[4-(aminoiminomethyl)phenyl]-1-oxopentyl]amino]benzenepropanoate.

38. A compound according to claim 27 which is ethyl β-[[5-[4-(aminoiminomethyl)phenyl]-1-oxopentyl]amino]-4-bromobenzenepropanoate.

39. A compound according to claim 27 which is β-[[5-[4-(aminoiminomethyl)phenyl]-1-oxopentyl]amino]-2,4-dichlorobenzenepropanoic acid.

40. A compound according to claim 27 which is β-[[5-[4-(aminoiminomethyl)phenyl]-1-oxopentyl]amino]-4-bromobenzenepropanoic acid.

41. A compound according to claim 27 which is ethyl β-[[5-[4-(aminoiminomethyl)phenyl]-1-oxopentyl]amino]-4-chlorobenzenepropanoate.

42. A compound according to claim 27 which is β-[[5-[4-(aminoiminomethyl)phenyl]-1-oxopentyl]amino]-4-chlorobenzenepropanoic acid.

43. A compound according to claim 27 which is ethyl β-[[5-[4-(aminoiminomethyl)phenyl]-1-oxopentyl]amino]benzenepentanoate.

44. A compound according to claim 27 which is β-[[5-[4-(aminoiminomethyl)phenyl]-1-oxopentyl]amino]-benzenepentanoic acid.

45. A compound according to claim 27 which is ethyl β-[[5-[4-(aminoiminomethyl)phenyl]-1-oxopentyl]amino]-4-(ethoxycarbonyl)benzenepropanoate.

46. A compound according to claim 27 which is β-[[5-[4-(aminoiminomethyl)phenyl]-1-oxopentyl]amino]-4-carboxybenzenepropanoic acid.

47. A compound according to claim 27 which is ethyl β-[[5-[4-(aminoiminomethyl)phenyl]-1-oxopentyl]amino]-3,5-dichlorobenzenepropanoate.

48. A compound according to claim 27 which is β-[[5-[4-(aminoiminomethyl)phenyl]-1-oxopentyl]amino]-3,5-dichlorobenzenepropanoic acid.

49. A compound according to claim 27 which is β-[[5-[4-(aminoiminomethyl)phenyl]-1-oxopentyl]amino]-2,6-dichlorobenzenepropanoic acid.

50. A compound according to claim 27 which is ethyl β-[[5-[4-(aminoiminomethyl)phenyl]-1-oxopentyl]amino]-3,4-dichlorobenzenepropanoate.

51. A compound according to claim 27 which is β-[[5-[4-(aminoiminomethyl)phenyl]-1-oxopentyl]amino]-3,4-dichlorobenzenepropanoic acid.

52. A compound according to claim 27 which is β-[[5-[4-(aminoiminomethyl)phenyl]-1-oxopentyl]amino]-2-chloro-6-fluorobenzenepropanoic acid.

53. A compound according to claim 27 which is β-[[5-[4-(aminoiminomethyl)phenyl]-1-oxopentyl]amino]-3,4-dimethoxybenzenepropanoic acid.

54. A compound according to claim 27 which is β-[[5-[4-(aminoiminomethyl)phenyl]-1-oxopentyl]amino]-3-fluorobenzenepropanoic acid.

55. A compound according to claim 27 which is β-[[5-[4-(aminoiminomethyl)phenyl]-1-oxopentyl]amino]-3-methoxybenzenepropanoic acid.

56. A compound according to claim 27 which is β-[[5-[4-(aminoiminomethyl)phenyl]-1-oxopentyl]amino]-3,5-dimethoxybenzenepropanoic acid.

57. A compound according to claim 27 which is β-[[5-[4-(aminoiminomethyl)phenyl]-1-oxopentyl]amino]-4-cyanobenzenepropanoic acid.

58. A compound according to claim 27 which is β-[[5-[4-(aminoiminomethyl)phenyl]-1-oxopentyl]amino]-2,4-dimethoxybenzenepropanoic acid.

59. A compound according to claim 27 which is ethyl β-[[5-[4-(aminoiminomethyl)phenyl]-1-oxopentyl]amino]-3,4-dimethoxybenzenepropanoate.

60. A compound according to claim 27 which is ethyl β-[[5-[4-(aminoiminomethyl)phenyl]-1-oxopentyl]amino]-3,5-dimethoxybenzenepropanoate.

61. A compound according to claim 27 which is ethyl β-[[5-[4-(aminoiminomethyl)phenyl]-1-oxopentyl]amino]-2,4-dimethoxybenzenepropanoate.

62. A compound according to claim 27 which is ethyl β-[[5-[4-(aminoiminomethyl)phenyl]-1-oxopentyl]amino]-4-ethoxybenzenepropanoate.

63. A compound according to claim 27 which is ethyl β-[[5-[4-(aminoiminomethyl)phenyl]-1-oxopentyl]amino]-4-cyanobenzenepropanoate.

64. A compound according to claim 27 which is ethyl β-[[5-[4-(aminoiminomethyl)phenyl]-1-oxopentyl]amino]-3-fluorobenzenepropanoate.

65. A compound according to claim 27 which is β-[[5-[4-(aminoiminomethyl)phenyl]-1-oxopentyl]amino]-4-ethoxybenzenepropanoic acid.

66. A compound according to claim 27 which is β-[[5-[4-(aminoiminomethyl)phenyl]-1-oxopentyl]amino]-4-fluorobenzenepropanoic acid.

67. A compound according to claim 27 which is β-[[5-[4-(aminoiminomethyl)phenyl]-1-oxopentyl]amino]-2,5-dimethoxybenzenepropanoic acid.

68. A compound according to claim 27 which is β-[[5-[4-(aminoiminomethyl)phenyl]-1-oxopentyl]amino]-2-fluorobenzenepropanoic acid.

69. A compound according to claim 26 which is β-[[5-[4-(aminoiminomethyl)phenyl]-1-oxo-4-pentynyl]amino]benzenepropanoic acid.

70. A compound according to claim 27 which is (+)-ethyl β-[[5-[4-(aminoiminomethyl)phenyl]-1-oxopentyl]amino]benzeneheptanoate.

71. A compound according to claim 27 which is β-[[5-[4-(aminoiminomethyl)phenyl]-1-oxopentyl]amino]-4-methoxybenzenebutanoic acid.

72. A compound according to claim 27 which is β-[[5-[4-(aminoiminomethyl)phenyl]-1-oxopentyl]amino]benzeneheptanoic acid.

73. A compound according to claim 27 which is ethyl β-[[5-[4-(aminoiminomethyl)phenyl]-1-oxopentyl]amino]benzenebutanoate.

74. A compound according to claim 27 which is (±)-β-[[5-[4-(aminoiminomethyl)phenyl]-1-oxopentyl]amino-2-hydroxybenzenepropanoic acid.

75. A compound according to claim 27 which is β-[[5-[4-(aminoiminomethyl)phenyl]-1-oxopentyl]amino]-4-(trifluoromethyl)benzenepropanoic acid.

76. A compound according to claim 27 which is β-[[5-[4-(aminoiminomethyl)phenyl]-1-oxopentyl]amino]-3-(trifluoromethyl)benzenepropanoic acid.

77. A compound according to claim 27 which is β-[[5-[4-(aminoiminomethyl)phenyl]-1-oxopentyl]amino]-3-cyanobenzenepropanoic acid.

78. A compound according to claim 27 which is (±)-β-[[5-[4-(aminoiminomethyl)phenyl]-1-oxopentyl]amino]-2-hydroxy-4methoxybenzenepropanoic acid.

79. A compound according to claim 26 which is β-[[5-4-(aminoiminomethyl)phenyl]-1-oxopentyl]amino]-N-hydroxybenzenepropanamide.

80. A compound according to claim 27 which is β-[[5-4-(aminoiminomethyl)phenyl]-1-oxopentyl]amino]-4hydroxybenzenepropanoic acid.

81. A compound according to claim 27 which is 3-(aminoiminomethyl)-β-[[5-[4-(aminoiminomethyl)-phenyl]-1oxopentyl]amino]benzenepropanoic acid.

82. A compound according to claim 27 which is 4-(aminoiminomethyl)-β-[[5-[4(aminoiminomethyl phenyl]-1oxopentyl]amino]benzenepropanoic acid.

83. A compound according to claim 30 which is βR-[[5-[4-(aminoiminomethyl)phenyl]-1-oxopentyl]amino]-1-naphthalenebutanoic acid.

84. A compound according to claim 31 which is ethyl β-[[5-[4-(aminoiminomethyl)phenyl]-1-oxopentyl]amino][1,1'-4-propanoate.

85. A compound according to claim 31 which is ethyl β-[[5-[4-(aminoiminomethyl)phenyl]-1-oxopentyl]amino]-4-(phenylmethoxy)benzenepropanoate.

86. A compound according to claim 31 which is β-[[5-[4-(aminoiminomethyl)phenyl]-1-oxopentyl]amino]-4-(phenylmethoxy)benzenepropanoic acid.

87. A compound according to claim 31 which is β-[[5-[4 (aminoiminomethyl)phenyl]-1-oxopentyl]amino]-4-phenoxybenzenepropanoic acid.

88. A compound according to claim 31 which is β-[[5-[4-(aminoiminomethyl)phenyl]-1-oxopentyl]amino]-3-phenoxybenzenepropanoic acid.

89. A compound according to claim 31 which is ethyl β-[[5-[4-(aminoiminomethyl)phenyl]-1-oxopentyl]amino]-4-phenoxybenzenepropanoate.

90. A compound according to claim 31 which is β-[[5-[4-(aminoiminomethyl)phenyl]-1-oxopentyl]amino]-3-phenoxybenzenepropanoate.

91. A compound according to claim 31 which is β-[[5-4-(aminoiminomethyl)phenyl]-1-oxopentyl]amino][1,1'-biphenyl]-4-propanoic acid, acetate salt.

92. A compound according to claim 4 of the formula

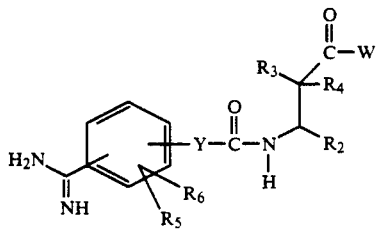

or a pharmaceutically acceptable salt thereof, wherein
W is the radical $OR_1$ wherein $R_1$ is hydrido, alkyl having 1 to 6 carbon atoms or cycloalkyl having 5 or 6 ring carbon atoms and wherein any of said alkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ a heteromonocyclic ring structure having 5 or 6 ring carbon atoms wherein 1 or 2 of the ring carbon atoms are replaced by nitrogen, oxygen or sulfur and wherein the ring is fully unsaturated or a fused bicyclic ring structure having 10 to 12 ring carbon atoms wherein 1 to 3 of the ring carbon atoms may be replaced by nitrogen, oxygen or sulfur and each ring may independently be saturated, partially unsaturated or fully unsaturated;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms.

93. A compound according to claim 92 wherein "$R_2$" is pyridinyl.

94. A compound according to claim 92 wherein "$R_2$" is thiophenyl.

95. A compound according to claim 92 wherein "$R_2$" is benzothiophenyl.

96. A compound according to claim 92 wherein "$R_2$" is benzodioxolyl.

97. A compound according to claim 92 wherein "$R_3$ and $R_4$" are each independently hydrido.

98. A compound according to claim 92 wherein "$R_5$ and $R_6$" are each independently hydrido.

99. A compound according to claim 93 which is β-[[5-[4-(aminoiminomethyl)phenyl]-1-oxopentyl]amino]-3-pyridinepropanoic acid.

100. A compound according to claim 93 which is ethyl β-[[5-[4-(aminoiminomethyl)phenyl]-1-oxopentyl]amino]-3-pyridinepropanoate.

101. A compound according to claim 93 which is cyclohexyl β-[[5-[4-(aminoiminomethyl)phenyl]-1-oxopentyl]amino]-3-pyridinepropanoate.

102. A compound according to claim 93 which is 3-[1-[[5-[4-(aminoiminomethyl)phenyl]-1-oxopentyl]amino]-2-carboxyethyl]-1-methylpyridinium chloride.

103. A compound according to claim 93 which is ethyl β-[[5-[4-(aminoiminomethyl)phenyl]-1-oxopentyl]amino]-2-pyridinepropanoate.

104. A compound according to claim 93 which is β-[[5-[4-(aminoiminomethyl)phenyl]-1-oxopentyl]amino]-2-pyridinepropanoic acid.

105. A compound according to claim 94 which is (±)-β-[[5-[4-(aminoiminomethyl)phenyl]-1-oxopentyl]amino]-2-thiophenepropanoic acid.

106. A compound according to claim 95 which is βR-[[5-[4-(aminoiminomethyl)phenyl]-1-oxopentyl]amino]-3-benzo[b]thiophenebutanoic acid.

107. A compound according to claim 95 which is ethyl βR-[[5-[4-(aminoiminomethyl)phenyl]-1-oxopentyl]amino]-3-benzo[b]thiophenebutanoate.

108. A compound according to claim 96 which is β-[[5-[4-(aminoiminomethyl)phenyl]-1-oxopentyl]amino]-1,3-benzodioxole-5-propanoic acid.

109. A compound according to claim 96 which is ethyl-β-[[5-[4-(aminoiminomethyl)phenyl]-1-oxopentyl]amino]-1-,3-benzodioxole-5-propanoate.

110. A pharmaceutical composition useful for inhibiting platelet aggregation comprising an effective amount of at least one compound according to claim 1, together with one or more non-toxic pharmaceutically acceptable carriers.

111. A pharmaceutical composition according to claim 110 wherein the compound has the formula

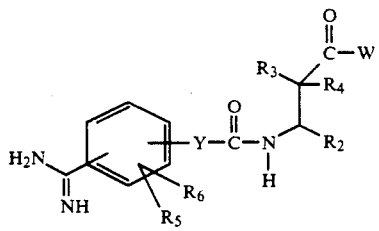

I or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is hydrido, alkyl having 1 to 6 carbon atoms, alkenyl having 2 to 6 carbon atoms, cycloalkyl having 3 to 8 ring carbon atoms or cycloalkenyl having 5 or 6 ring carbon atoms and wherein any of said alkyl, said alkenyl, said cycloalkyl and said cycloalkenyl may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be further substituted by one or more groups selected from alkyl having 1 to 6 carbon atoms, alkoxy having 1 to 6 carbon atoms, hydroxy and halo.

112. A pharmaceutical composition according to claim 110 wherein the compound has the formula

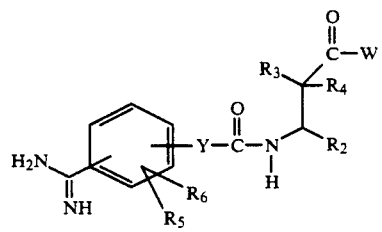

I or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is phenyl, phenylalkyl wherein the alkyl is $C_1$ to $C_6$, naphthyl, naphthylalkyl wherein the alkyl is $C_1$ to $C_6$ or the group phenyl-Q-phenyl wherein Q is a direct single bond or the group $O(R_7)_n$ wherein O represents oxygen and $R_7$ is an alkyl having 1 to 6 carbon atoms and n is the integer zero or one and wherein any of said phenyl, said phenylalkyl, said naphthyl and said naphthylalkyl may be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carboxyl, alkyloxycarbonyl wherein the alkyl is $C_1$ to $C_6$ and aminoiminomethyl and wherein any one of the phenyl rings of the said phenyl-Q-phenyl group may be substituted with one or more groups selected from alkyl having 1 to 6 carbon atoms, alkoxy having 1 to 6 carbon atoms, trifluoromethyl and halo;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo.

113. A pharmaceutical composition according to claim 110 wherein the compound has the formula

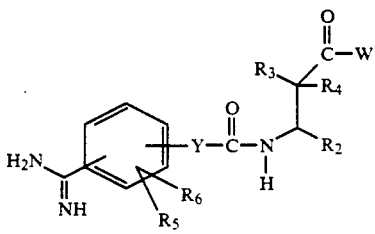

or a pharmaceutically acceptable salt thereof, wherein

W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is a heteromonocyclic ring structure having 5 or 6 ring carbon atoms wherein 1 or 2 of the ring carbon atoms are replaced by nitrogen, oxygen or sulfur and wherein the ring is selected from saturated, partially unsaturated, and fully unsaturated rings or a fused bicyclic ring structure having 10 to 12 ring carbon atoms wherein 1 to 3 of the ring carbon atoms may be replaced by nitrogen, oxygen or sulfur and each ring may independently be saturated, partially unsaturated or fully unsaturated and wherein said heteromonocyclic ring structure and each ring of said fused bicyclic ring structure may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo.

114. A pharmaceutical composition according to claim 111 wherein the compound is 3-[[5-[4-(aminoiminomethyl)phenyl]-1-oxopentyl]amino]butanoic acid.

115. A pharmaceutical composition according to claim 111 wherein the compound is ethyl 3-[[5-[4-(aminoiminomethyl) phenyl]-1-oxopentyl]amino]butanoate.

116. A pharmaceutical composition according to claim 111 wherein the compound is 3R-[[5-[4-(aminoiminomethyl) phenyl]-1-oxopentyl amino]butanoic acid.

117. A pharmaceutical composition according to claim 111 wherein the compound is β-[[5-[4-(aminoiminomethyl)phenyl]-1-oxopentyl]-3-cyclohexene-1-propanoic acid.

118. A pharmaceutical composition according to claim 111 wherein the compound is ethyl 3-[[5-[4-(aminoiminomethyl)phenyl]-1-oxopentyl]amino]-4pentenoate.

119. A pharmaceutical composition according to claim 111 wherein the compound is 3-[[5-[4-(aminoiminomethyl)phenyl]-4-methylene-1-oxopentyl]amino]butanoic acid.

120. A pharmaceutical composition according to claim 111 wherein the compound is 3-[[5-[4-(aminoiminomethyl)phenyl]-4-methyl-1-oxopentyl]amino]butanoic acid.

121. A pharmaceutical composition according to claim 112 wherein the compound is ethyl β-[[5-[4-(aminoiminomethyl)phenyl]-1- oxopentyl]amino] benzenepropanoate.

122. A pharmaceutical composition according to claim 112 wherein the compound is β-[[5-[4-(aminoiminomethyl)phenyl]-1-oxopentyl]amino]benzenepropanoic acid, acetate salt.

123. A pharmaceutical composition according to (aminoiminomethyl)phenyl]-1-oxopentyl]amino]-4-ethoxybenzenepropanoic acid.

124. A pharmaceutical composition according to claim 112 wherein the compound is ethyl β-[[5-[4-(aminoiminomethyl)phenyl]-1-oxopentyl]amino]-4ethoxybenzenepropanoate.

125. A pharmaceutical composition according to claim 112 wherein the compound is β-[[5-[4-(aminoiminomethyl)phenyl]-1-oxopentyl]amino]-4-cyanobenzenepropanoic acid.

126. A pharmaceutical composition according to claim 112 wherein the compound is β-[[5-[4-(aminoiminomethyl)-phenyl]-1-oxopentyl]amino]-4-fluorobenzenepropanoic acid.

127. A pharmaceutical composition according to claim 112 wherein the compound is β-[[5-[4[(aminoiminomethyl)phenyl]-1-oxo-4-pentynyl]amino]benzenepropanoic acid.

128. A pharmaceutical composition according to claim 112 wherein the compound is β-[[5-[4-(aminoiminomethyl)phenyl]-1-oxopentyl]amino]-N-hydroxybenzenepropanamide.

129. A pharmaceutical composition according to claim 113 wherein the compound is β-[[5-[4-

(aminoiminomethyl)phenyl]-1-oxopentyl]amino]-3-pyridinepropanoic acid.

130. A pharmaceutical composition according to claim 113 wherein the compound is ethyl β-[[5-[4-(aminoiminomethyl)phenyl]-1-oxopentyl]amino]-3-pyridinepropanoate.

131. A pharmaceutical composition according to claim 113 wherein the compound is β-[[5-[4-(aminoiminomethyl)phenyl]-1-oxopentyl]amino]-1,3-benzodioxole-5-propanoic acid.

132. A pharmaceutical composition according to claim 113 wherein the compound is ethyl β-[[5-[4-(aminoiminomethyl)phenyl] -1-oxopentyl]amino]-1,3-benzodioxole-5-propanoate.

133. A pharmaceutical composition according to claim 113 wherein the compound is β-[[5-[4-(aminoiminomethyl)phenyl]-1-oxopentyl]amino]-2-pyridinepropanoic acid.

134. A method of treating a mammal to inhibit platelet aggregation comprising administering a therapeutically effective dose of at least one compound of claim 1 to a mammal in need of such treatment.

135. A method of treating a mammal to inhibit platelet aggregation according to claim 134, comprising administering a therapeutically effective dose of a compound of the formula

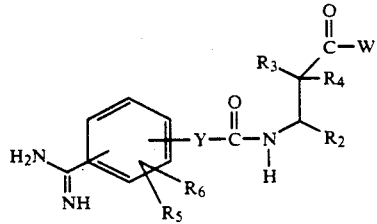

I or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is hydrido, alkyl having 1 to 6 carbon atoms, alkenyl having 2 to 6 carbon atoms, cycloalkyl having 3 to 8 ring carbon atoms or cycloalkenyl having 5 or 6 ring carbon atoms and wherein any of said alkyl, said alkenyl, said cycloalkyl and said cycloalkenyl may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo.

136. A method of treating a mammal to inhibit platelet aggregation according to claim 134, comprising administering a therapeutically effective dose of a compound of the formula

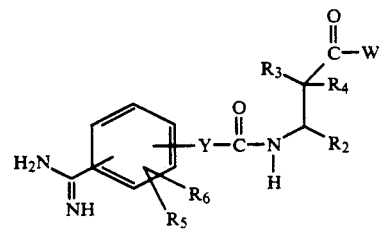

I or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is phenyl, phenylalkyl wherein the alkyl is $C_1$ to $C_6$, naphthyl, naphthylalkyl wherein the alkyl is $C_1$ to $C_6$ or the group phenyl-Q-phenyl wherein Q is a direct single bond or the group $O(R_7)_n$ wherein O represents oxygen and $R_7$ is an alkyl having 1 to 6 carbon atoms and n is the integer zero or one and wherein any of said phenyl, said phenylalkyl, said naphthyl and said naphthylalkyl may be substituted with one or more groups selected from alkyl having 1 to 6 carbon atoms, alkoxy having 1 to 6 carbon atoms, halo, trifluoromethyl, hydroxy, nitro, cyano, sulfonyl, sulfonylalkyl having 1 to 6 carbon atoms, carboxyl, alkyloxycarbonyl wherein the alkyl is $C_1$ to $C_6$ and aminoiminomethyl and wherein any one of the phenyl rings of the said phenyl-Q-phenyl group may be substituted with one or more groups selected from alkyl having 1 to 6 carbon atoms, alkoxy having 1 to 6 carbon atoms, trifluoromethyl and halo;

$R_3$ and $R_4$ are each independently selected from hydrido, alkyl having i to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be further substituted by one or more groups selected from alkyl having 1 to 6 carbon atoms, alkoxy having 1 to 6 carbon atoms, hydroxy and halo;

137. A method of treating a mammal to inhibit platelet aggregation according to claim 134, comprising administering a therapeutically effective dose of a compound of the formula

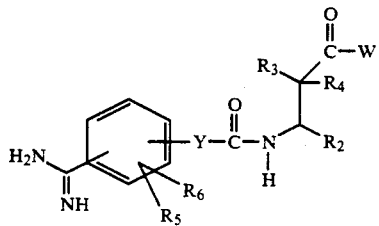

I or a pharmaceutically acceptable salt thereof, wherein
W is the radical $OR_1$ wherein $R_1$ is hydrido, alkyl having 1 to 6 carbon atoms, phenyl, phenylalkyl wherein the alkyl is 1 to 6 carbon atoms or cycloalkyl and wherein any of said alkyl, said phenyl said phenylalkyl and said cycloalkyl may be substituted with one or more groups selected from alkyl having 1 to 6 carbon atoms, alkoxy having 1 to 6 carbon atoms, halo and hydroxy; or W is the amino radical of the formula

NHOH;

$R_2$ is a heteromonocyclic ring structure having 5 or 6 ring carbon atoms wherein 1 or 2 of the ring carbon atoms are replaced by nitrogen, oxygen or sulfur and wherein the ring is selected from saturated, partially unsaturated, and fully unsaturated rings or a fused bicyclic ring structure having 10 to 12 ring carbon atoms wherein 1 to 3 of the ring carbon atoms may be replaced by nitrogen, oxygen or sulfur and each ring may independently be saturated, partially unsaturated or fully unsaturated and wherein said heteromonocyclic ring structure and each ring of said fused bicyclic ring structure may be substituted with one or more groups selected from alkyl having 1 to 6 carbon atoms, alkoxy having 1 to 6 carbon atoms, halo and hydroxy;

$R_3$ and $R_4$ are each independently selected from hydrido, alkyl having 1 to 6 carbon atoms, hydroxy and halo;

$R_5$ and $R_6$ are each independently selected from hydrido, alkyl having 1 to 6 carbon atoms, hydroxy, halo and alkoxy having 1 to 6 carbon atoms; and Y is alkyl having 1 to 6 carbon atoms, alkenyl having 2 to 6 carbon atoms, alkynyl having 2 to 6 carbon atoms or carbonylalkyl wherein the alkyl group is $C_1$ to $C_6$ and wherein any said alkyl, said alkenyl, said alkynyl and said carbonylalkyl may be substituted with one or more groups selected from alkyl having 1 to 6 carbon atoms, alkenyl having 2 to 6 carbon atoms, alkoxy having 1 to 6 carbon atoms, hydroxy, halo and phenyl wherein the phenyl may be substituted by one or more groups selected from alkyl having 1 to 6 carbon atoms, alkoxy having 1 to 6 carbon atoms, hydroxy and halo.

138. A method according to claim 135 wherein the compound is ethyl 3-[[5-[4-(aminoiminomethyl) phenyl]-1-oxopentyl]amino]butanoate.

139. A method according to claim 135 wherein the compound is 3-[[5-[5-(aminoiminomethyl)phenyl]-1-oxopentyl]amino]butanoic acid.

140. A method according to claim 135 wherein the compound is ethyl 3-[[5-[4-(aminoiminomethyl) phenyl]-1-oxopentyl]amino]-4-pentenoate.

141. A method according to claim 135 wherein the compound is β-[[5-[4-(aminoiminomethyl)phenyl]-1-oxopentyl]amino]-3-cyclohexene-1-propanoic acid.

142. A method according to claim 135 wherein the compound is 3R-[[5-[4-(aminoiminomethyl)phenyl]-1-oxopentyl]amino]butanoic acid.

143. A method according to claim 135 wherein the compound is 3-[[5-[4-(aminoiminomethyl)phenyl]-4-methylene-1-oxopentyl]amino]butanoic acid.

144. A method according to claim 135 wherein the compound is 3-[[5-[4-(aminoiminomethyl)phenyl]-4-methyl-1-oxopentyl]amino]butanoic acid.

145. A method according to claim 136 wherein the compound is ethyl β-[[5-[4-(aminoiminomethyl) phenyl]-1-oxopentyl]amino]-4-benzenepropanoate.

146. A method according to claim 136 wherein the compound is β-[[5-[4-(aminoiminomethyl)phenyl]-1-oxopentyl]amino]benzenepropanoic acid, acetate salt.

147. A method according to claim 136 wherein the compound is β-[[5-[4-(aminoiminomethyl)phenyl]-1-oxopentyl]amino]-4-ethoxybenzenepropanoic acid.

148. A method according to claim 136 wherein the compound is ethyl β-[[5-[4-(aminoiminomethyl) phenyl]-1-oxopentyl]amino]-4ethoxybenzenepropanoate.

149. A method according to claim 136 wherein the compound is β-[[5-[4-(aminoiminomethyl)phenyl]-1-oxopentyl]amino]-4-cyanobenzenepropanoic acid.

150. A method according to claim 136 wherein the compound is β-[[5-[4-(aminoiminomethyl)-phenyl]-1-oxopentyl]amino]-4-fluorobenzenepropanoic acid.

151. A method according to claim 136 wherein the compound is β-[[5-[4[(aminoiminomethyl)phenyl]-1-oxo-4-pentynyl]amino]benzenepropanoic acid.

152. A method according to claim 136 wherein the compound is β-[[5-[4-(aminoiminomethyl)phenyl]-1-oxopentyl]amino]-N-hydroxybenzenepropanamide.

153. A method according to claim 137 wherein the compound is β-[[5-[4-(aminoiminomethyl)phenyl]-1-oxopentyl]amino]-3-pyridinepropanoic acid.

154. A method according to claim 137 wherein the compound is ethyl β-[[5-[4-(aminoiminomethyl) phenyl]-1-oxopentyl]amino]-3-pyridinepropanoate.

155. A method according to claim 137 wherein the compound is β-[[5-[4-(aminoiminomethyl)phenyl]-1-oxopentyl]amino]-1,3-benzodioxole-5-propanoic acid.

156. A method according to claim 137 wherein the compound is ethyl β-[[5-[4-(aminoiminomethyl) phenyl]-1-oxopentyl]amino]-1-1,3-benzodioxole-5-propanoate.

157. A method according to claim 137 wherein the compound is β-[[5-[4-(aminoiminomethyl)phenyl]-1-oxopentyl]amino]-2-pyridinepropanoic acid.

* * * * *